(12) United States Patent
Jang et al.

(10) Patent No.: US 10,968,208 B2
(45) Date of Patent: Apr. 6, 2021

(54) COMPOUND FOR ORGANIC ELECTRONIC ELEMENT, ORGANIC ELECTRONIC ELEMENT COMPRISING THE SAME, AND ELECTRONIC DEVICE THEREOF

(71) Applicant: DUK SAN NEOLUX CO., LTD., Cheonan-si (KR)

(72) Inventors: Jae Wan Jang, Cheonan-si (KR); Wonsam Kim, Hwaseong-si (KR); Bo Ram Park, Mokpo-si (KR); Seung-Won Choi, Yongin-si (KR); Jong-Jin Ha, Cheonan-si (KR); Junghwan Park, Hwaseong-si (KR); Sun-Hee Lee, Hwaseong-si (KR); Mun Jae Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 408 days.

(21) Appl. No.: 15/758,827

(22) PCT Filed: Aug. 30, 2016

(86) PCT No.: PCT/KR2016/009642
§ 371 (c)(1),
(2) Date: Mar. 9, 2018

(87) PCT Pub. No.: WO2017/043797
PCT Pub. Date: Mar. 16, 2017

(65) Prior Publication Data
US 2020/0223835 A1    Jul. 16, 2020

(30) Foreign Application Priority Data

Sep. 9, 2015  (KR) .................. 10-2015-0127670

(51) Int. Cl.
| | | |
|---|---|---|
| *C07D 411/14* | (2006.01) | |
| *C07D 405/14* | (2006.01) | |
| *C07D 407/14* | (2006.01) | |
| *C07D 407/02* | (2006.01) | |
| *C07D 491/048* | (2006.01) | |
| *C07D 519/00* | (2006.01) | |
| *H01L 51/00* | (2006.01) | |

(52) U.S. Cl.
CPC .......... *C07D 411/14* (2013.01); *C07D 405/14* (2013.01); *C07D 407/02* (2013.01); *C07D 407/14* (2013.01); *C07D 491/048* (2013.01); *C07D 519/00* (2013.01); *H01L 51/0005* (2013.01); *H01L 51/0059* (2013.01); *H01L 51/0067* (2013.01); *H01L 51/0072* (2013.01); *H01L 51/0073* (2013.01); *H01L 51/0074* (2013.01)

(58) Field of Classification Search
CPC ... C07D 411/14; C07D 405/14; C07D 407/14
See application file for complete search history.

(56) References Cited

U.S. PATENT DOCUMENTS

| | | | | |
|---|---|---|---|---|
| 2004/0122230 A1* | 6/2004 | Welsh | ............. | A61P 1/00 546/35 |
| 2013/0099208 A1 | 4/2013 | Lee et al. | | |

FOREIGN PATENT DOCUMENTS

| | | |
|---|---|---|
| CN | 103058987 A | 4/2013 |
| KR | 10-2010-0108924 A | 10/2010 |
| KR | 10-2012-0096383 A | 8/2012 |
| KR | 10-2012-0116879 A | 10/2012 |
| KR | 10-2013-0053846 A | 5/2013 |
| WO | 2010/114264 A2 | 10/2010 |

OTHER PUBLICATIONS

Chinese Office Action for corresponding Chinese Patent Application No. 201680052331.7, dated Nov. 1, 2019, seven pages.

* cited by examiner

*Primary Examiner* — Shawquia Jackson
(74) *Attorney, Agent, or Firm* — Vorys, Sater, Seymour and Pease LLP; Mih Suhn Koh

(57) ABSTRACT

The present invention provides the compound represented by Formula 1, and an organic electric element comprising a first electrode, a second electrode, and an organic material layer formed between the first electrode and the second electrode, wherein the organic material layer comprises the compound represented by Formula 1. The driving voltage of an organic electronic device can be lowered, and the luminous efficiency, color purity and life time of an organic electronic device can be improved by comprising the compound represented by Formula 1 in the organic material layer.

11 Claims, 1 Drawing Sheet

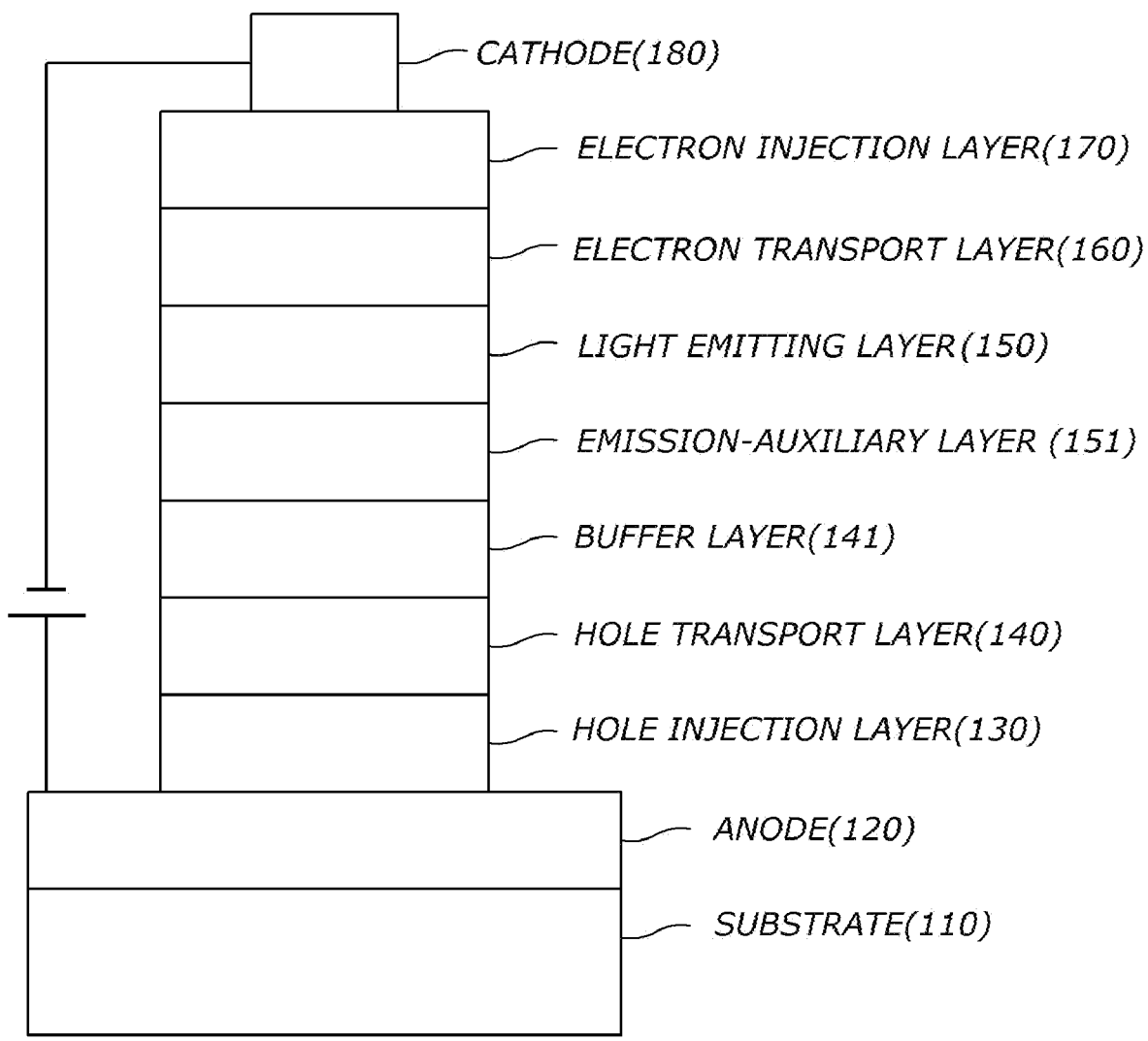

COMPOUND FOR ORGANIC ELECTRONIC ELEMENT, ORGANIC ELECTRONIC ELEMENT COMPRISING THE SAME, AND ELECTRONIC DEVICE THEREOF

CROSS-REFERENCE TO RELATED APPLICATION

This patent application claims priority from and the benefit under 35 U.S.C. 119(a) of Korean Patent Application No. 10-2015-0127670, filed on Sep. 9, 2015, which is hereby incorporated by reference for all purposes as if fully set forth herein. Further, this application claims the benefit of priority in countries other than U.S.A, which is hereby incorporated by reference herein.

BACKGROUND

Technical Field

The present invention relates to compounds for organic electric elements, organic electric elements comprising the same, and electronic devices thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed there between. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more and more as size of display becomes larger and larger in the portable display market. Therefore, the power consumption is a very important factor in the portable display with a limited power source of the battery, and the situation is such that efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Therefore it is required to develop a light emitting material that has high thermal stability and can achieve efficiently a charge balance in the light-emitting layer. In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new host materials for an organic material layer.

Object, Technical Solution and Effects of the Invention

The present invention is to provide a compound lowering driving voltage of the element, improving luminous efficiency, color purity, stability and lifetime of the element, an organic electric element comprising the same, and an electronic device thereof.

In an aspect of the present invention, the present invention provides the compound represented by formula below.

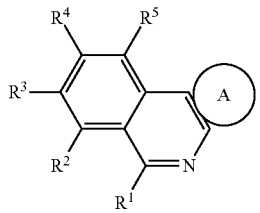

In another aspect of the present invention, the present invention provides an organic electric element using the compound represented by formula above and an electric device thereof.

By using the compound according to embodiments of the present invention, the driving voltage of element can be lowered and the luminous efficiency, color purity and lifetime of the element can be g significantly improved.

BRIEF DESCRIPTION OF THE DRAWINGS

The FIGURE illustrates an example of an organic light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

DETAILED DESCRIPTION

The FIGURE illustrates an example of an organic electric element according to an embodiment of the present invention.

Hereinafter, some embodiments of the present invention will be described in detail with reference to the accompanying illustrative drawings. In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

Unless otherwise stated, the term "alkoxyl group", "alkoxy group" or "alkyloxy group" as used herein means an oxygen radical attached to an alkyl group, but not limited to, and has 1 to 60 carbon atoms.

Unless otherwise stated, the term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below, "substituted fluorenyl group" or "substituted fluorenylene group" means, functional group which at least any one of R, R' and R" is a functional group other than hydrogen, and fluorenyl group" or "fluorenylene group" comprises Spiro compound which is formed by linking R and R' together with the carbon bonded to them.

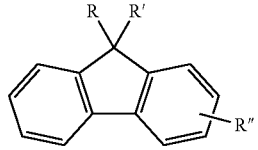

Unless otherwise stated, the term "aryl group" or "arylene group" as used herein has, but not limited to, 6 to 60 carbon atoms. The aryl group or arylene group include a monocyclic rings, ring assemblies, fused polycyclic system or Spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or Spiro compound containing one or more heteroatoms.

Also, the term "heterocyclic group" may include $SO_2$ instead of carbon consisting of cycle. For example, "heterocyclic group" includes the following compound.

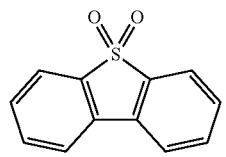 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic ring" as used herein means, ring assemblies like biphenyl and terphenyl, fused polycyclic system and Spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a Spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula:

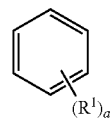

Wherein, the substituent $R^1$ is absent when a is an integer of zero, the sole $R^1$ is bonded to any one of the carbon atoms constituting the benzene ring when a is an integer of 1, when a is an integer of 2 or 3, the substituent R's may be bonded as follows and the substituents R's may be the same or different each other, and the substituent R's may be bonded to the carbon of the benzene ring in a similar manner when a is an integer of 4 to 6. Herein, the indication of the hydrogen bonded to the carbon which forms the benzene ring is omitted.

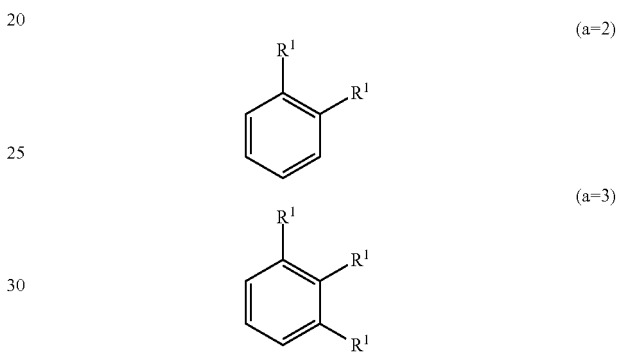

The FIG. illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 110 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, an electron transport auxiliary layer, a buffer layer 141, etc., the electron transport layer 160 or the like may serve as the hole blocking layer.

Although not shown, the organic electric element according to an embodiment of the present invention may further include a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170 and the like, as a host or a dopant material of a light emitting layer 150, or as a material of a layer for improving luminous efficiency. For example, the inventive compound may be used as material of the light emitting layer 150, the hole transport layer 140, and/or the emission-auxiliary layer 151, preferably, as material of the light emitting layer 150.

On the other hand, even if the core is the same core, the band gap, the electrical characteristics, the interface characteristics, and the like may be different depending on which substituent is bonded at which position. Therefore, it is necessary to study the selection of the core and the combination of the core and the sub-substituent bonded to the core. Specially, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, according to the present invention, energy level and $T_1$ value between the respective layers of the organic material layer, inherent material properties (mobility, interfacial properties, etc.) and the like can be optimized by forming a light emitting layer 150 which comprises the compound represented by the Formula 1, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by formula 1 below.

<Formula 1>

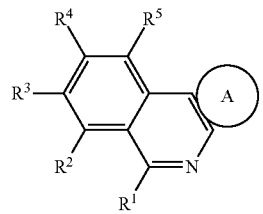

In the formula 1, each of symbols may be defined as follows.

$R^1$ is

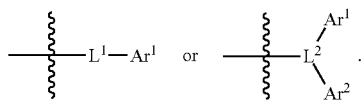

$L^1$ may be selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, and $L^2$ may be selected from the group consisting of a trivalent $C_6$-$C_{60}$ arylene group, a trivalent fluorenylene group, and a trivalent $C_2$-$C_{60}$ heterocyclic group containing at least one heteroatom selected from the group consisting of O, N, S, Si, and P.

When $L^1$ and $L^2$ are an arylene group, $L^1$ and $L^2$ may be preferably a $C_6$-$C_3O$ arylene group, more preferably a $C_6$-$C_{12}$ arylene group, for example, phenyl, biphenyl, naphthalene, etc. When $L^1$ and $L^2$ are a heterocyclic group, $L^1$ and $L^2$ may be preferably a $C_2$-$C_{30}$ heterocyclic group, more preferably a $C_2$-$C_{16}$ heterocyclic group, for example, pyridine, pyrimidine, triazine, quinazoline, benzoquinazoline, benzothienopyrimidine, benzofuropyrimidine, carbazole, benzocarbazole, pyridoindole, phenanthridine and the like.

Ar¹ and Ar² may be each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si, and P, and -L'-N($R_a$)($R_b$).

In -L'-N($R_a$)($R_b$), L' may be selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and $R_a$ and $R_b$ may be each independently selected from the group consisting of a $C_6$-$C_{60}$ aryl group, a fluorenyl group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P.

When Ar¹ and Ar² are an aryl group, Ar² and Ar$^a$ may be preferably a $C_6$-$C_{30}$ aryl group, more preferably a $C_6$-$C_{18}$ aryl group, for example, phenyl, naphthyl, biphenyl, terphenyl, phenanthrene, pyrene, triphenylene, chrysene and the like. When Ar¹ and Ar² are a heterocyclic group, Ar¹ and Ar² may be preferably a $C_2$-$C_{30}$ heterocyclic group, more preferably a $C_2$-$C_{16}$ heterocyclic group, for example, pyridine, pyrimidine, triazine, quinazoline, benzoquinazoline, dibenzothiophene, benzothienopyrimidine, benzofuropyrimidine, carbazole, benzocarbazole, pyridoindole, phenanthridine and the like. When Ar¹ and Ar² are -L'-N($R_a$)($R_b$), $R_a$ and $R_b$ may be an aryl group such as phenyl, naphthyl, biphenyl and the like, or a fluorenyl group such as 9,9-dimethyl-9H-fluorene, 9,9-diphenyl-9H-fluorene and the like.

In formula 1 above, $R^2$ to $R^5$ may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, a $C_2$-$C_{20}$ alkenyl group, a $C_1$-$C_{30}$ alkoxyl group, a $C_6$-$C_{30}$ aryloxy group.

In the formula 1, A ring is one of formulas 2 to 4 below.

<Formula 2>

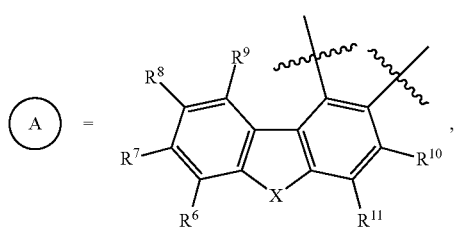

<Formula 3>

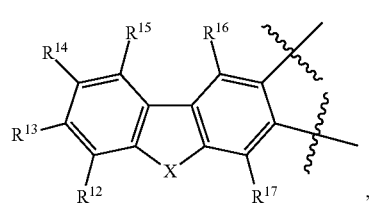

<Formula 4>

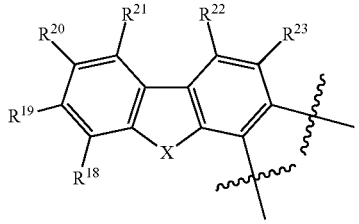

In the formulas 2 to 4, X is —O— or —S—.

In the formulas 2 to 4, $R^6$ to $R^{23}$ may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_6$-$C_{60}$ aromatic ring and a $C_3$-$C_{60}$ aliphatic ring, a $C_2$-$C_{20}$ alkenyl group, a $C_1$-$C_{30}$ alkoxyl group, and a $C_6$-$C_{30}$ aryloxy group, and neighboring groups of $R^6$ to $R^{23}$ can be linked to each other to form a ring. At this time, the formed ring may be a $C_6$-$C_{60}$ aromatic ring, a fluorene group, a $C_2$-$C_{60}$ heterocyclic group containing at least one heteroatom selected from the group consisting of O, N, S, Si, and P, or a fused ring group of a $C_6$-$C_{60}$ aromatic ring and a $C_3$-$C_{60}$ aliphatic ring, for example, a benzene ring.

Preferably, $R^1$-$R^{23}$, $R_a$, $R_b$, $L^1$, $L^2$, L', Ar¹, Ar², and a ring formed by bonding neighboring groups among $R^6$ to $R^{23}$ to each other may be each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_2$O cycloalkyl group, a $C_7$-$C_{20}$ arylalkyl group, and a $C_8$-$C_{20}$ arylalkenyl group.

Specifically, the formula 1 can be represented by one of the following formulas 5 to 10.

<Formula 5>

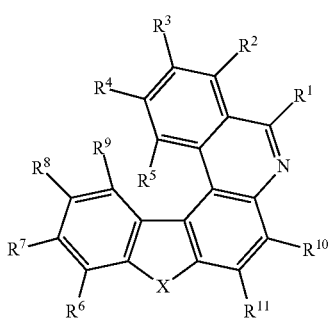

<Formula 6>

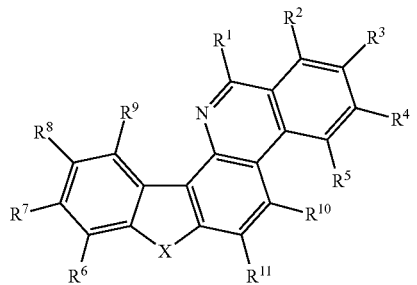

<Formula 7>

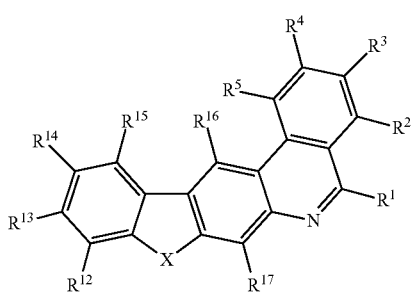

<Formula 8>

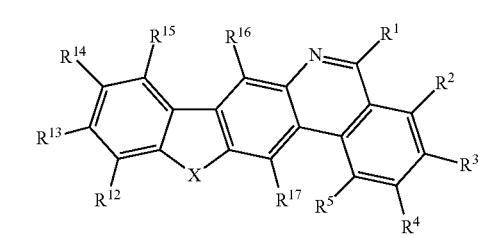

<Formula 9>

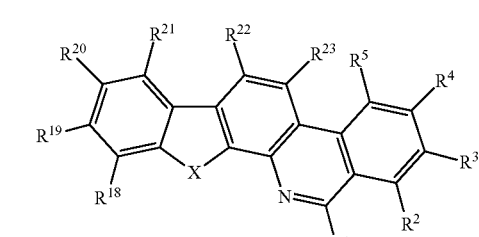

<Formula 10>

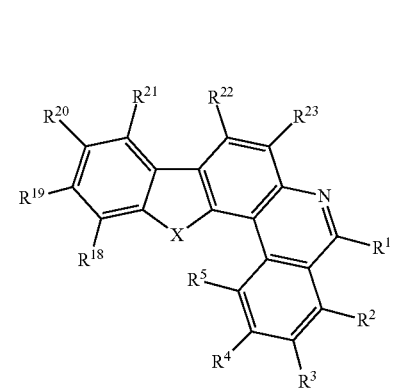

In the formulas 5 to 10, X, $R^1$ to $R^{23}$ and the like are the same as defined in the formulas 1 to 4.

Further, the formula 1 may be represented by one of the following formulas 1-1 to 1-4.

<Formula 1-1>

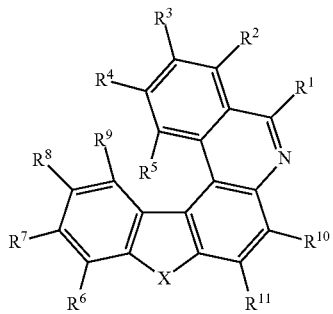

<Formula 1-2>

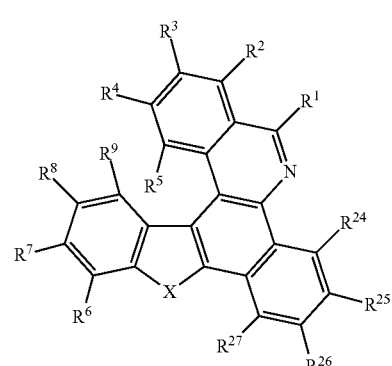

<Formula 1-3>

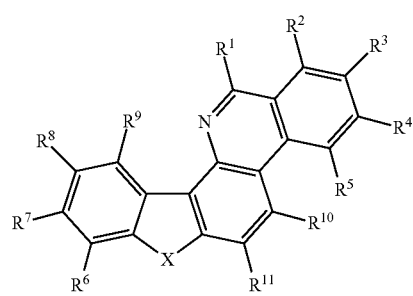

<Formula 1-4>

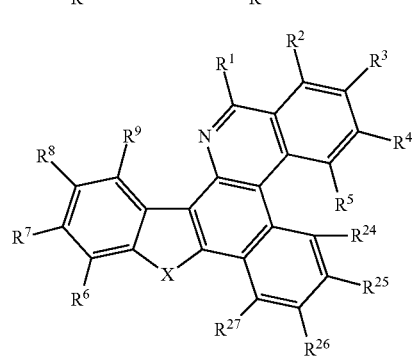

In the formulas 1-1 to 1-4, X, $R^1$ to $R^9$, and $R^{18}$ to $R^{21}$ are the same as defined in the formulas 1 to 4.

$R^{24}$ to $R^{27}$ may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_6$-$C_{60}$ aromatic ring and a $C_3$-$C_{60}$ aliphatic ring, a $C_2$-$C_{20}$ alkenyl group, a $C_1$-$C_{30}$ alkoxyl group, and a $C_6$-$C_{30}$ aryloxy group.

Specifically, the compound represented by formula 1 above may be any one of the following compounds.

P-1-1
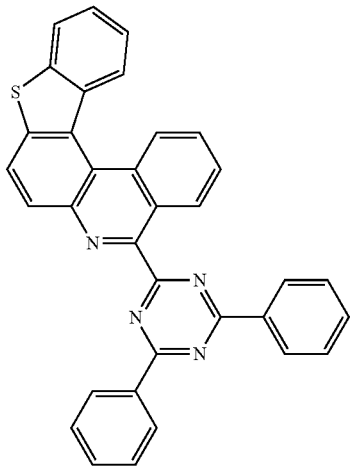
P-1-2
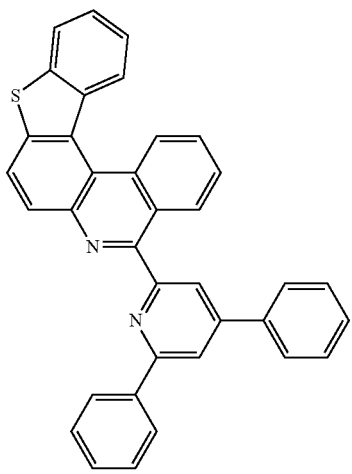
P-1-3
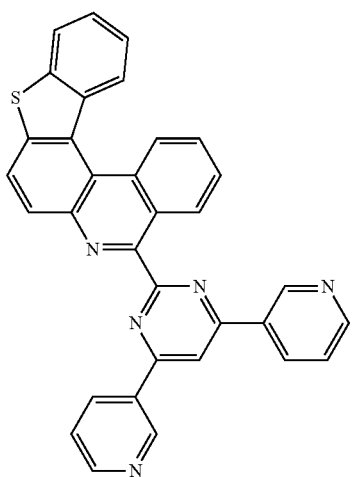
P-1-4
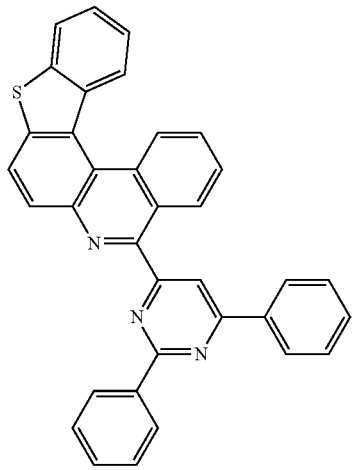
P-1-5
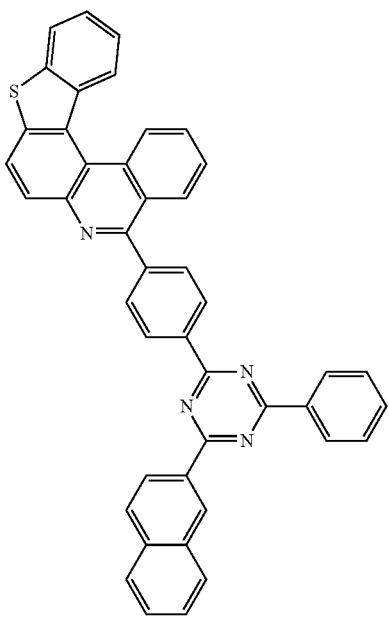
P-1-6
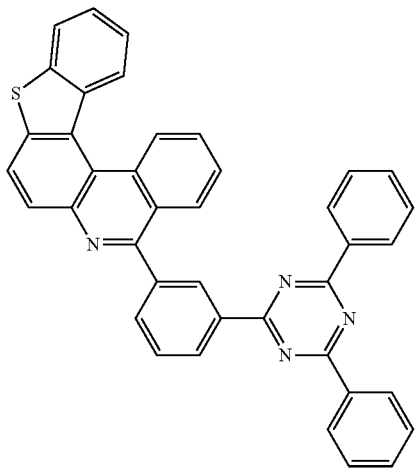

P-1-7
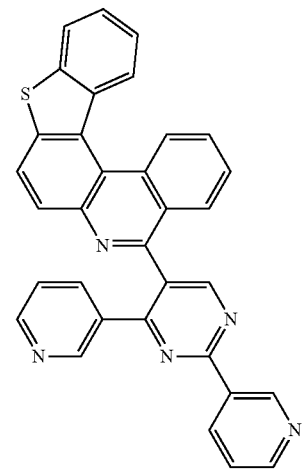
P-1-8
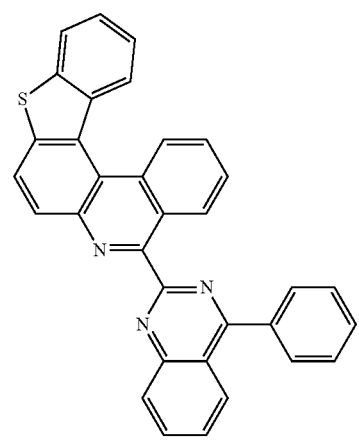
P-1-9
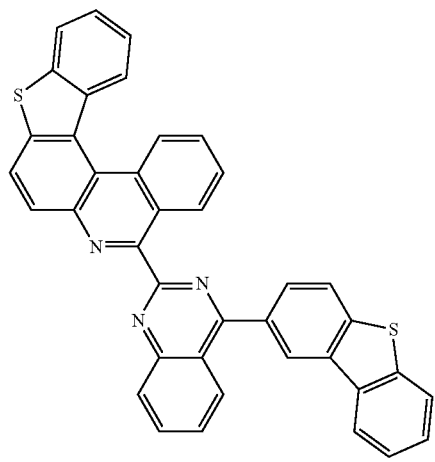
P-1-10
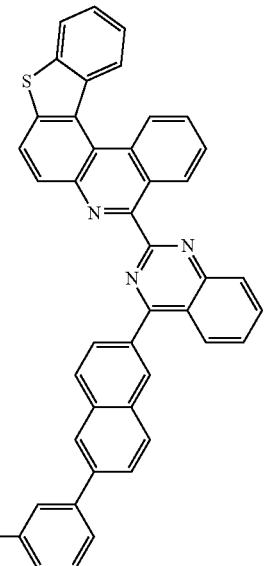
P-1-11
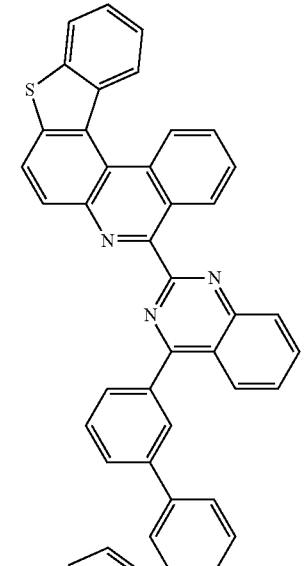
P-1-12
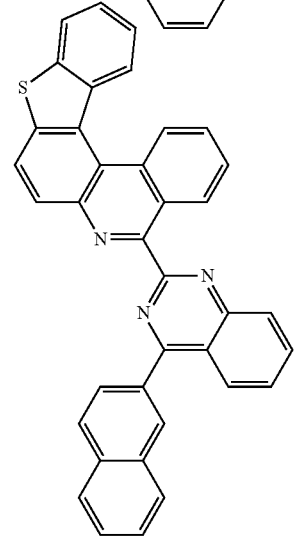

-continued
P-1-13
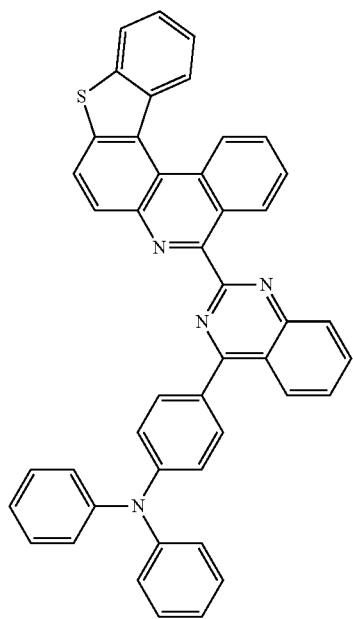
P-1-14
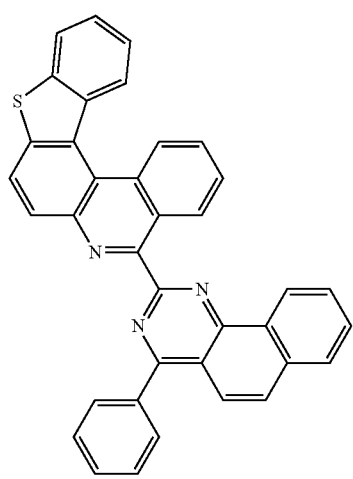
P-1-15
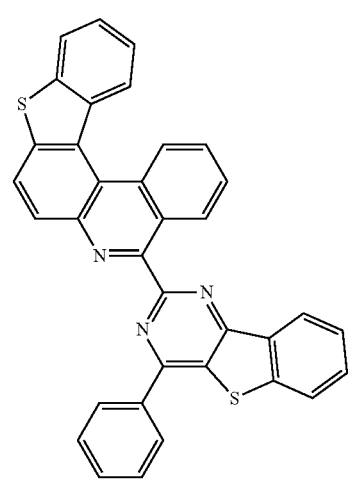
-continued
P-1-16
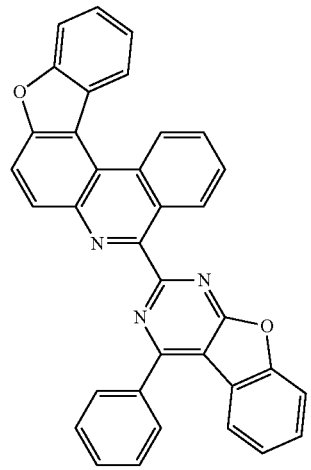
P-1-17
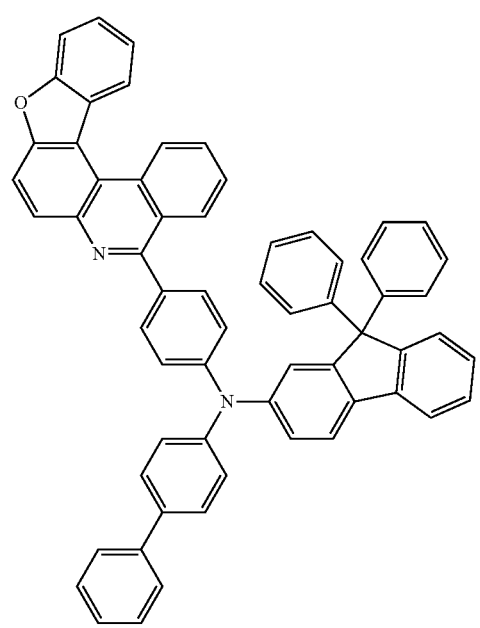
P-1-18
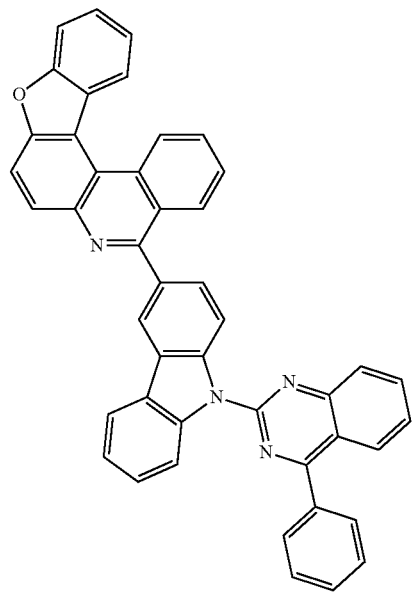

P-1-19
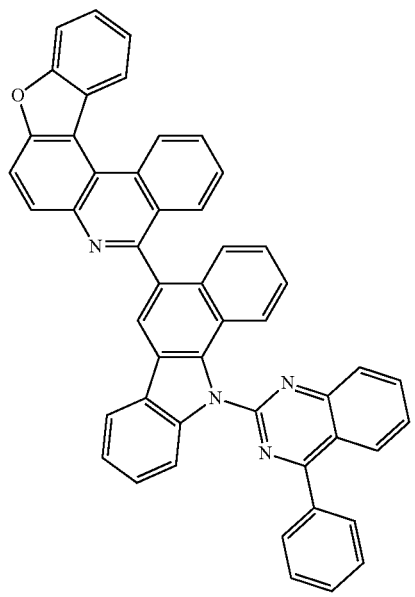
P-1-20
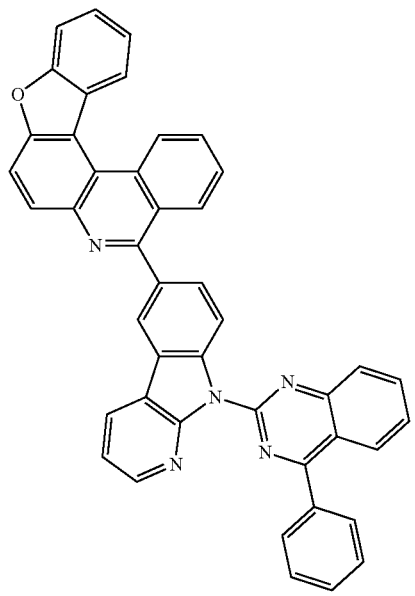
P-2-2
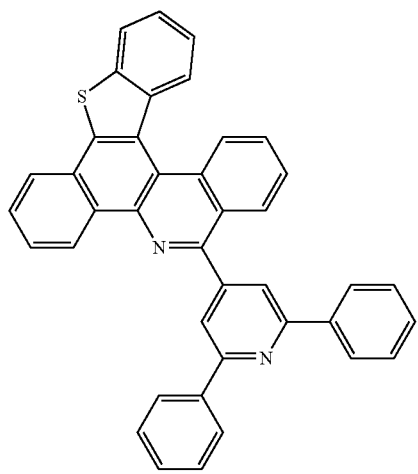
P-2-3
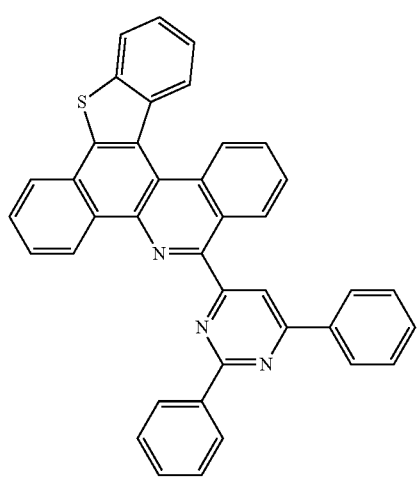
P-2-1
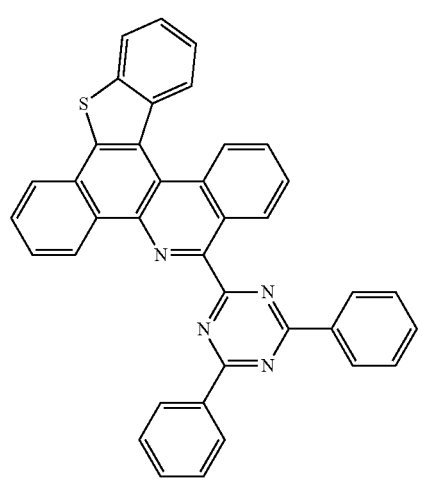
P-2-4

P-2-5
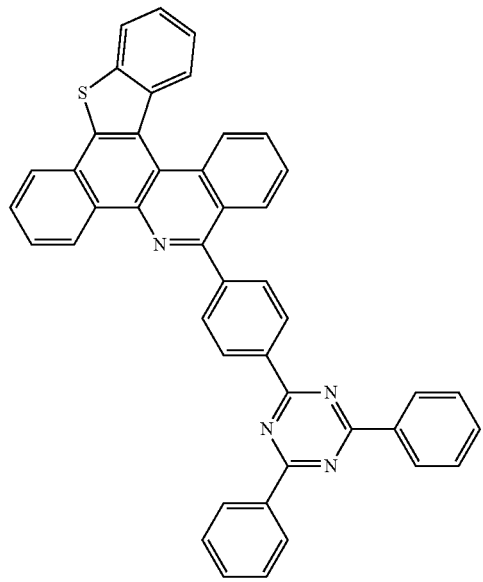
P-2-6
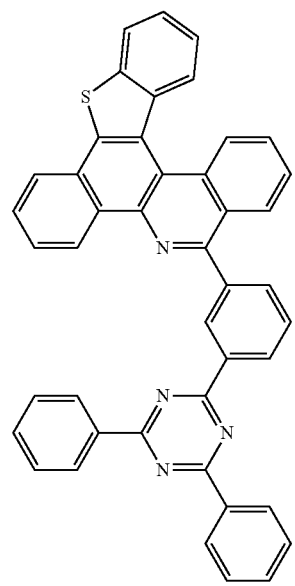
P-2-7
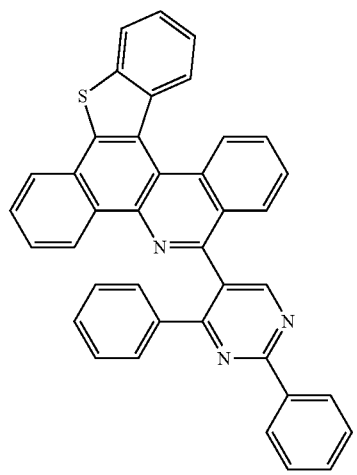
P-2-8
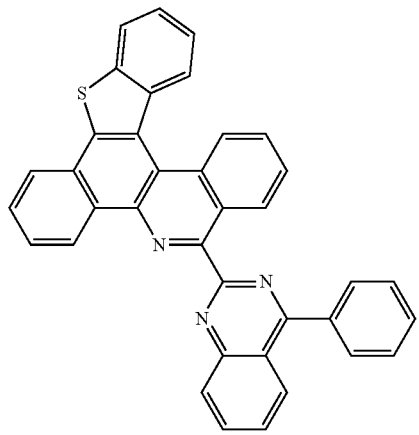
P-2-9
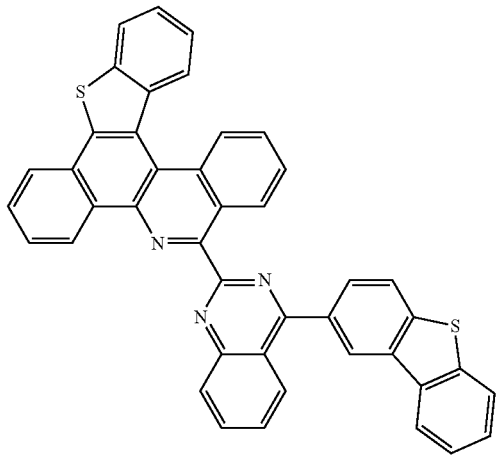
P-2-10
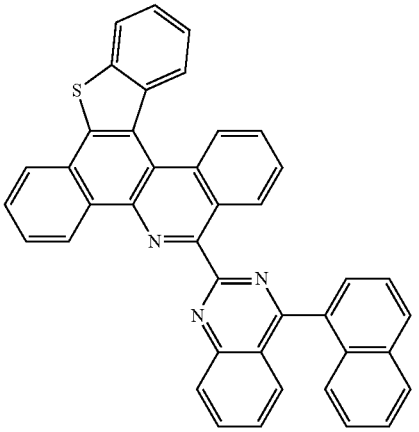

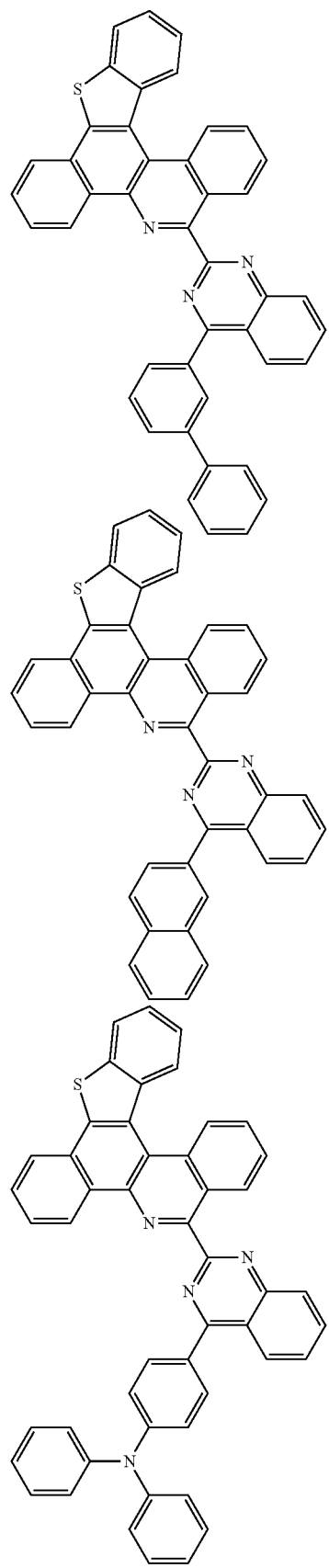
P-2-11
P-2-12
P-2-13
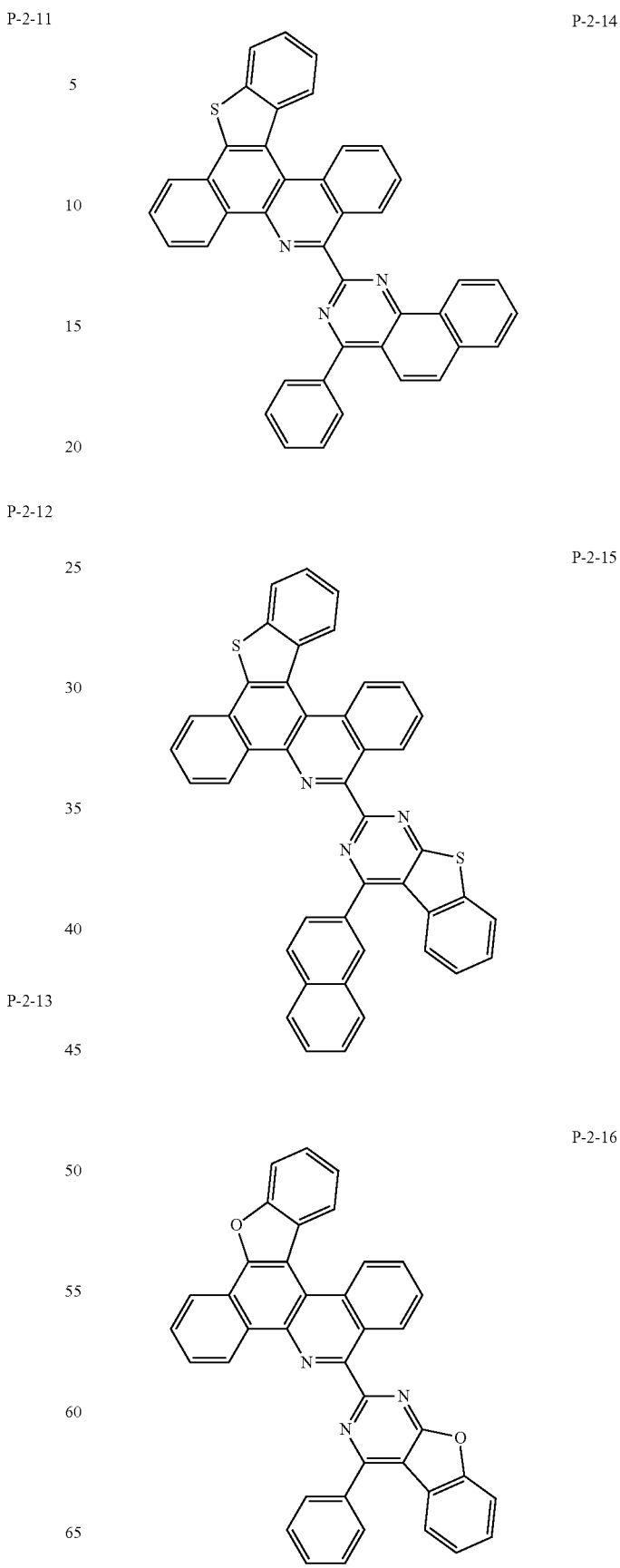
P-2-14
P-2-15
P-2-16

P-2-17
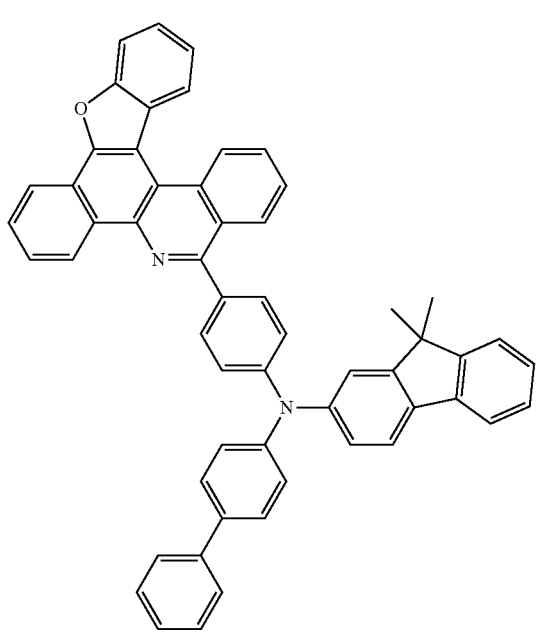
P-2-19
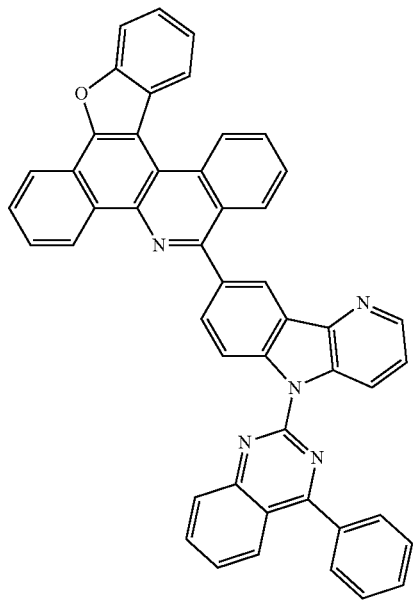
P-2-18
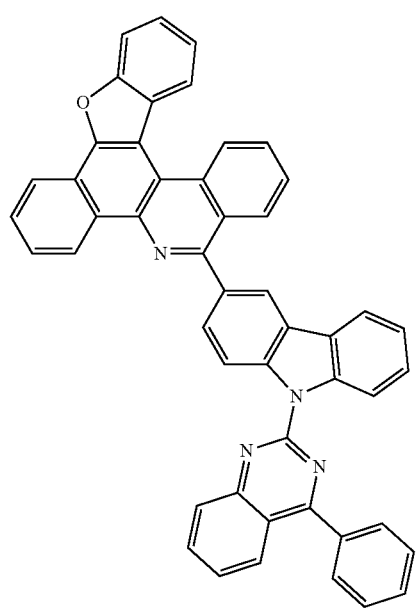
P-2-20
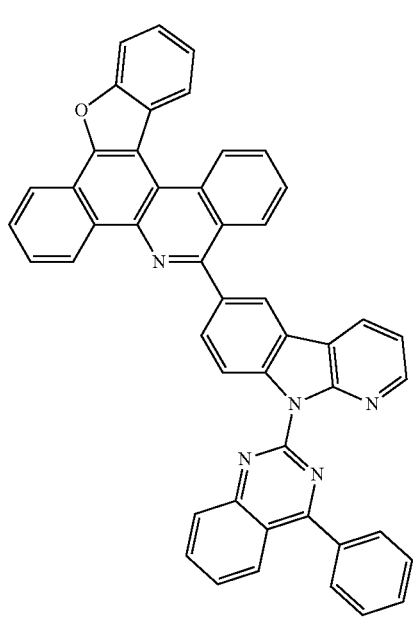

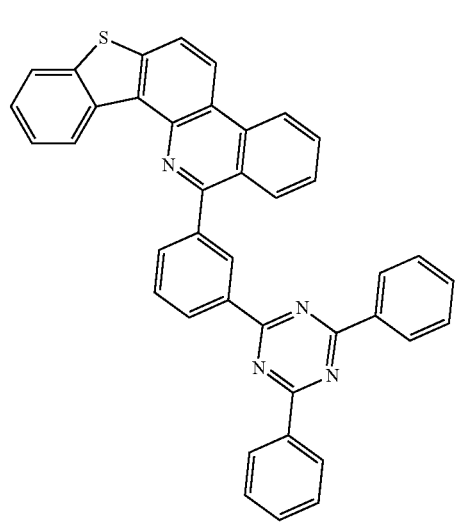
P-3-1
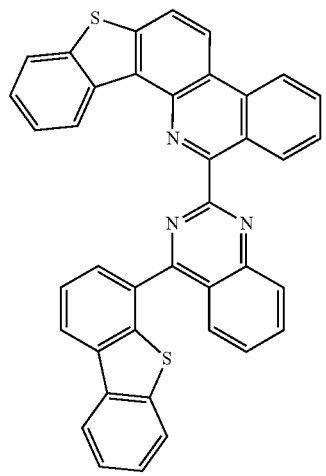
P-3-4
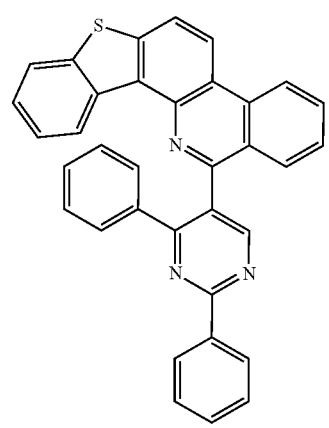
P-3-2
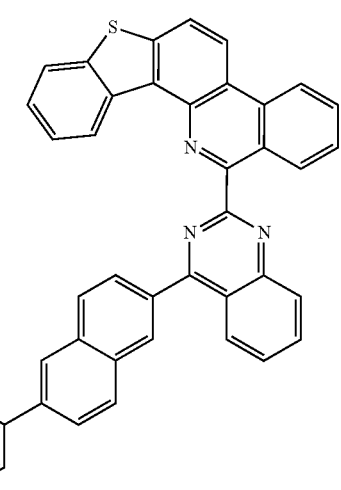
P-3-5
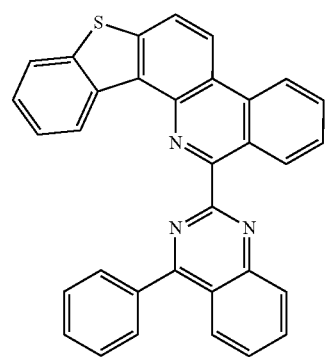
P-3-3
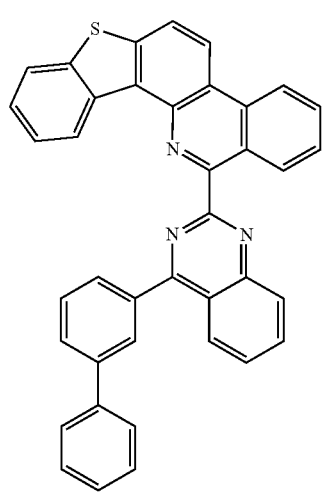
P-3-6

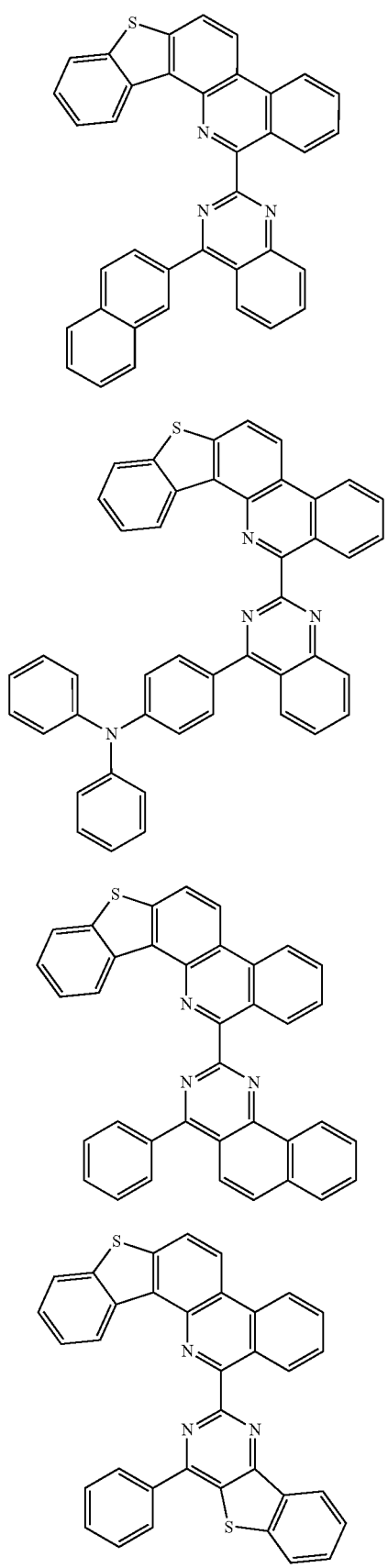
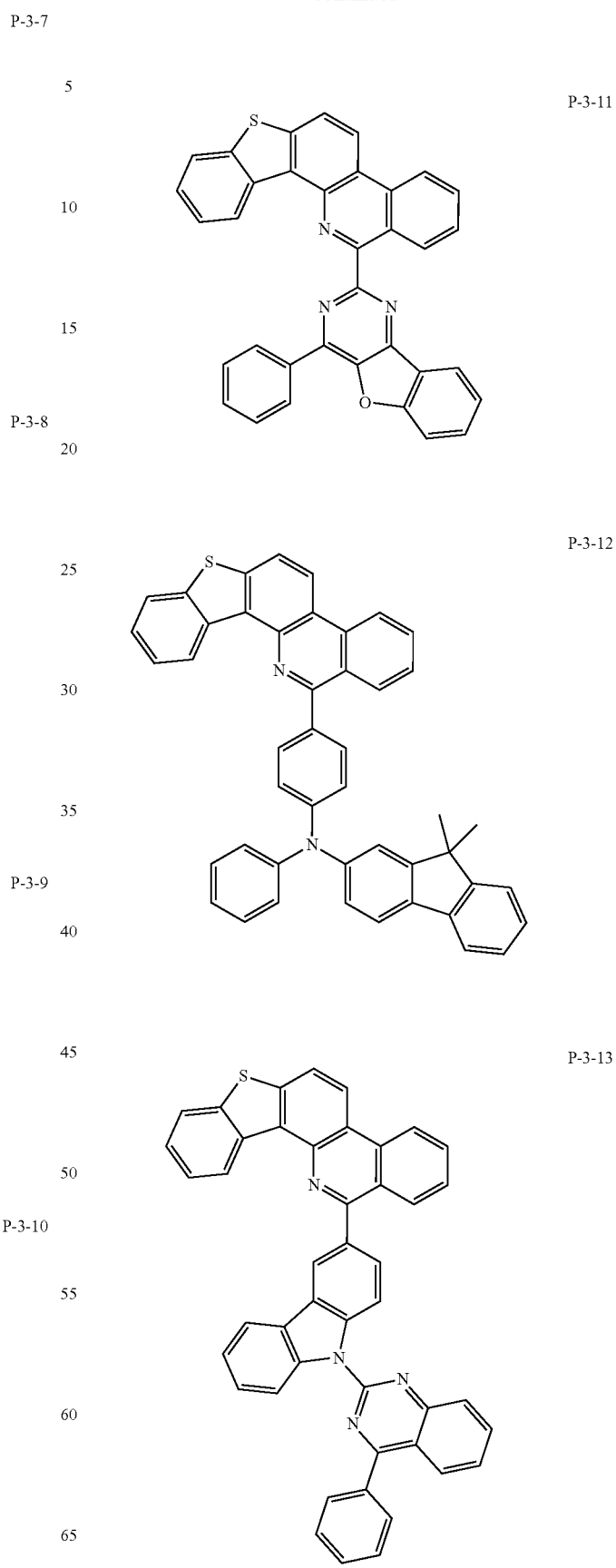

P-3-14
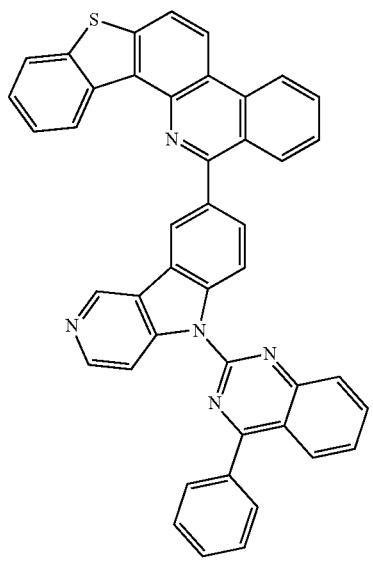
P-3-15
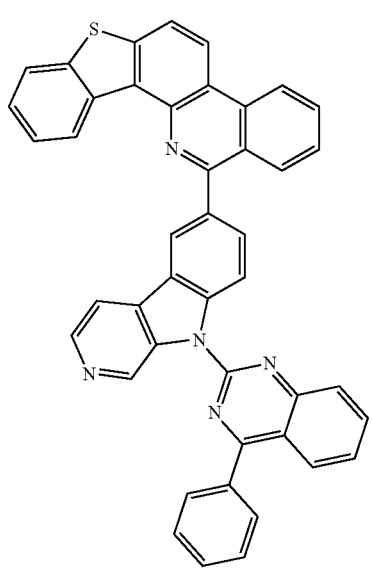
P-3-16
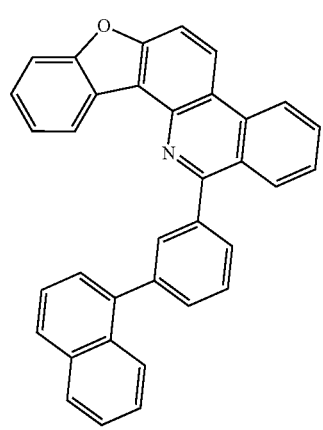
P-3-17
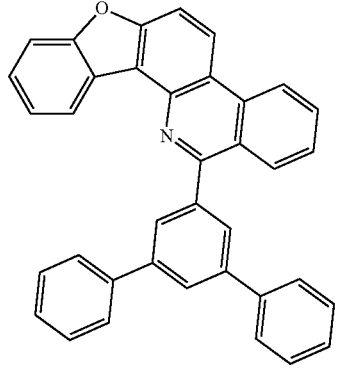
P-3-18
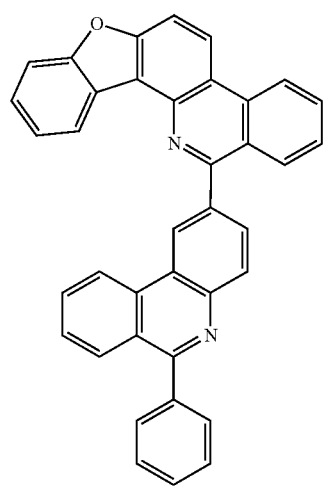
P-3-19
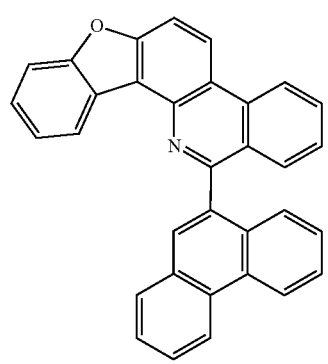

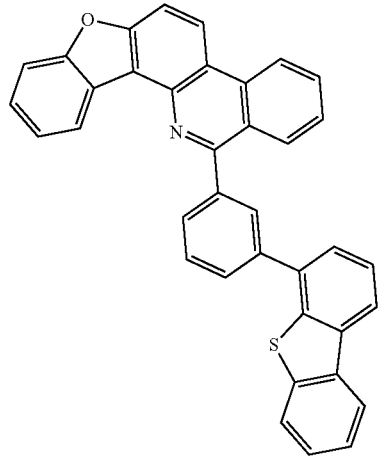
P-3-20
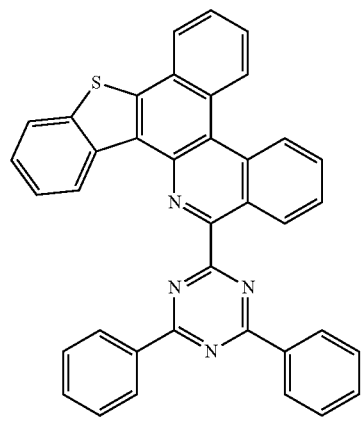
P-4-1
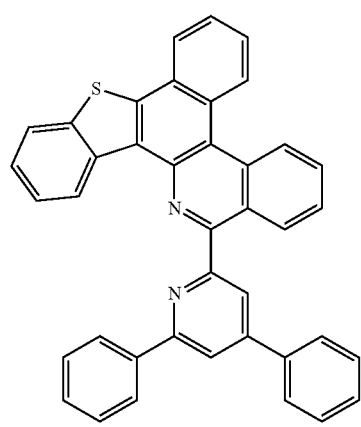
P-4-2
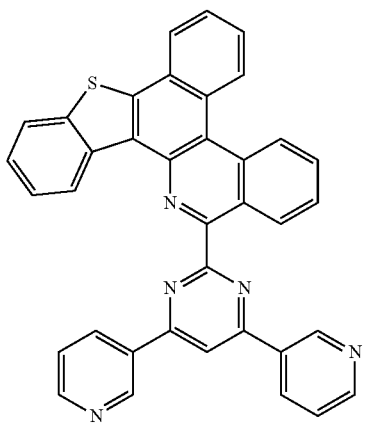
P-4-3
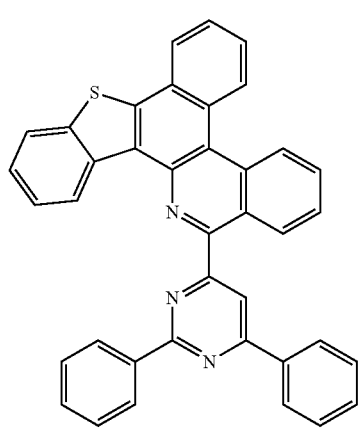
P-4-4
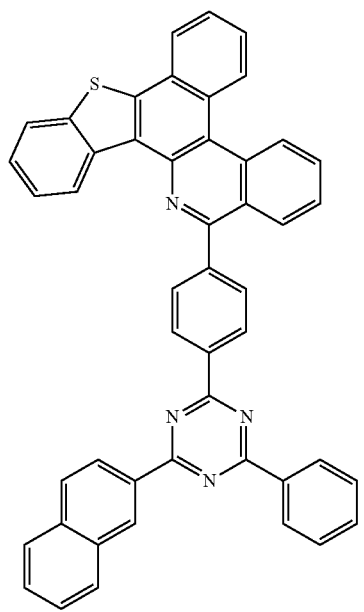
P-4-5

P-4-6
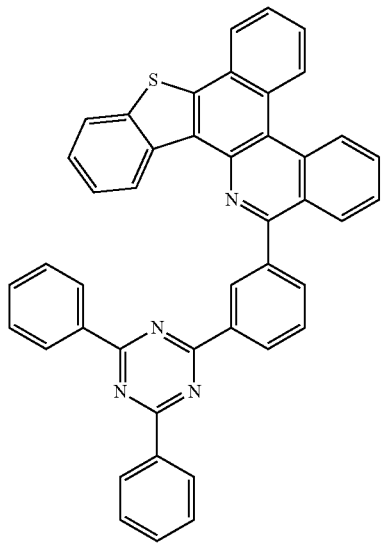
P-4-7
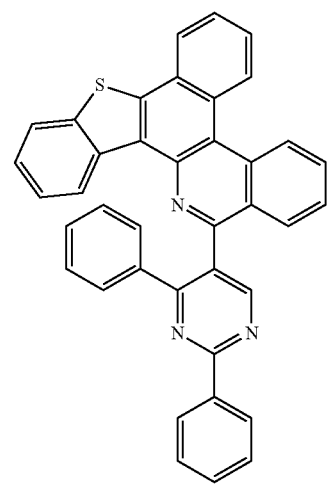
P-4-8
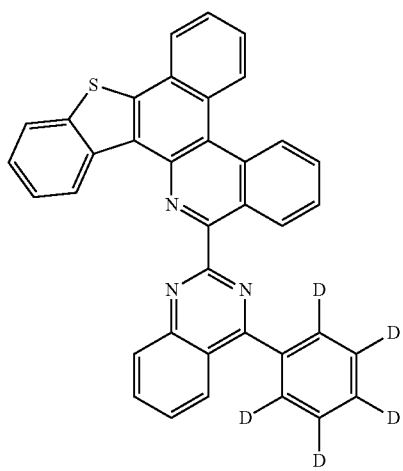
P-4-9
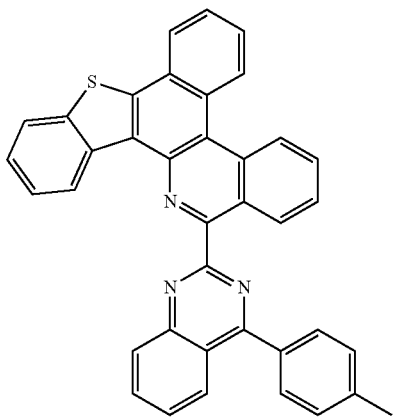
P-4-10
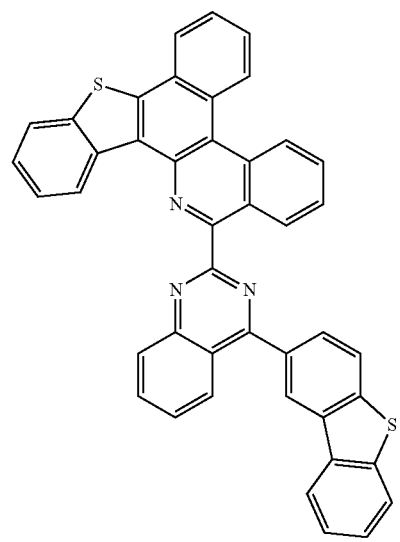
P-4-11
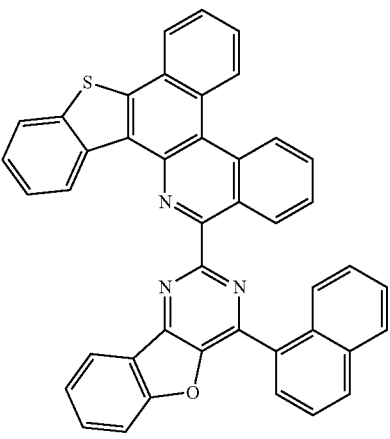

P-4-12
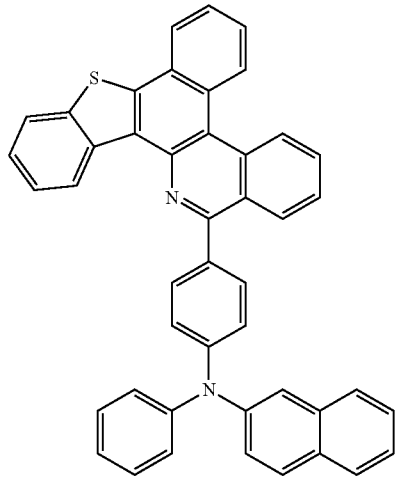
P-4-13
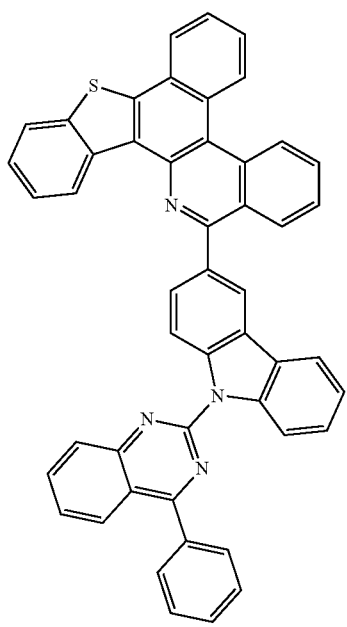
P-4-14
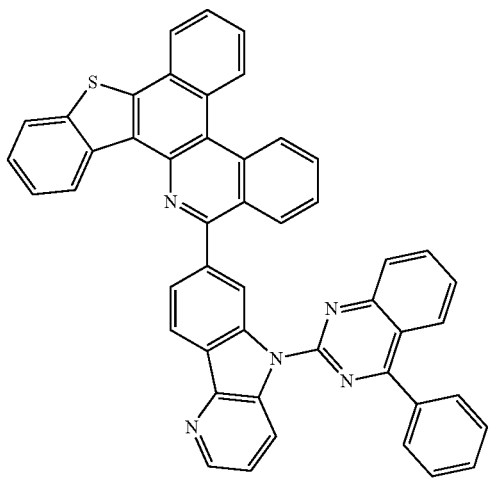
P-4-15
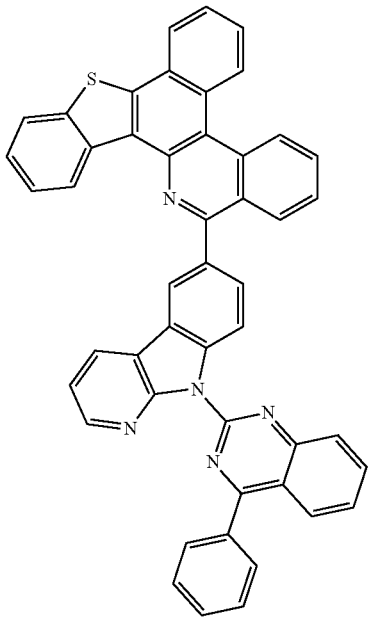
P-4-16
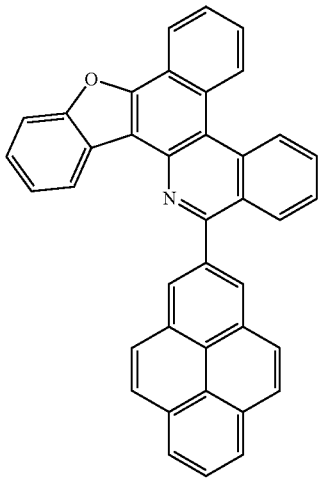
P-4-17
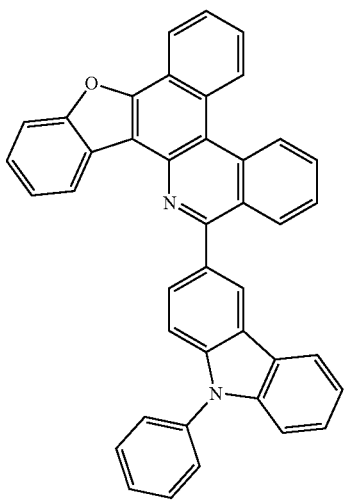

P-4-18
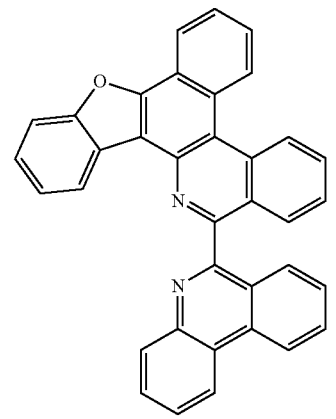
P-5-1
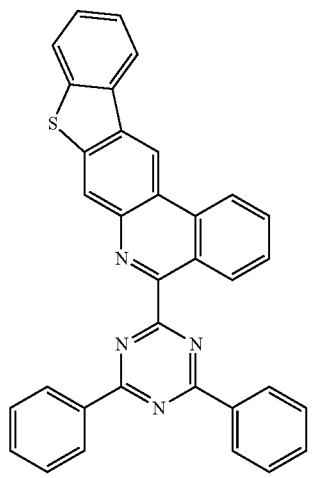
P-4-19
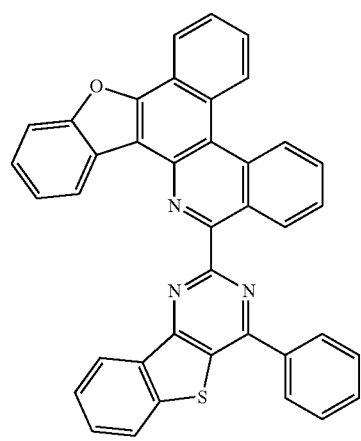
P-5-2
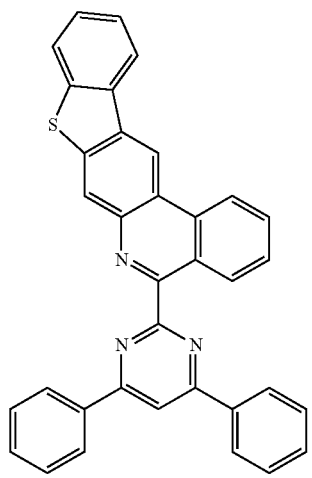
P-4-20
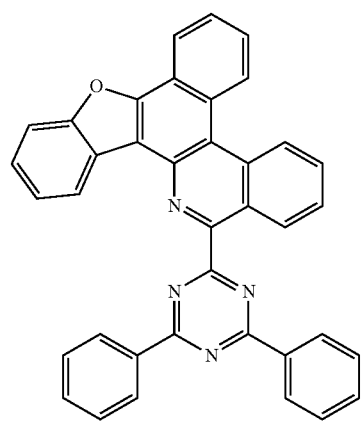
P-5-3
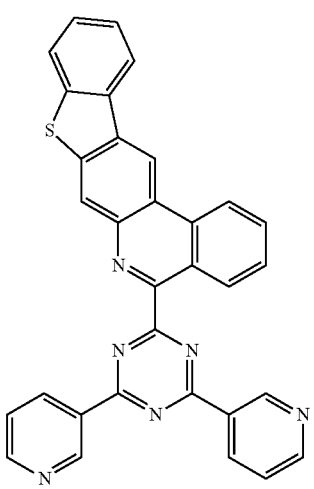

-continued
P-5-4
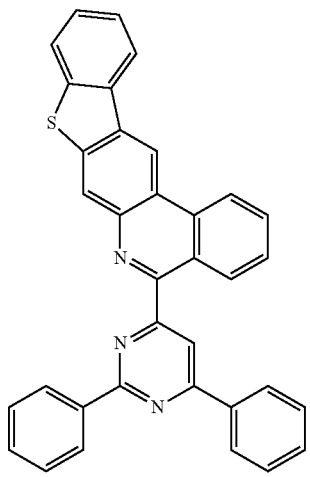
P-5-5
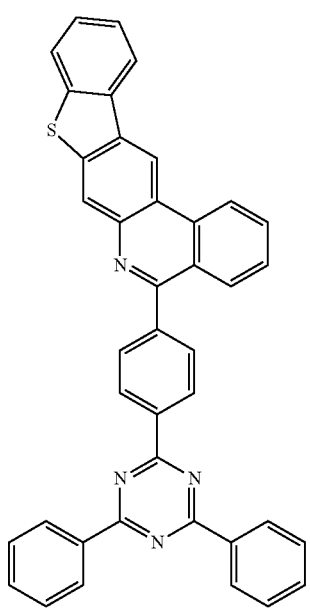
P-5-6
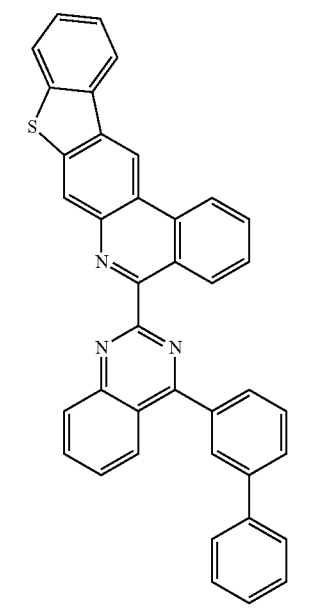
P-5-7
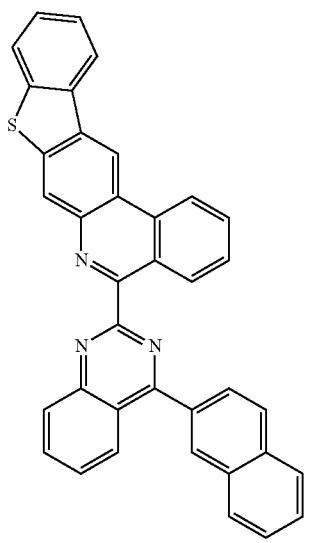
P-5-8
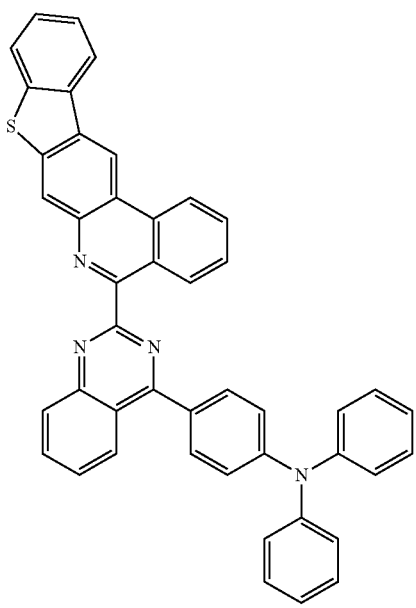
P-5-9
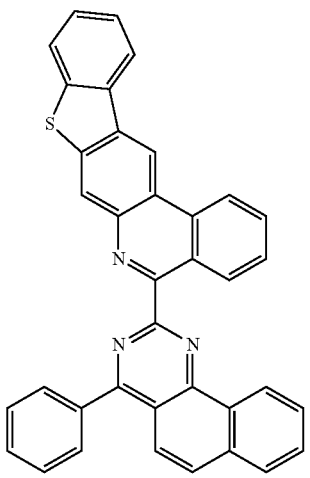

P-5-10
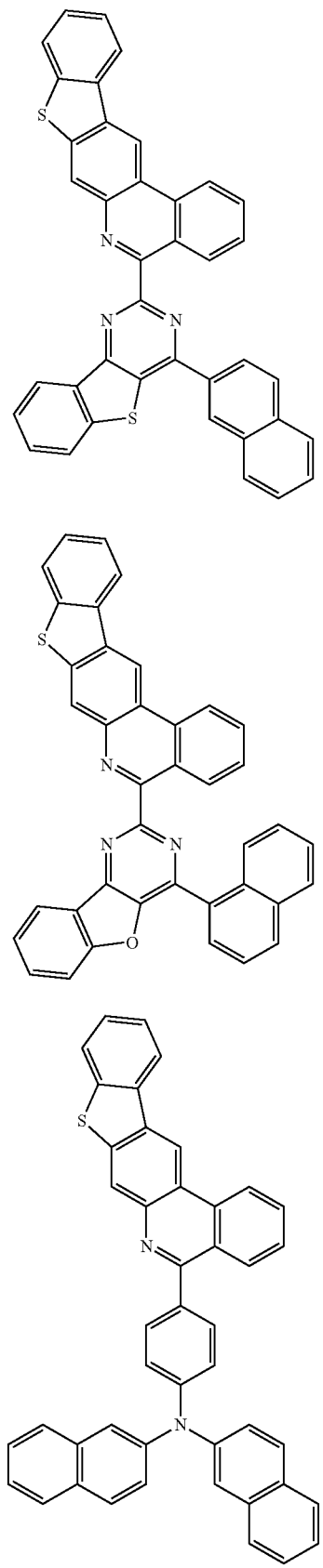
P-5-11
P-5-12
P-5-13
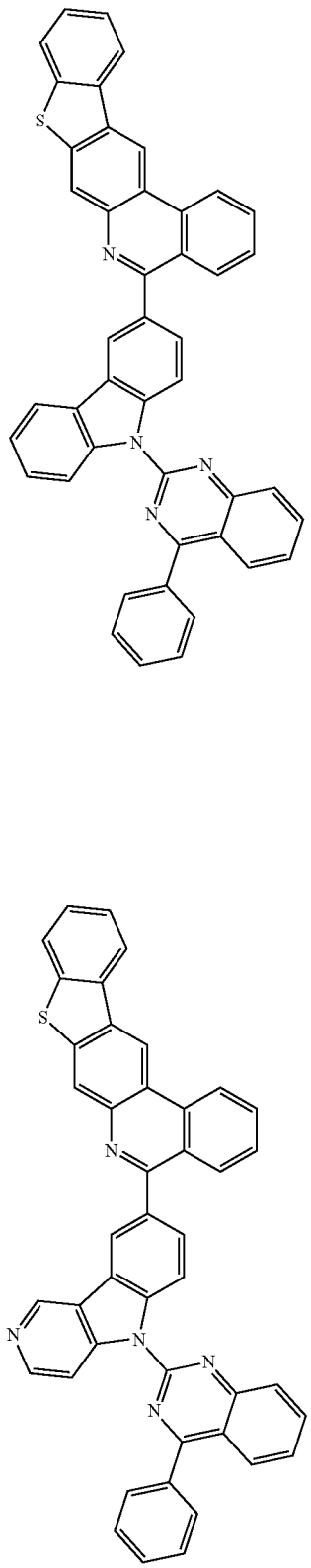
P-5-14

P-5-15
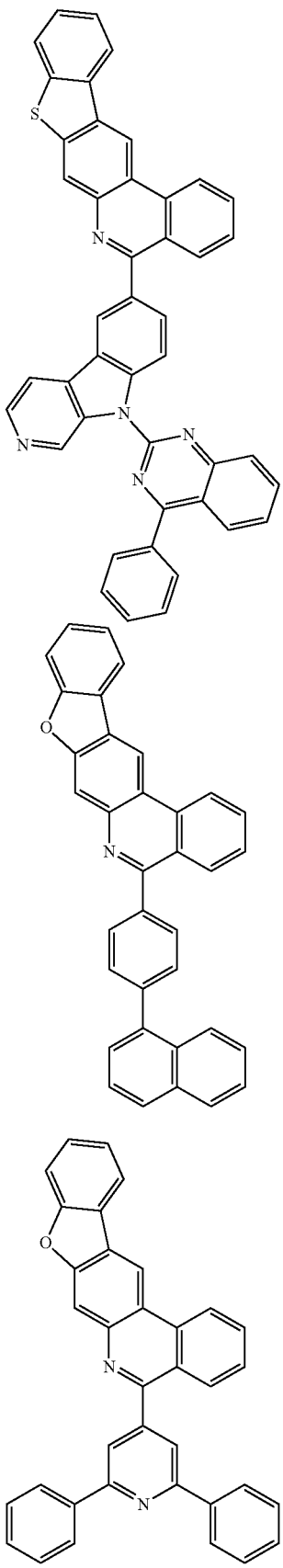
P-5-16
P-5-17
P-5-18
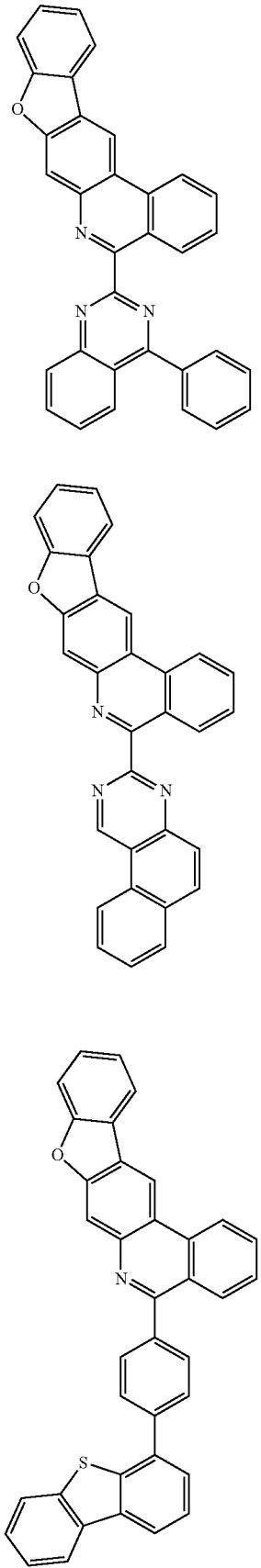
P-5-19
P-5-20

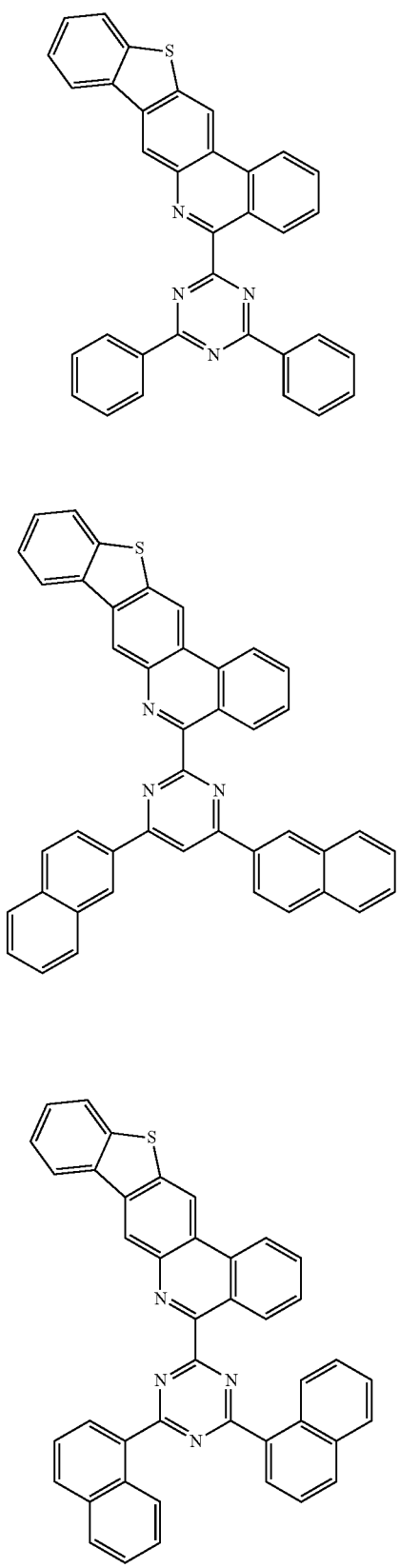
P-6-1
P-6-2
P-6-3
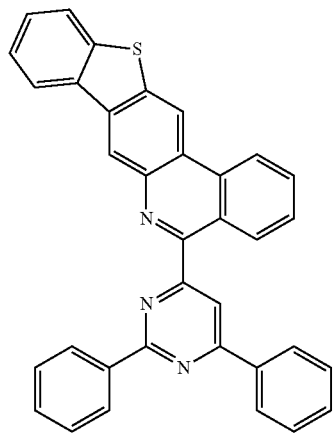
P-6-4
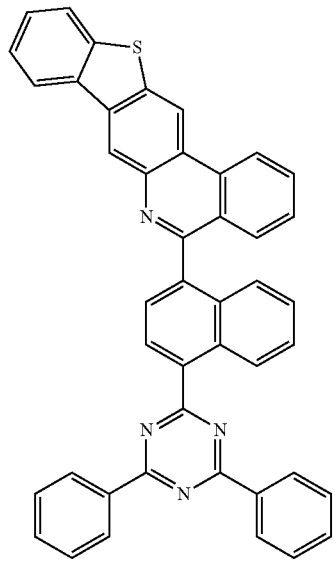
P-6-5
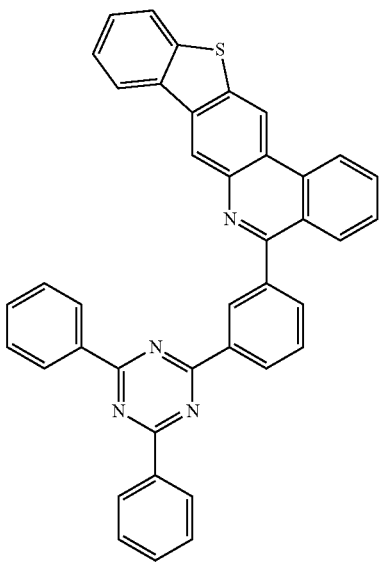
P-6-6

P-6-7
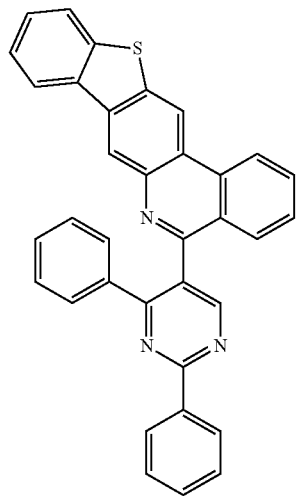
P-6-8
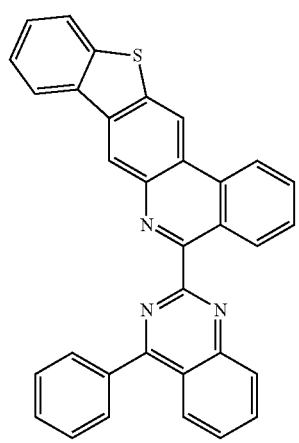
P-6-9
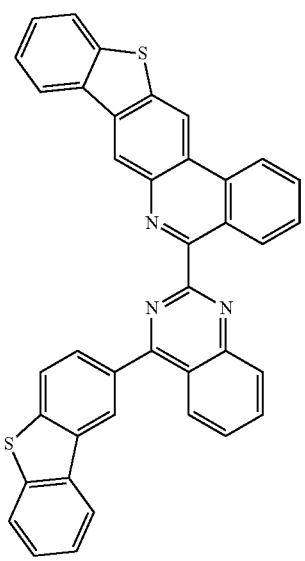
P-6-10
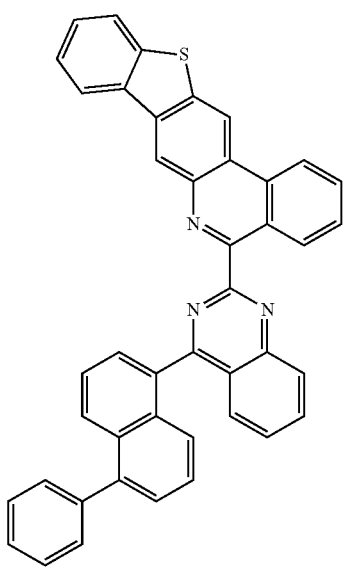
P-6-11
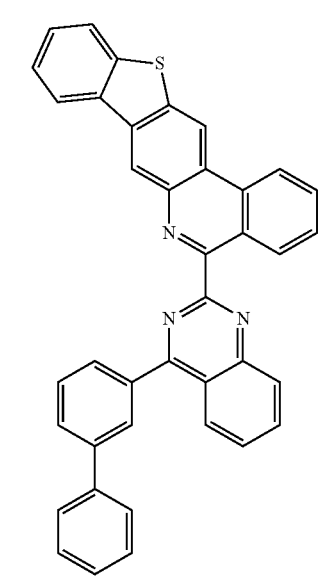
P-6-12
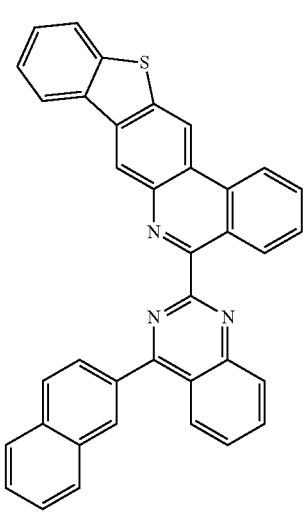

-continued
P-6-13
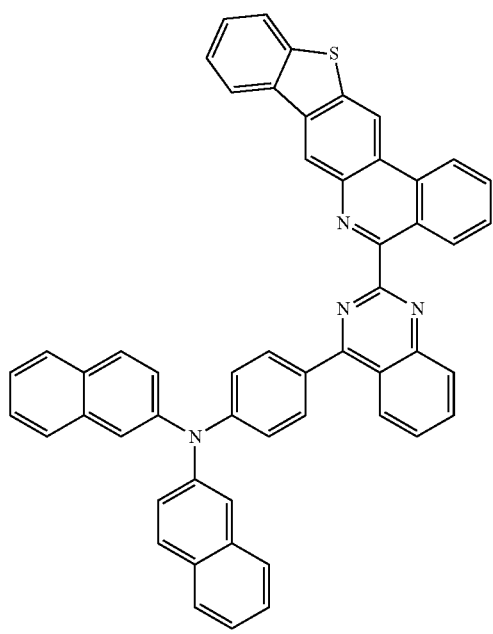
P-6-14
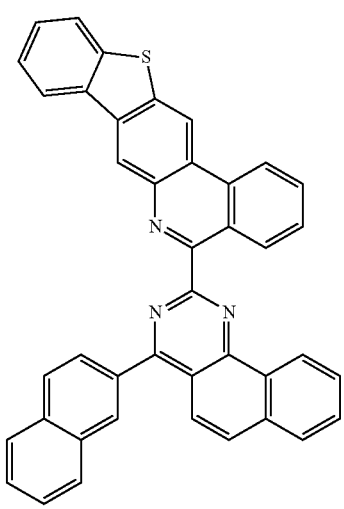
P-6-15
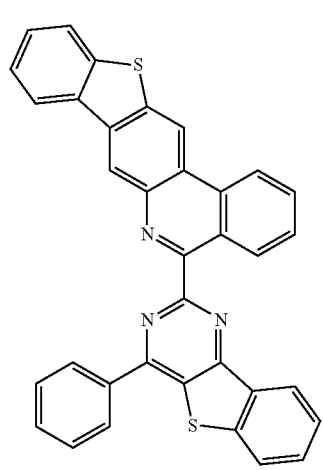
-continued
P-6-16
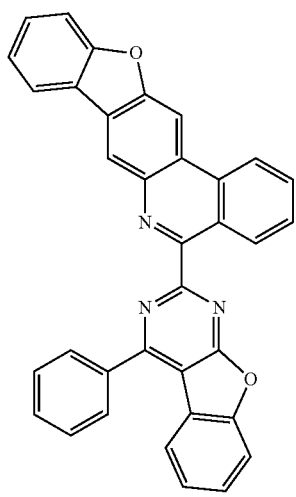
P-6-17
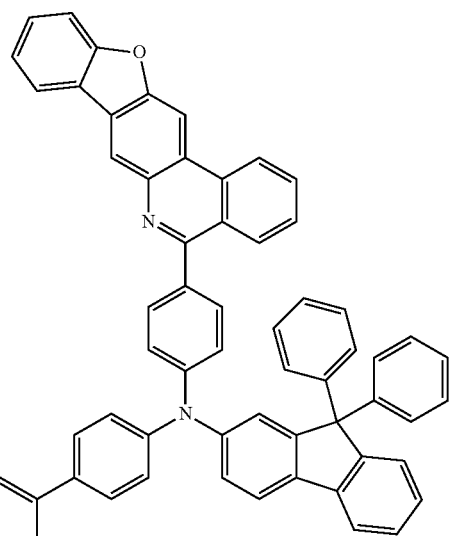
P-6-18
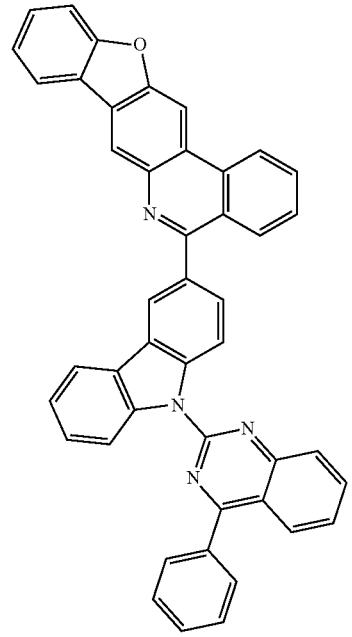

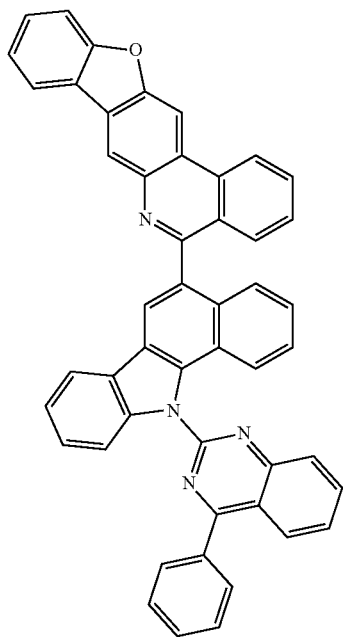
P-6-19
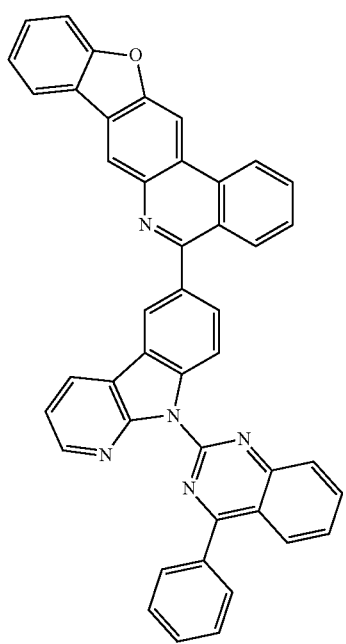
P-6-20
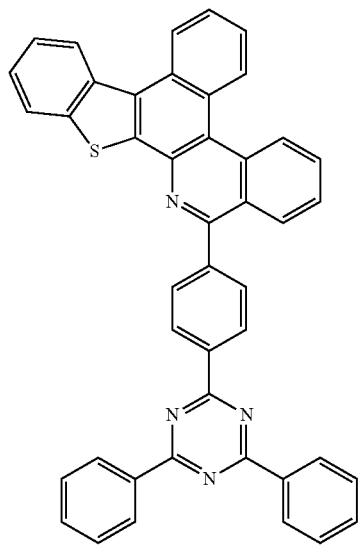
P-7-1
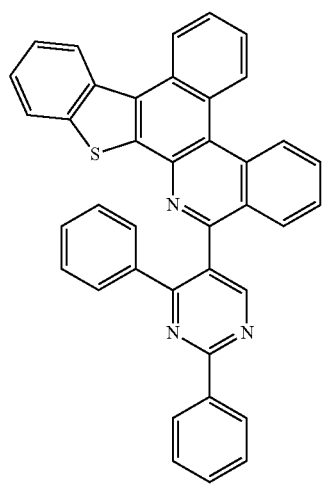
P-7-2
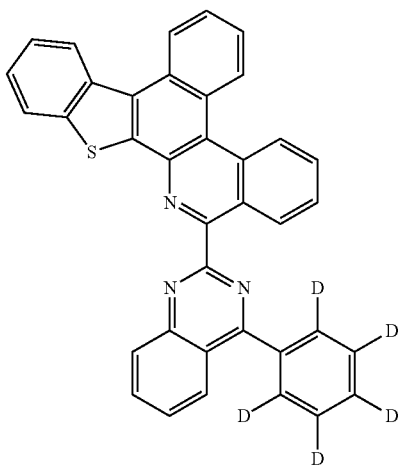
P-7-3

P-7-4
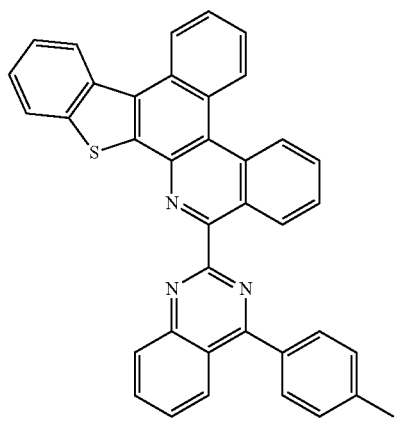
P-7-5
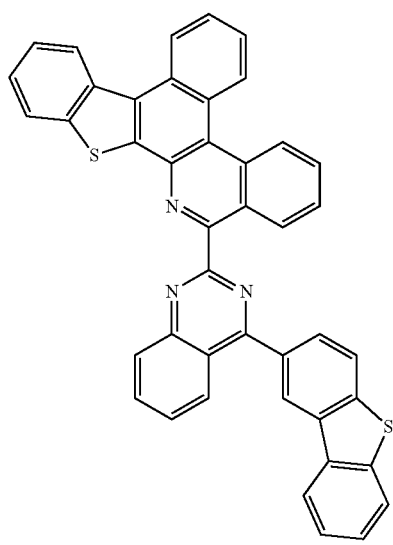
P-7-6
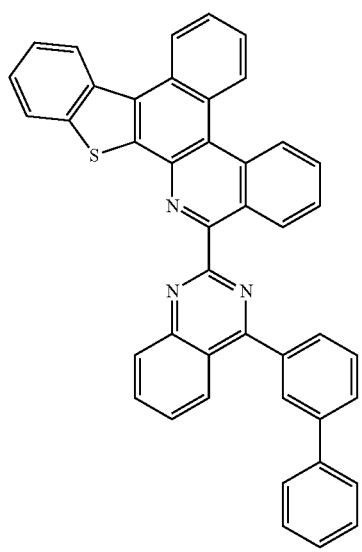
P-7-7
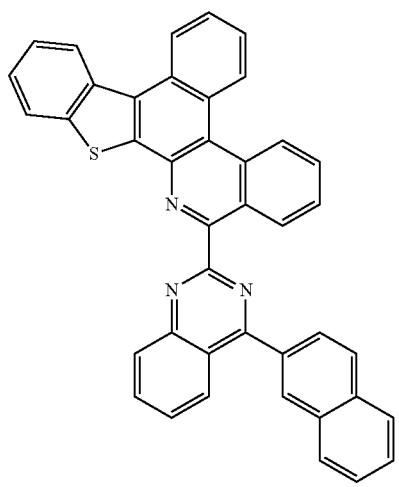
P-7-8
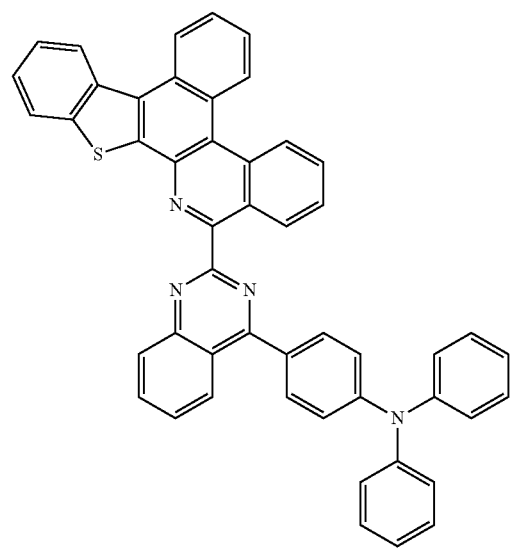
P-7-9
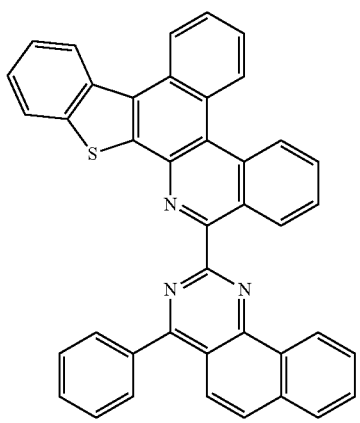

P-7-10
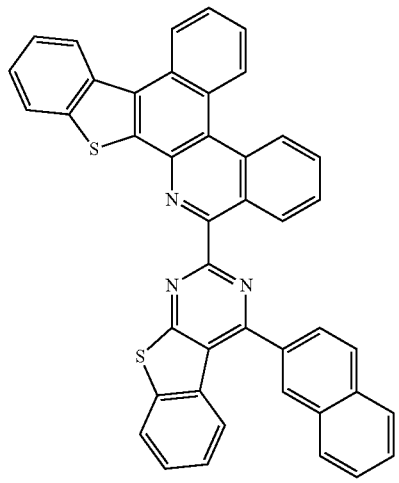
P-7-11
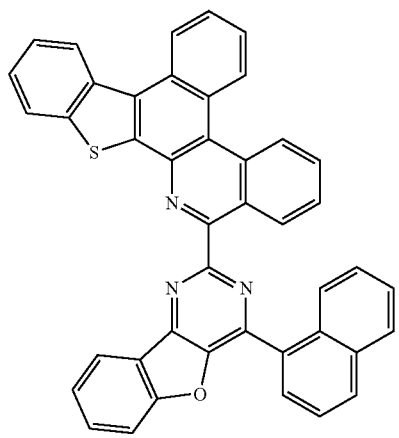
P-7-12
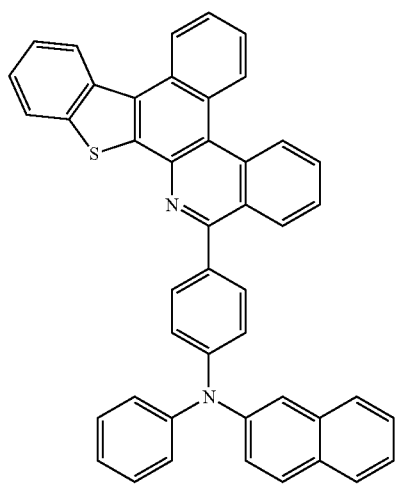
P-7-13
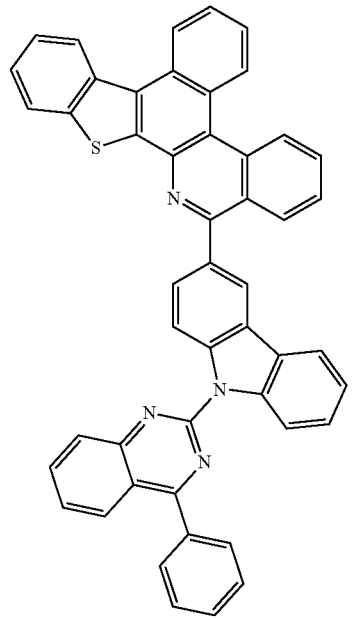
P-7-14
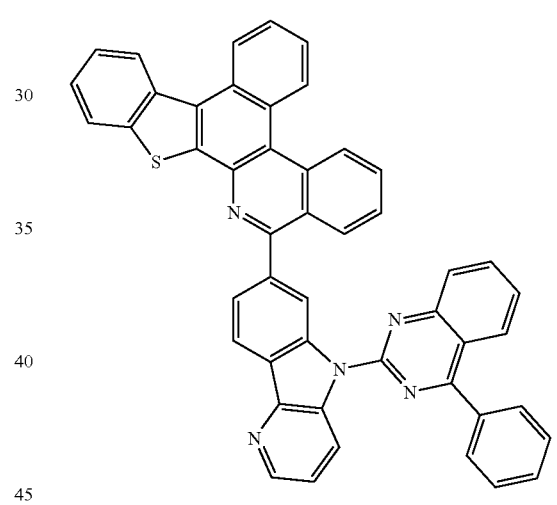
P-7-15
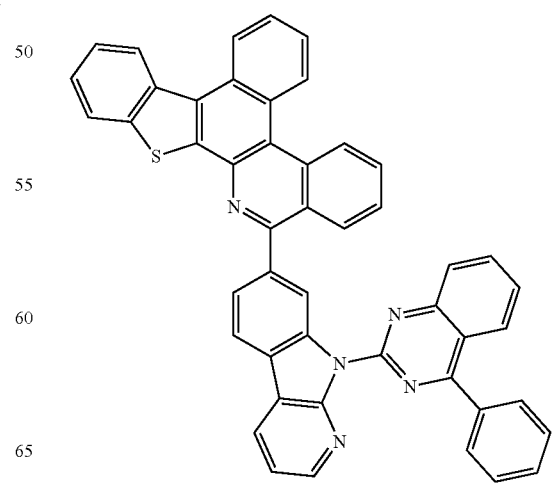

P-7-16
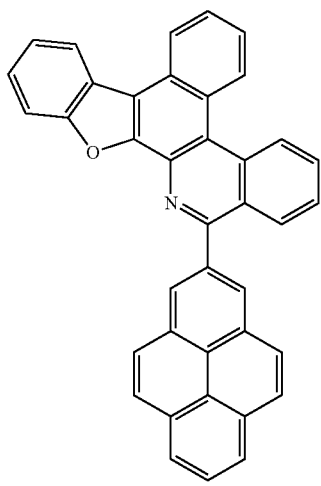
P-7-19
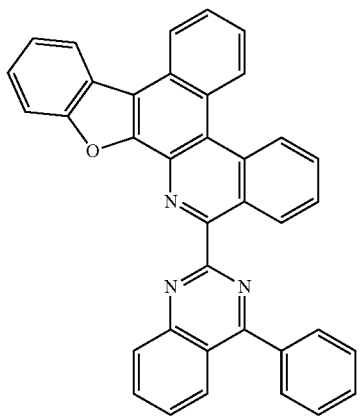
P-7-17
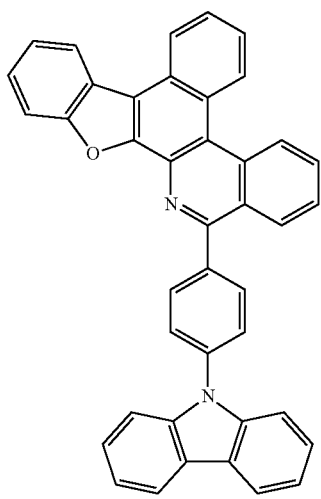
P-7-20
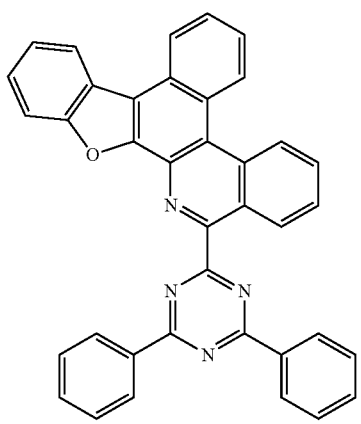
P-7-18
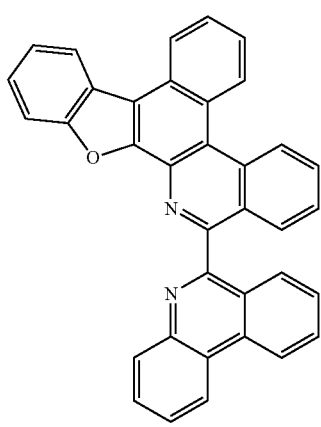
P-8-1
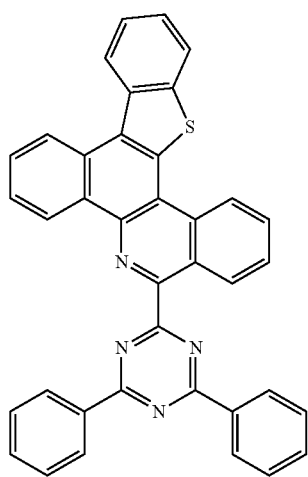

P-8-2
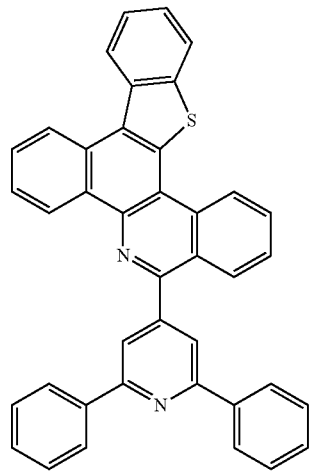
P-8-3
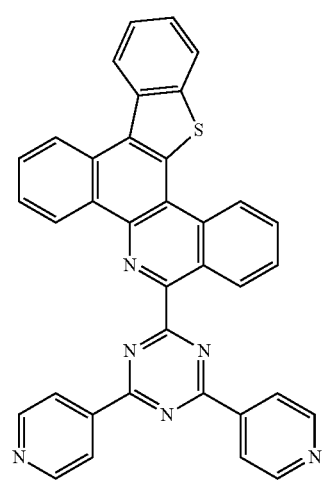
P-8-4
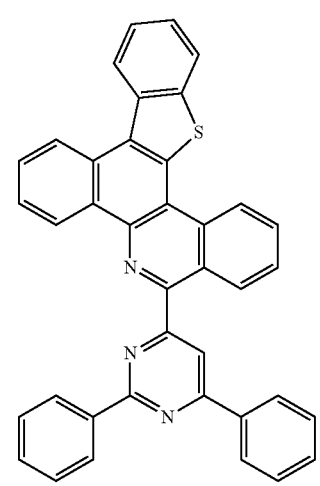
P-8-5
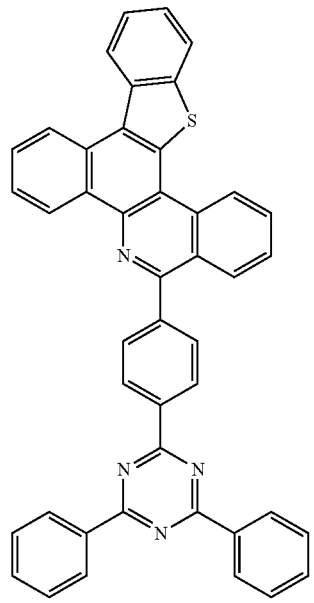
P-8-6
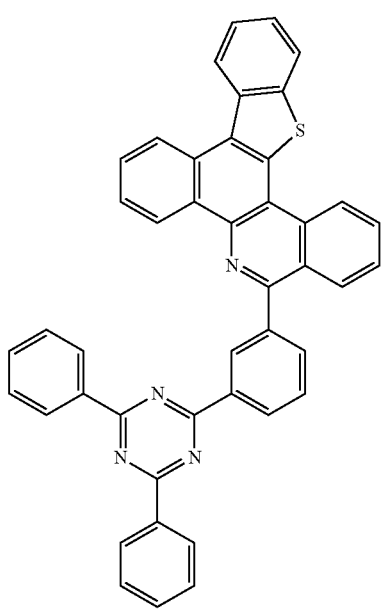

P-8-7
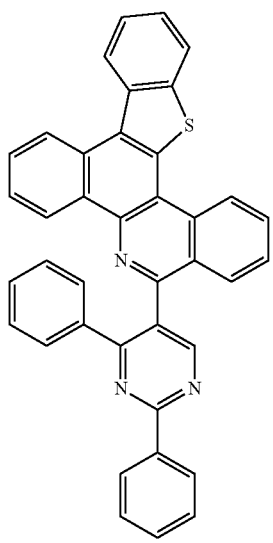
P-8-8
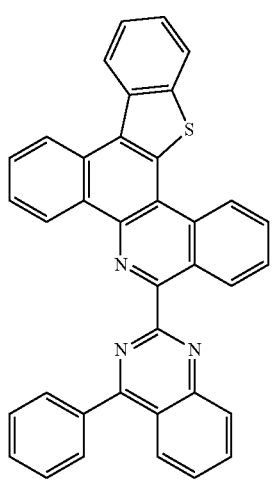
P-8-9
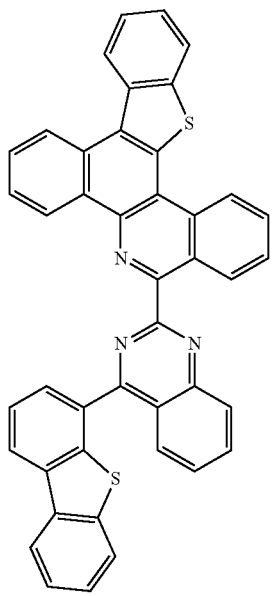
P-8-10
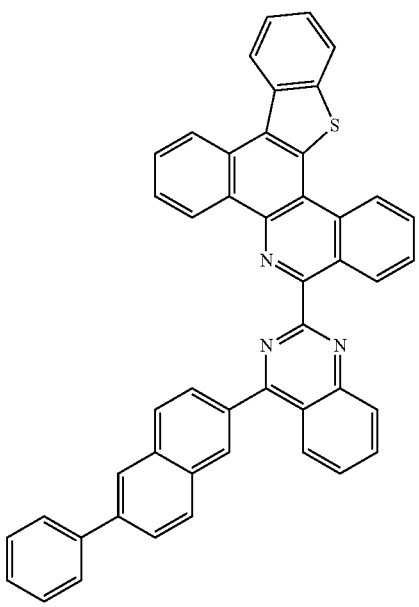
P-8-11
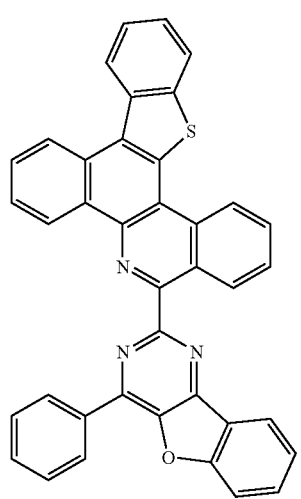
P-8-12
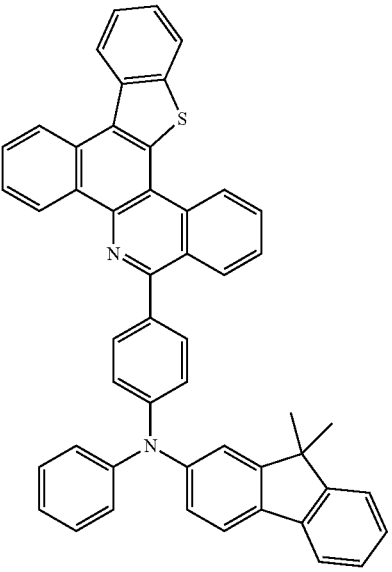

P-8-13
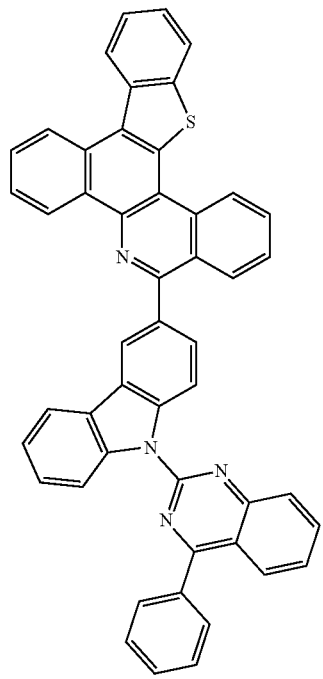
P-8-14
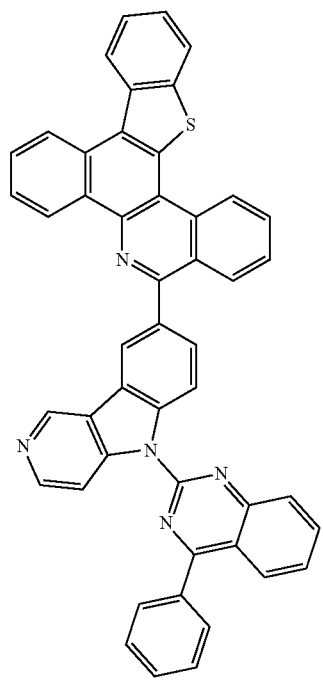
P-8-15
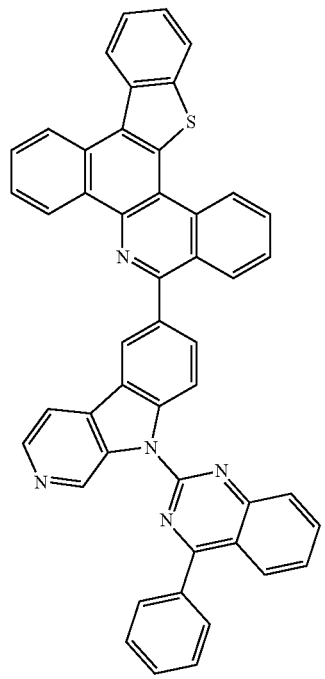
P-8-16
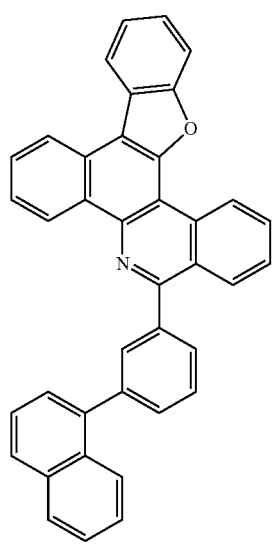

P-8-17
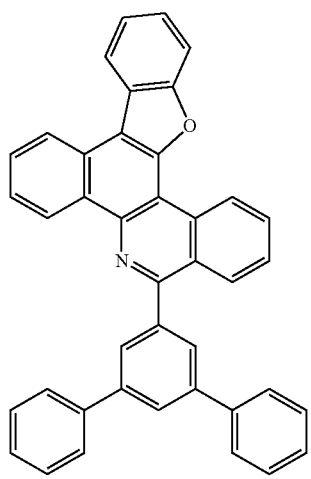
P-8-18
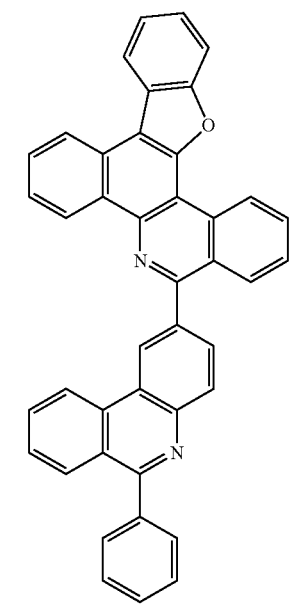
P-8-19
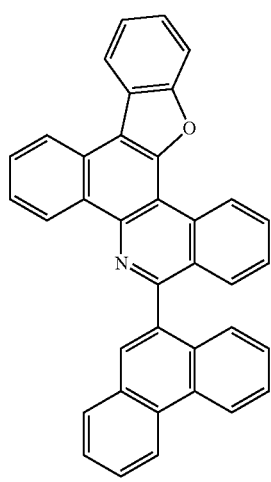
P-8-20
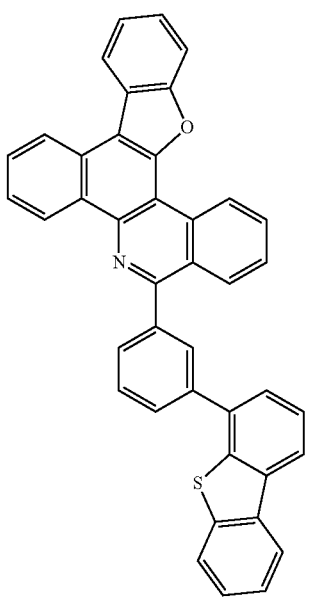
P-9-1
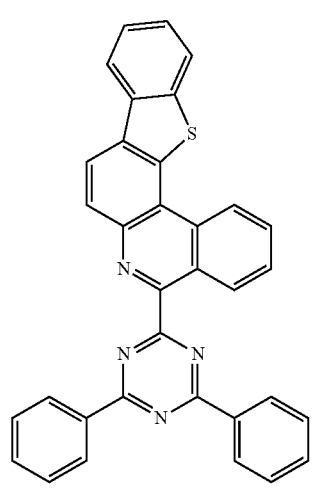
P-9-2
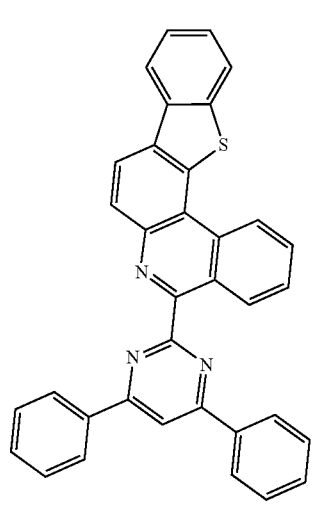

P-9-3
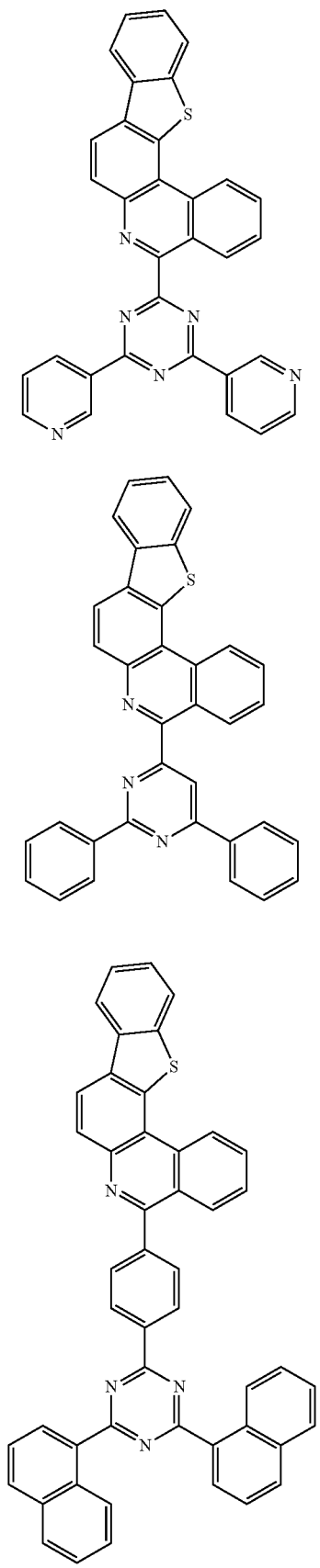
P-9-4
P-9-5
P-9-6
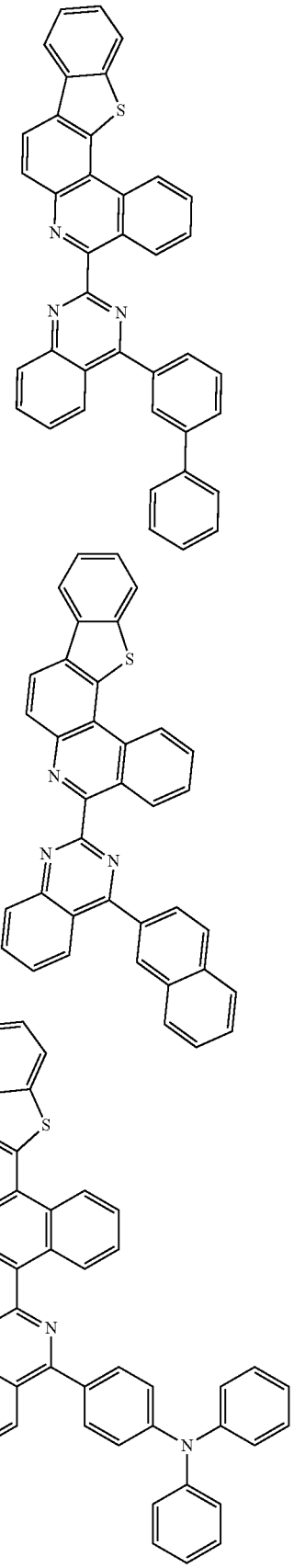
P-9-7
P-9-8

P-9-9
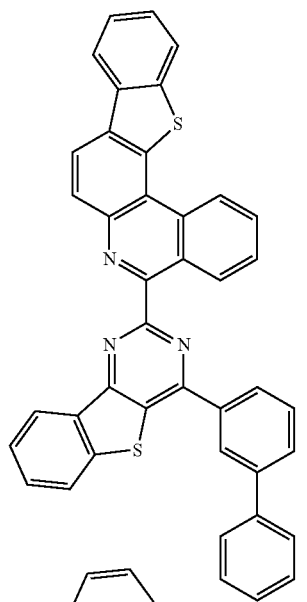
P-9-10
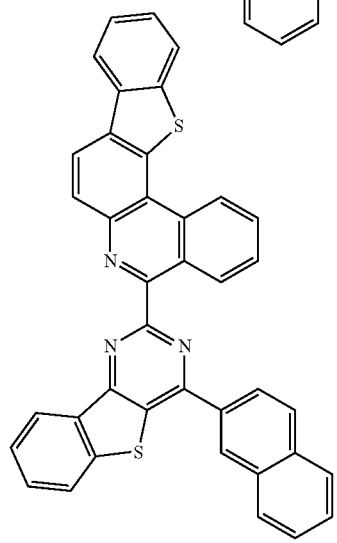
P-9-11
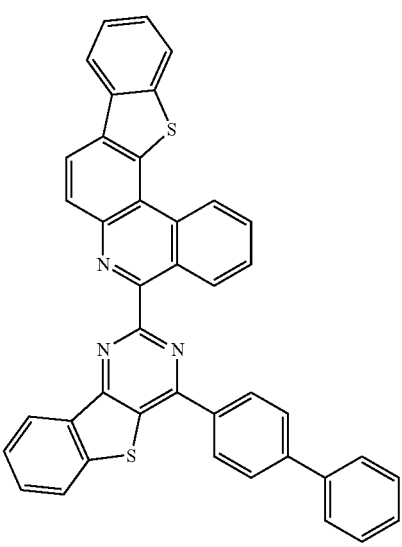
P-9-12
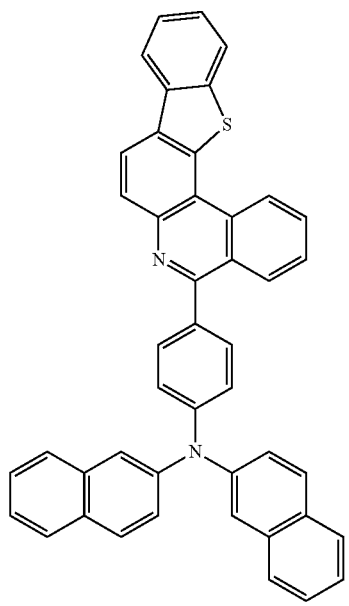
P-9-13
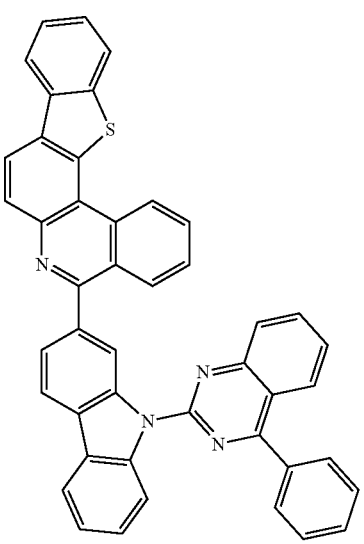
P-9-14
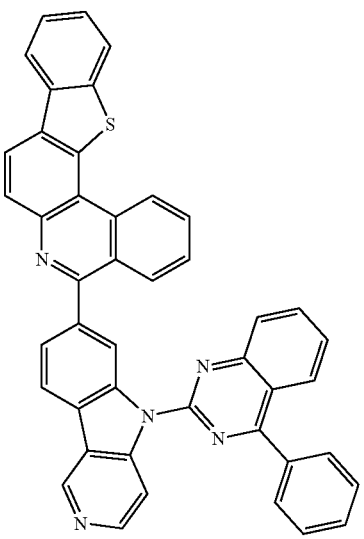

P-9-15
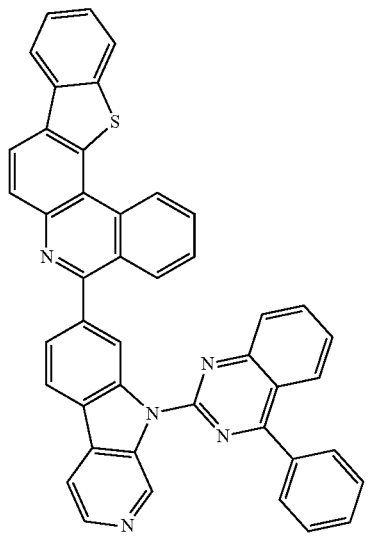
P-9-16
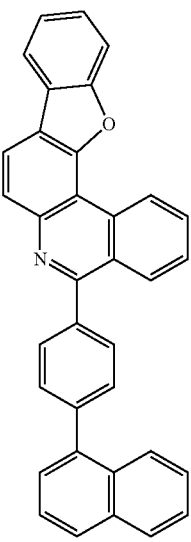
P-9-17
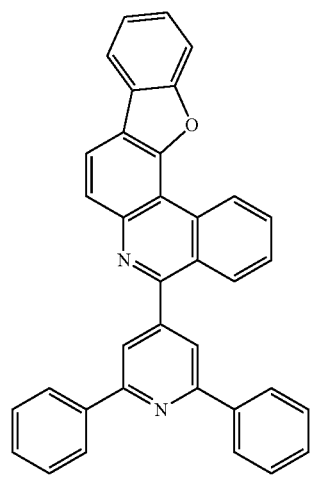
P-9-18
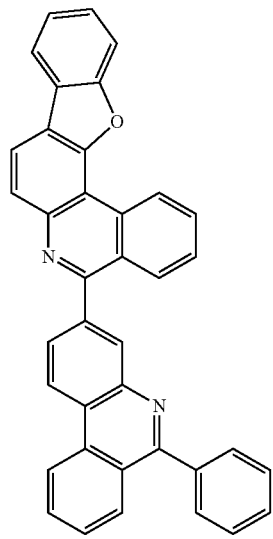
P-9-19
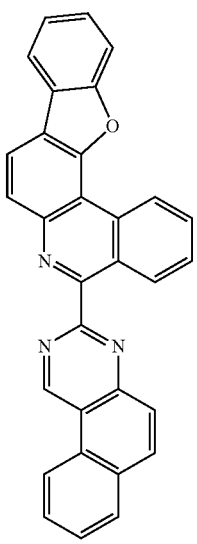
P-9-20
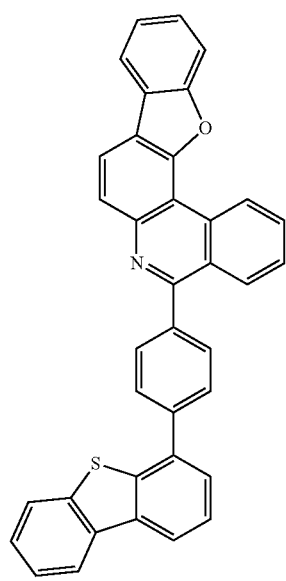

-continued
P-10-1
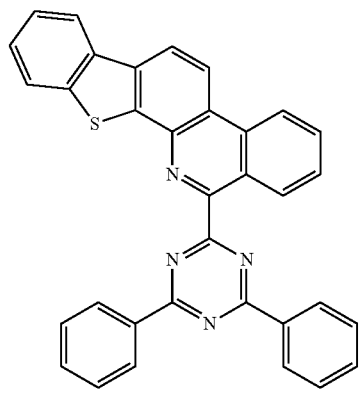
P-10-2
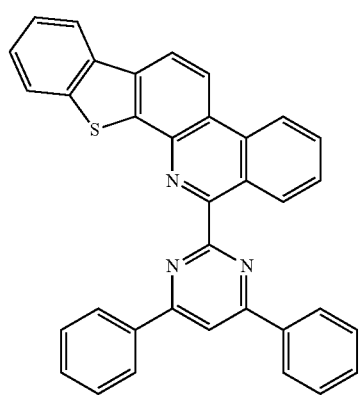
P-10-3
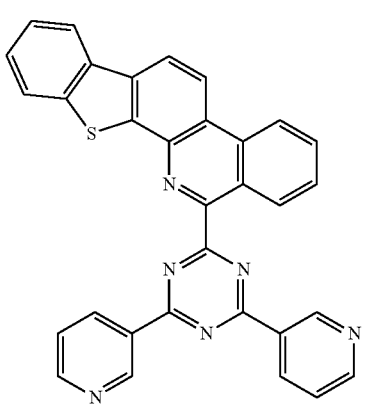
P-10-4
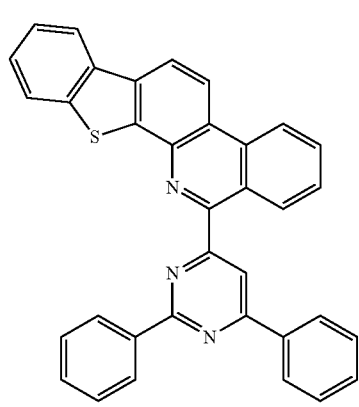
-continued
P-10-5
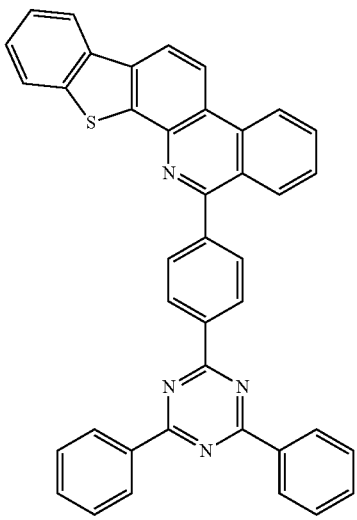
P-10-6
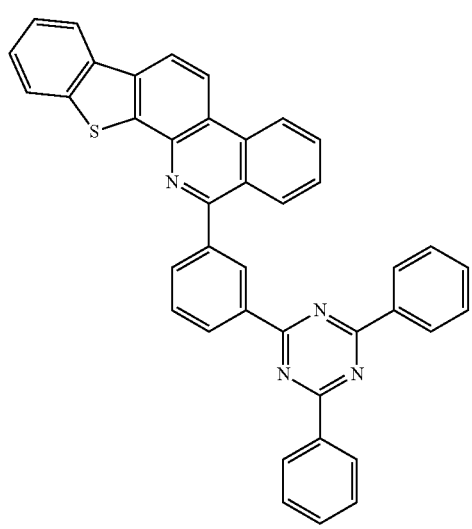
P-10-7
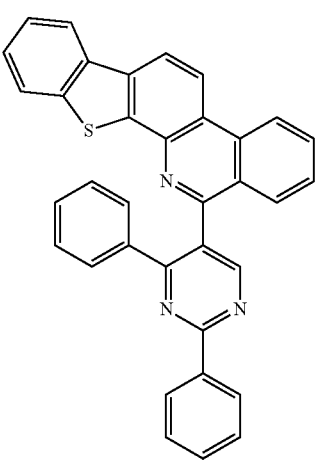

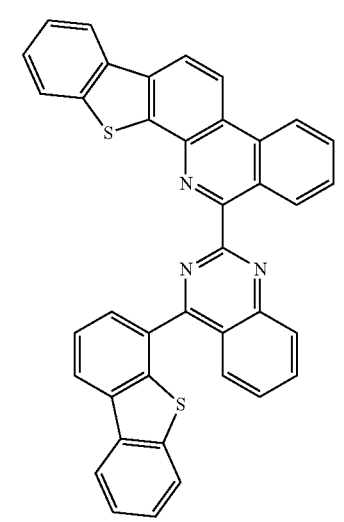
P-10-8
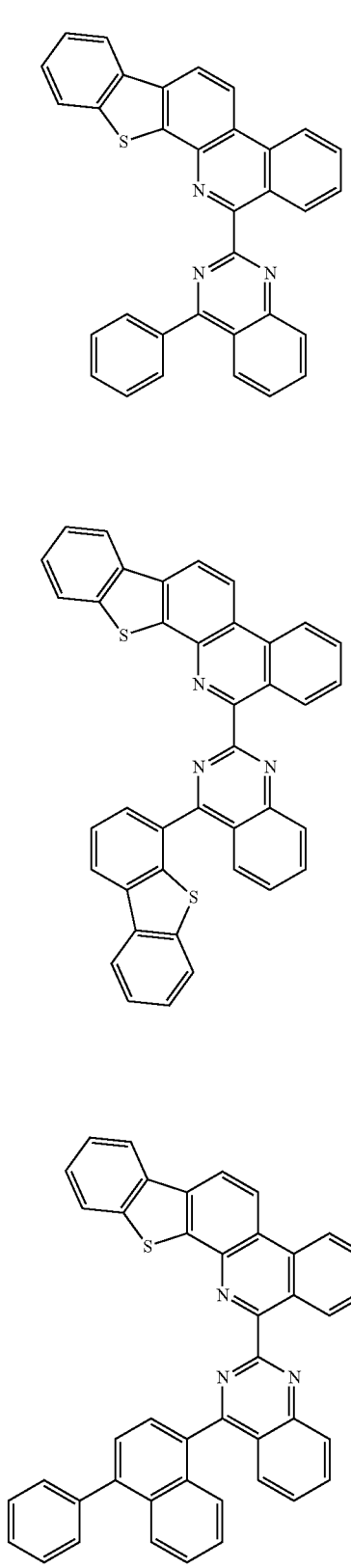
P-10-9
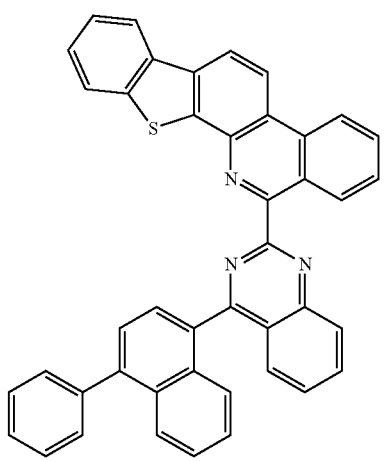
P-10-10
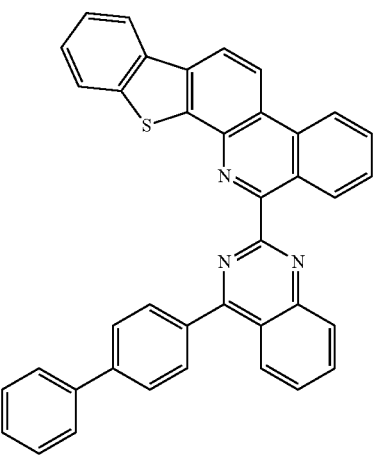
P-10-11
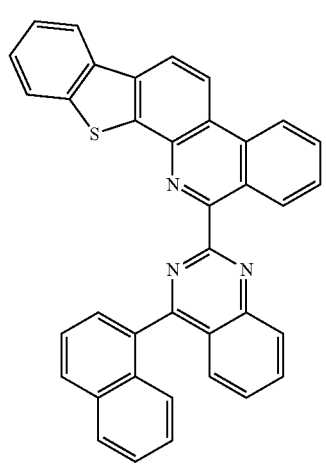
P-10-12
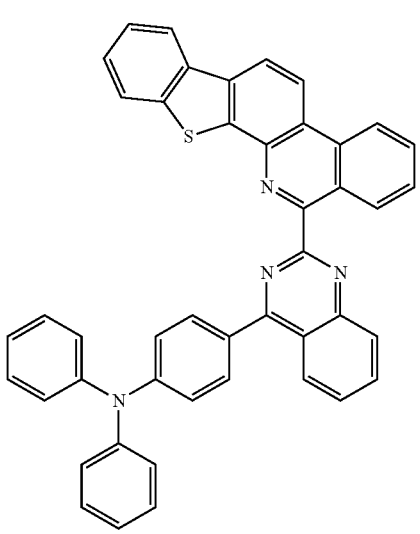
P-10-13

P-10-14
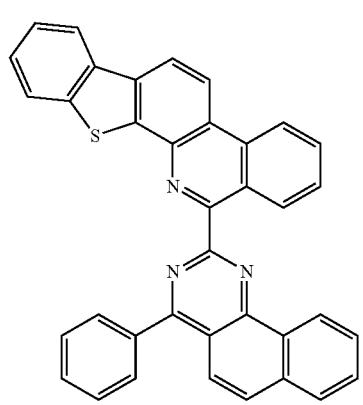
P-10-15
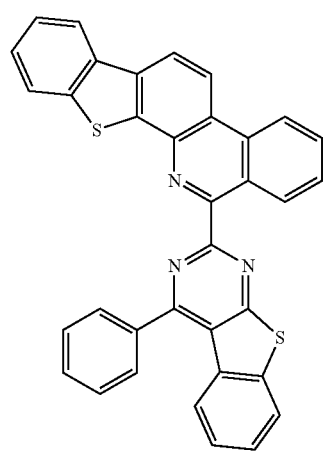
P-10-16
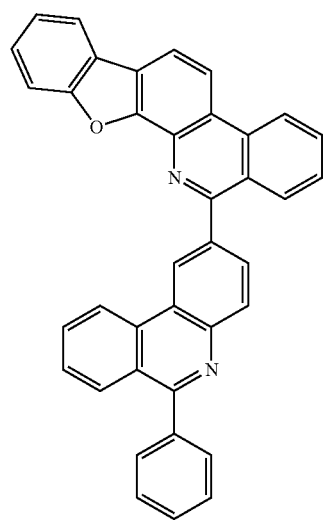
P-10-17
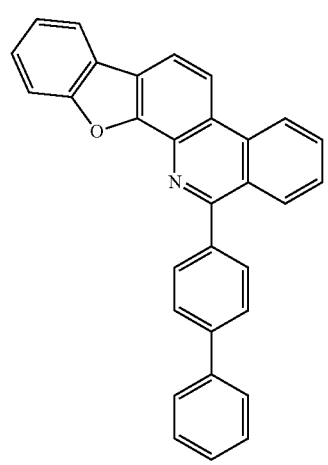
P-10-18
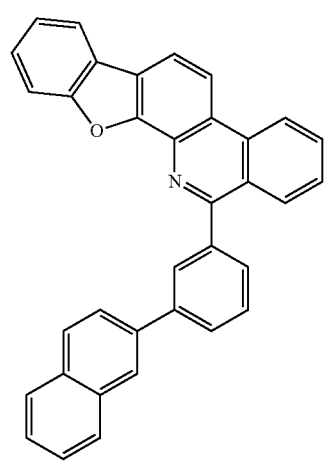
P-10-19
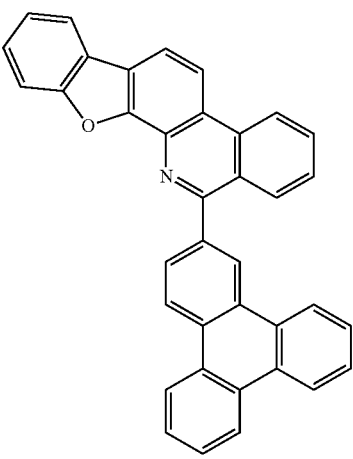

P-10-20

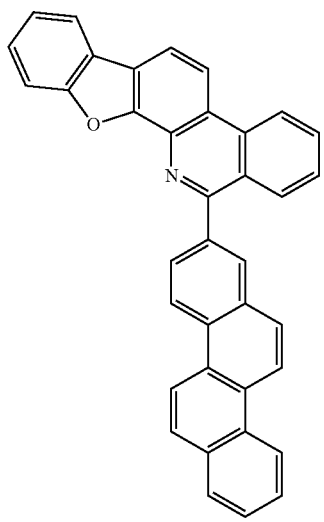

Ⓐ indicates text missing or illegible when filed

In accordance with an aspect of the present invention, the present invention provides a compound for the organic electric element represented by formula 1 above.

Herein, the organic electric element comprises a first electrode, a second electrode, and an organic material layer positioned between the first electrode and the organic material layer may comprise the compound represented by the formula 1. The compound represented by formula 1 may be contained in at least one layer of a hole injection layer, a hole transport layer, an emission-auxiliary layer and a light emitting layer. That is, the compound represented by formula 1 may be used as the material of a hole injection layer, a hole transport layer, an emission-auxiliary layer or a light emitting layer. Preferably, the compound represented by formula 1 may be used as a phosphorescent host of the light emitting layer.

Specifically, the present invention provides the organic electric element comprising the organic material layer, wherein the organic material layer comprises one of compounds represented by the formulas 5 to 10 or the formulas 1-1 to 1-4, specifically, the compound. Further, the compound comprised in the organic material layer may be a single compound or a mixture of two or more kinds. For example, a light emitting layer of the organic material layer may be formed by a single compound P-1-1, or a light emitting layer may comprise a mixture of P-1-1 and P-1-2

In another embodiment of the present invention, the present invention provides an organic electric element further including a layer for improving luminous efficiency, wherein the layer for improving luminous efficiency may be formed on at least one side of the first electrode and/or one side of the second electrode and at least one the side is not facing the organic material layer.

Hereinafter, Synthesis example of the compound represented by Formula 1 according to one embodiment of the present invention and manufacturing of an organic electric element will be described in detail by way of examples. However, the present invention is not limited to the following examples.

Synthesis Example

For example, the compound (final product) according to the present invention is synthesized by reacting Core and Sub 1, but there is no limitation thereto.

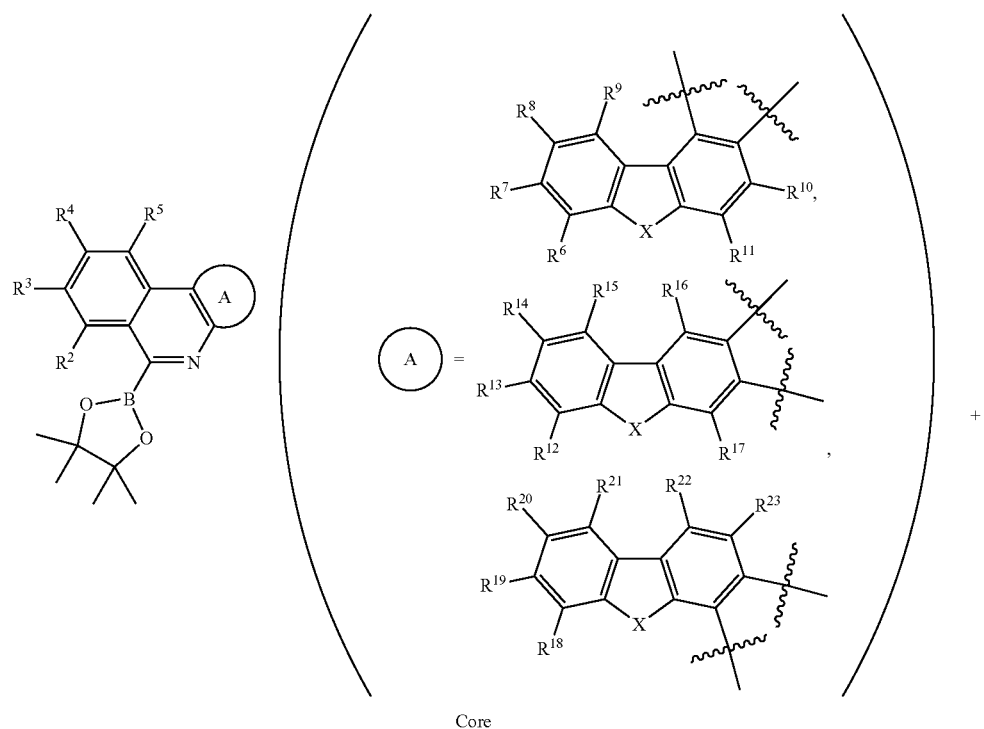

<Reaction Scheme 1> (Y : Br, Cl, I)

83  84
-continued
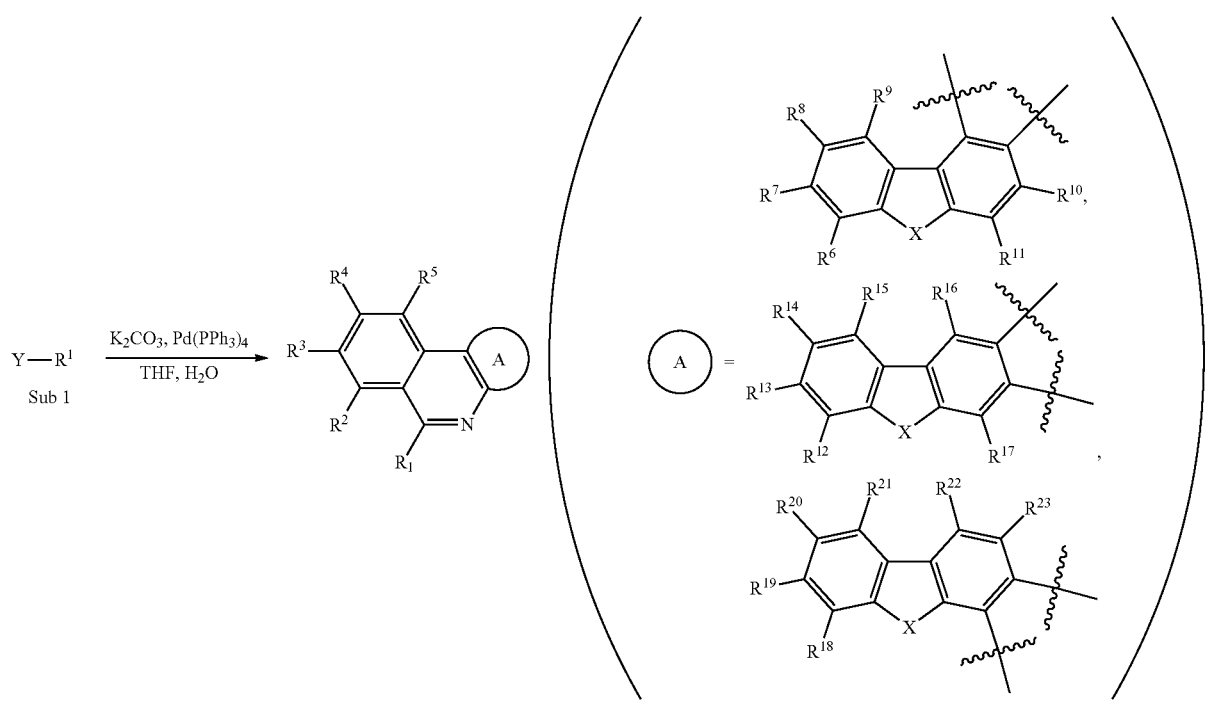
I. Synthesis of Core
1. Synthesis Example of Core 1
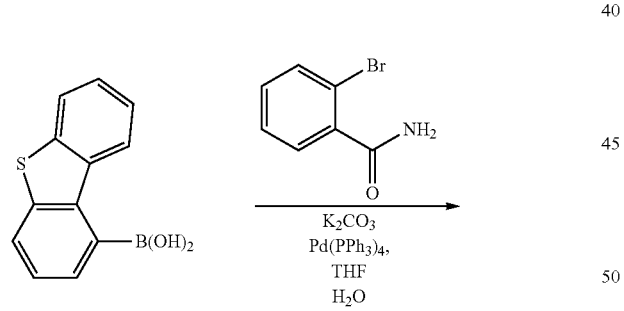
-continued
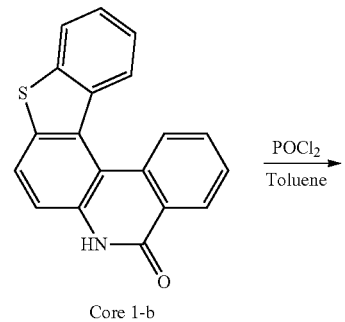
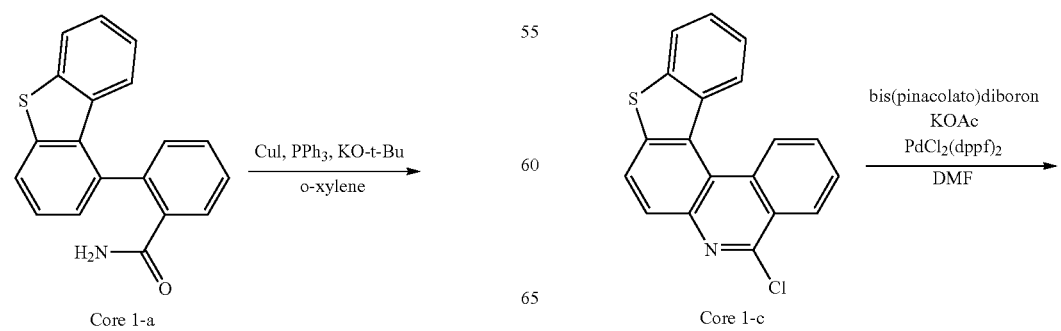

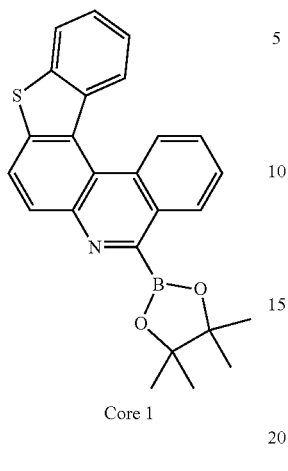

Core 1

Synthesis of Core 1-a 2-bromobenzamide (6.14 g, 30.69 mmol), Pd(PPh$_3$)$_4$ (1.06 g, 0.92 mmol), K$_2$CO$_3$ (12.73 g, 92.08 mmol), THF (100 ml) and H$_2$O (50 ml) were added to dibenzo[b,d]thiophen-1-ylboronic acid (7 g, 30.69 mmol), and then the mixture was refluxed at 90° C. for 6 hours. When the reaction was completed, the reaction product was cooled to room temperature. Then, the reaction product was extracted with ethyl acetate and was washed with water. The organic layer was dried with MgSO$_4$ and concentrated. Then, the concentrate was applied to silica gel column and recrystallized to obtain 6.98 g (yield: 75%) product.

Synthesis of Core 1-b

CuI (0.41 g, 2.14 mmol), PPh$_3$ (1.12 g, 4.29 mmol), potassium tert-butoxide (KO-tBu) (4.81 g, 42.85 mmol) and o-xylene (70 ml) were added to Core 1-a (6.5 g, 21.43 mmol), and then the mixture was refluxed at 120° C. for 18 hours. When the reaction was completed, the reaction product was cooled to room temperature. Then, the reaction product was extracted with ethyl acetate and was washed with water. The organic layer was dried with MgSO$_4$ and concentrated. Then, the concentrate was applied to silica gel column and recrystallized to obtain 5.81 g (yield: 90%) product.

Synthesis of Core 1-c

POCl$_3$ (3.36 g, 21.90 mmol), N,N-diisopropylethylamine (DIEA) (1.89 g, 14.60 mmol) and toluene (70 ml) were added to Core 1-b (5.5 g, 18.25 mmol)), and then the mixture was refluxed at 120° C. for 3 hours. When the reaction was completed, the reaction product was cooled to room temperature and ice water was added. Then, the mixture was extracted with ethyl acetate and washed with water. Then, the organic layer was dried with MgSO$_4$ and was filtered with celite filter. The obtained solid by removing solvent from the filtrate was recrystallized and filtered to obtain 4.55 g (yield: 70%) product.

Synthesis of Core 1

Bis(pinacolato)diboron (5.65 g, 20.17 mmol), PdCl$_2$(dppf)$_2$ (0.55 g, 0.67 mmol), KOAc (3.96 g, 40.34 mmol) and DMF (50 ml) were added to Core 1-c (4.3 g, 13.45 mmol), and then the mixture was refluxed at 120° C. for 6 hours. When the reaction was completed, the reaction product was cooled to room temperature. Then, the reaction product was extracted with MC and washed with water. Then, the organic layer was dried with MgSO$_4$ and concentrated. Then, the concentrate was applied to silica gel column and recrystallized to obtain 4.42 g (yield: 80%) product.

2. Synthesis Example of Core 2

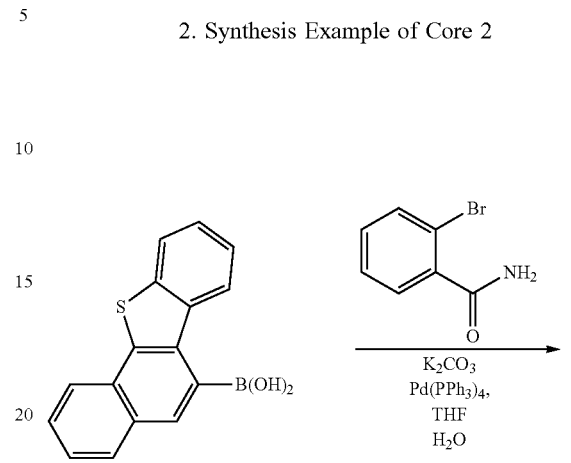

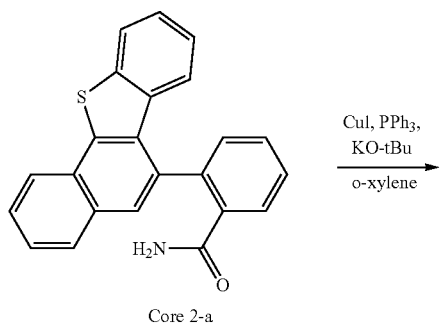

Core 2-a

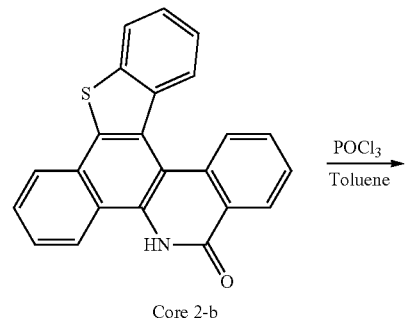

Core 2-b

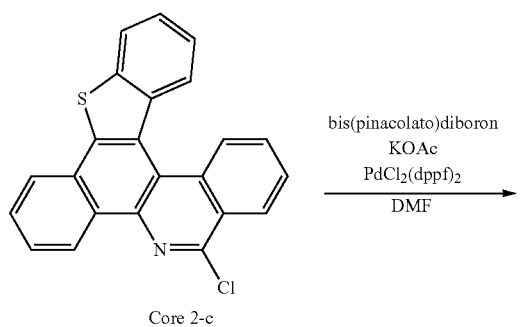

Core 2-c

-continued

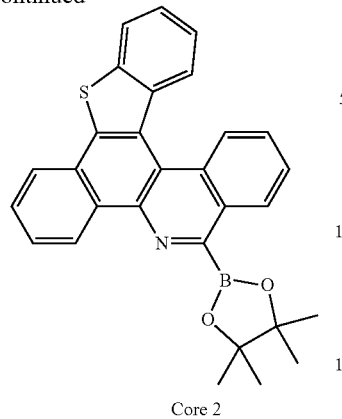

Core 2

Synthesis of Core 2-a 2-bromobenzamide (7.19 g, 35.96 mmol), Pd(PPh$_3$)$_4$ (1.25 g, 1.08 mmol), K$_2$CO$_3$ (14.91 g, 107.89 mmol), THF (100 ml) and H$_2$O (50 ml) were added to benzo[b]naphtho[2,1-d]thiophen-6-ylboronic acid (10 g, 35.96 mmol), and then 9.78 g (yield: 77%) of the product was obtained by the same method as in synthesis of Core 1-a.

Synthesis of Core 2-b

CuI (0.52 g, 2.74 mmol), PPh$_3$ (1.44 g, 5.49 mmol), potassium tert-butoxide (KO-tBu) (6.16 g, 54.89 mmol) and o-xylene (100 ml) were added to Core 2-a (9.7 g, 27.44 mmol), and then 8.87 g (yield: 92%) of the product was obtained by the same method as in synthesis of Core 1-b.

Synthesis of Core 2-c

POCl$_3$ (4.45 g, 29.03 mmol), N,N-diisopropylethylamine (DIEA) (2.50 g, 19.35 mmol) and toluene (80 ml) were added to Core 2-b (8.5 g, 24.19 mmol), and then 6.71 g (yield: 75%) of the product was obtained by the same method as in synthesis of Core 1-c.

Synthesis of Core 2

Bis(pinacolato)diboron (7.39 g, 26.36 mmol), PdCl$_2$(dppf)$_2$ (0.72 g, 0.88 mmol), KOAc (5.17 g, 52.72 mmol) and DMF (80 ml) were added to Core 2-c (6.5 g, 17.57 mmol), and then 6.65 g (yield: 82%) of the product was obtained by the same method as in synthesis of Core 1.

3. Synthesis Example of Core 3

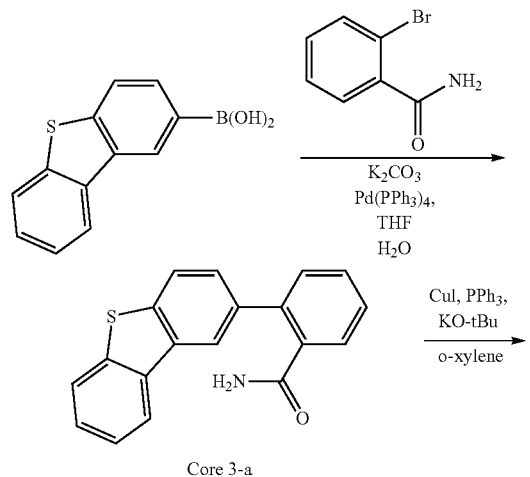

Core 3-a

-continued

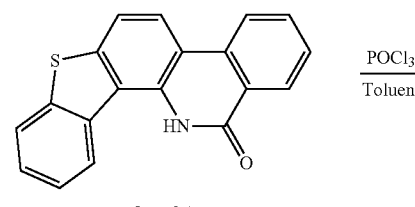

Core 3-b

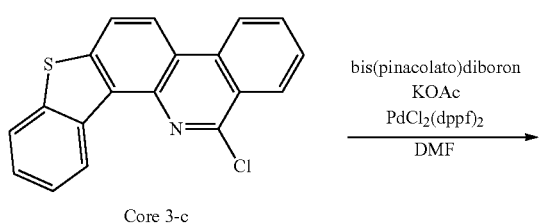

Core 3-c

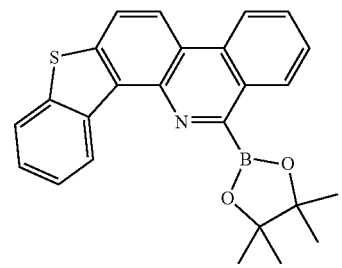

Core 3

Synthesis of Core 3-a 2-bromobenzamide (13.16 g, 65.77 mmol), Pd(PPh$_3$)$_4$ (2.28 g, 1.97 mmol), K$_2$CO$_3$ (27.27 g, 197.31 mmol), THF (200 ml) and H$_2$O (100 ml) were added to dibenzo[b,d]thiophen-2-ylboronic acid (15 g, 65.77 mmol), and then 16.16 g (yield: 81%) of the product was obtained by the same method as in synthesis of Core 1-a.

Synthesis of Core 3-b

CuI (1.00 g, 5.27 mmol), PPh$_3$ (2.77 g, 10.55 mmol), potassium tert-butoxide (KO-tBu) (11.84 g, 105.48 mmol) and o-xylene (200 ml) were added to Core 3-a (16 g, 52.74 mmol), and then 6.68 g (yield: 42%) of the product was obtained by the same method as in synthesis of Core 1-b.

Synthesis of Core 3-c

POCl$_3$ (3.97 g, 25.88 mmol), N,N-diisopropylethylamine (DIEA) (2.23 g, 17.26 mmol) and toluene (70 ml) were added to Core 3-b (6.5 g, 21.57 mmol), and then 5.04 g (yield: 73%) of the product was obtained by the same method as in synthesis of Core 1-c.

Synthesis of Core 3

Bis(pinacolato)diboron (6.57 g, 23.45 mmol), PdCl$_2$(dppf)$_2$ (0.64 g, 0.78 mmol), KOAc (4.60 g, 46.90 mmol) and DMF (80 ml) were added to Core 3-c (5 g, 15.63 mmol), and then 4.89 g (yield: 76%) of the product was obtained by the same method as in synthesis of Core 1.

4. Synthesis Example of Core 4

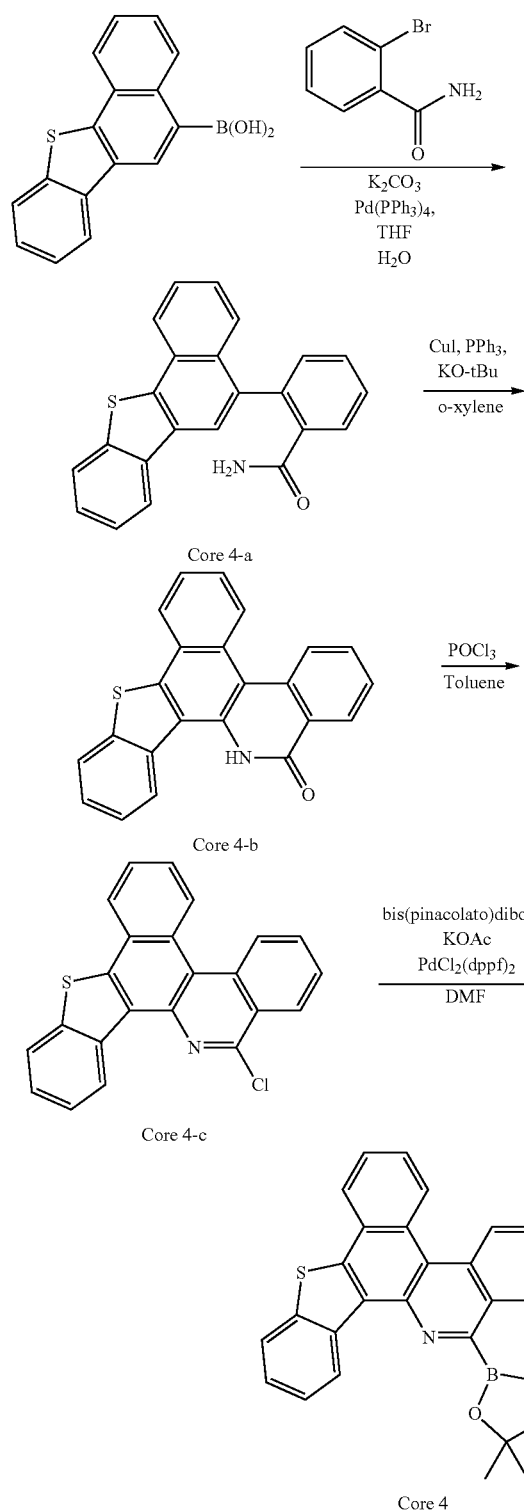

Synthesis of Core 4-a 2-bromobenzamide (8.63 g, 43.15 mmol), Pd(PPh3)4 (1.50 g, 1.29 mmol), K2CO3 (17.89 g, 129.44 mmol) and THF (150 ml), H2O (70 ml) were added to benzo[b]naphtho[2,1-d]thiophen-5-ylboronic acid (12 g, 43.15 mmol), and then 12.05 g (yield: 79%) of the product was obtained by the same method as in synthesis of Core 1-a.

Synthesis of Core 4-b

CuI (0.65 g, 3.40 mmol), PPh3 (1.78 g, 6.79 mmol), potassium tert-butoxide (KO-tBu) (7.62 g, 67.90 mmol) and o-xylene (150 ml) were added to Core 4-a (12 g, 34.95 mmol), and then 10.62 g (yield: 89%) of the product was obtained by the same method as in synthesis of Core 1-b.

Synthesis of Core 4-c

POCl3 (5.24 g, 34.15 mmol), N,N-diisopropylethylamine (DIEA) (2.94 g, 22.76 mmol) and toluene (100 ml) were added to Core 4-b (10 g, 28.46 mmol), and then 7.37 g (yield: 70%) of the product was obtained by the same method as in synthesis of Core 1-c.

Synthesis of Core 4

Bis(pinacolato)diboron (7.95 g, 28.39 mmol), PdCl2(dppf)2 (0.77 g, 0.95 mmol), KOAc (5.57 g, 56.78 mmol) and DMF (100 ml) were added to Core 4-c (7 g, 18.93 mmol), and then 6.55 g (yield: 75%) of the product was obtained by the same method as in synthesis of Core 1.

5. Synthesis Example of Core 5

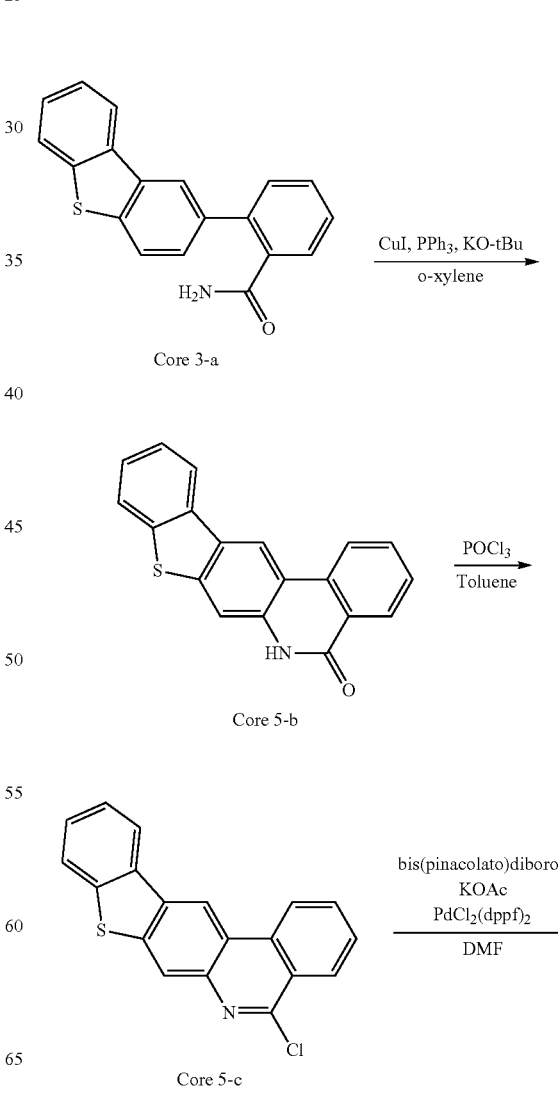

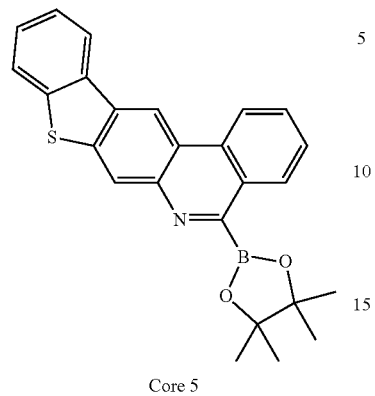

Core 5

Synthesis of Core 5-b

CuI (0.56 g, 2.97 mmol), PPh₃ (1.56 g, 5.93 mmol), potassium tert-butoxide (KO-tBu) (6.66 g, 59.33 mmol) and o-xylene (100 ml) were added to Core 3-a (9 g, 29.67 mmol), and then 3.84 g (yield: 43%) of the product was obtained by the same method as in synthesis of Core 1-b.

Synthesis of Core 5-c

POCl₃ (2.26 g, 14.73 mmol), N,N-diisopropylethylamine (DIEA) (1.27 g, 9.82 mmol) and toluene (50 ml) were added to Core 5-b (3.7 g, 12.28 mmol), and then 2.83 g (yield: 72%) of the product was obtained by the same method as in synthesis of Core 1-c.

Synthesis of Core 5

Bis(pinacolato)diboron (5.78 g, 20.64 mmol), PdCl₂(dppf)₂ (0.56 g, 0.69 mmol), KOAc (4.05 g, 41.27 mmol) and DMF (60 ml) were added to Core 5-c (4.4 g, 13.76 mmol), and then 4.7 g (yield: 83%) of the product was obtained by the same method as in synthesis of Core 1.

6. Synthesis Example of Core 6

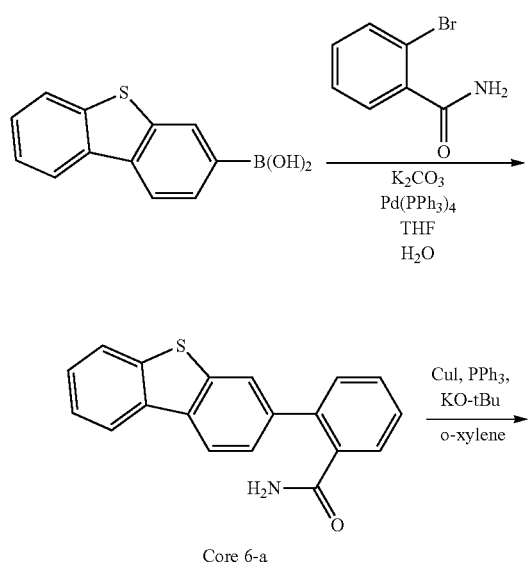

Core 6-a

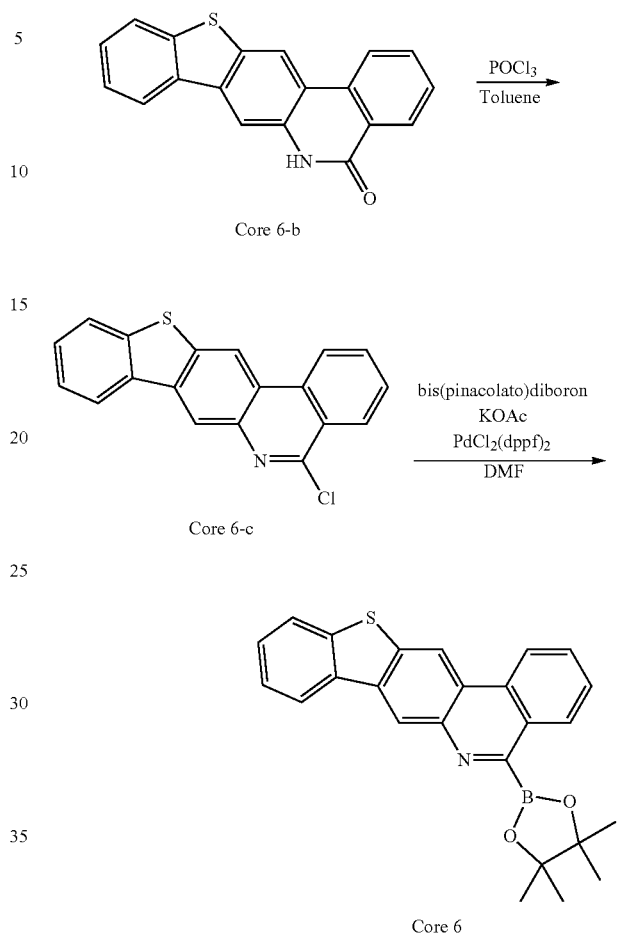

Synthesis of Core 6-a 2-bromobenzamide (21.93 g, 109.62 mmol), Pd(PPh₃)₄ (3.80 g, 3.29 mmol), K₂CO₃ (45.45 g, 328.85 mmol), THF (300 ml) and H₂O (150 ml) were added to dibenzo[b,d]thiophen-3-ylboronic acid (25 g, 109.62 mmol), and then 29.26 g (yield: 88%) of the product was obtained by the same method as in synthesis of Core 1-a.

Synthesis of Core 6-b

CuI (1.82 g, 9.56 mmol), PPh₃ (5.01 g, 19.12 mmol), potassium tert-butoxide (KO-tBu) (21.45 g, 191.18 mmol) and o-xylene (300 ml) were added to Core 6-a (29 g, 95.59 mmol), and then 10.95 g (yield: 38%) of the product was obtained by the same method as in synthesis of Core 1-b.

Synthesis of Core 6-c

POCl₃ (6.47 g, 42.21 mmol), N,N-diisopropylethylamine (DIEA) (3.64 g, 28.14 mmol) and toluene (110 ml) were added to Core 6-b (10.6 g, 35.17 mmol), and then 7.65 g (yield: 68%) of the product was obtained by the same method as in synthesis of Core 1-c.

Synthesis of Core 6

Bis(pinacolato)diboron (10.12 g, 36.12 mmol), PdCl₂(dppf)₂ (0.98 g, 1.20 mmol), KOAc (7.09 g, 72.23 mmol) and DMF (100 ml) were added to Core 6-c (7.7 g, 24.08 mmol), and then 8.42 g (yield: 85%) of the product was obtained by the same method as in synthesis of Core 1.

7. Synthesis Example of Core 7

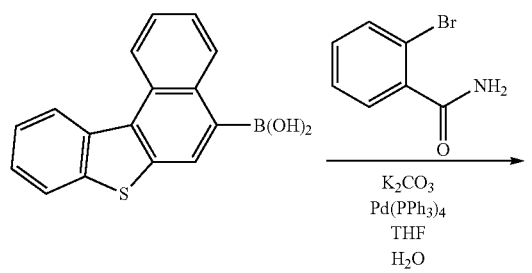

Core 7-a

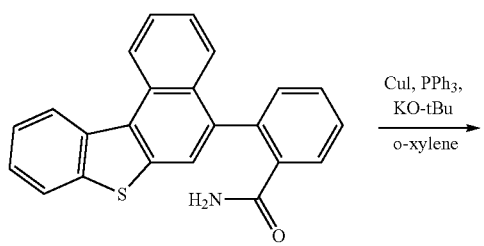

Core 7-b

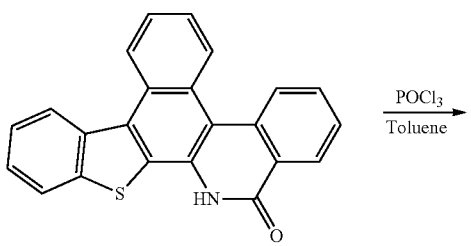

Core 7-c

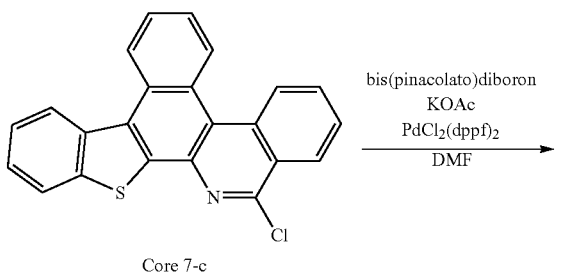

Core 7

Synthesis of Core 7-a 2-bromobenzamide (12.23 g, 61.12 mmol), Pd(PPh₃)₄ (2.12 g, 1.83 mmol), K₂CO₃ (25.34 g, 183.37 mmol), THF (200 ml) and H₂O (100 ml) were added to benzo[b]naphtho[1,2-d]thiophen-5-ylboronic acid (17 g, 61.12 mmol), and then 19.87 g (yield: 92%) of the product was obtained by the same method as in synthesis of Core 1-a.

Synthesis of Core 7-b

CuI (1.02 g, 5.38 mmol), PPh₃ (2.82 g, 10.75 mmol), potassium tert-butoxide (KO-tBu) (12.06 g, 107.51 mmol) and o-xylene (200 ml) were added to Core 7-a (19 g, 53.76 mmol), and then 17.57 g (yield: 93%) of the product was obtained by the same method as in synthesis of Core 1-b.

Synthesis of Core 7-c

POCl₃ (6.81 g, 44.39 mmol), N,N-diisopropylethylamine (DIEA) (3.83 g, 29.59 mmol) and toluene (150 ml) were added to Core 7-b (13 g, 36.99 mmol), and then 8.89 g (yield: 65%) of the product was obtained by the same method as in synthesis of Core 1-c.

Synthesis of Core 7

Bis(pinacolato)diboron (10.00 g, 35.69 mmol), PdCl₂(dppf)₂ (0.97 g, 1.19 mmol), KOAc (7.00 g, 71.38 mmol) and DMF (100 ml) were added to Core 7-c (8.8 g, 23.79 mmol), and then 9.66 g (yield: 88%) of the product was obtained by the same method as in synthesis of Core 1.

8. Synthesis Example of Core 8

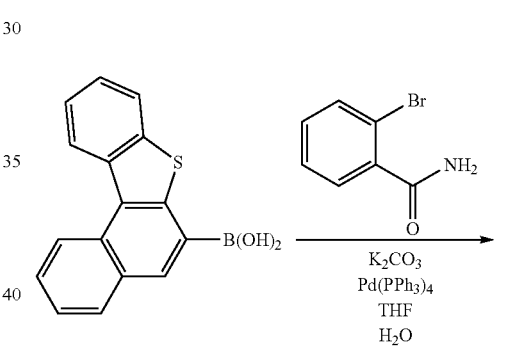

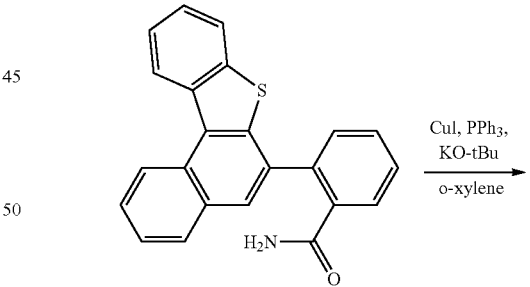

Core 8-a

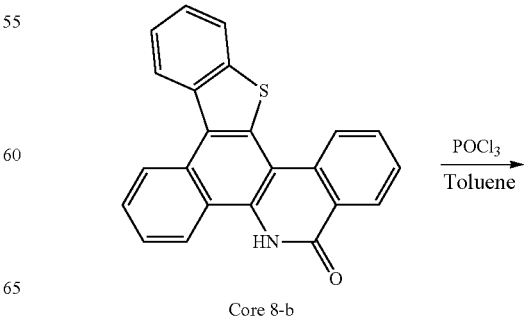

Core 8-b

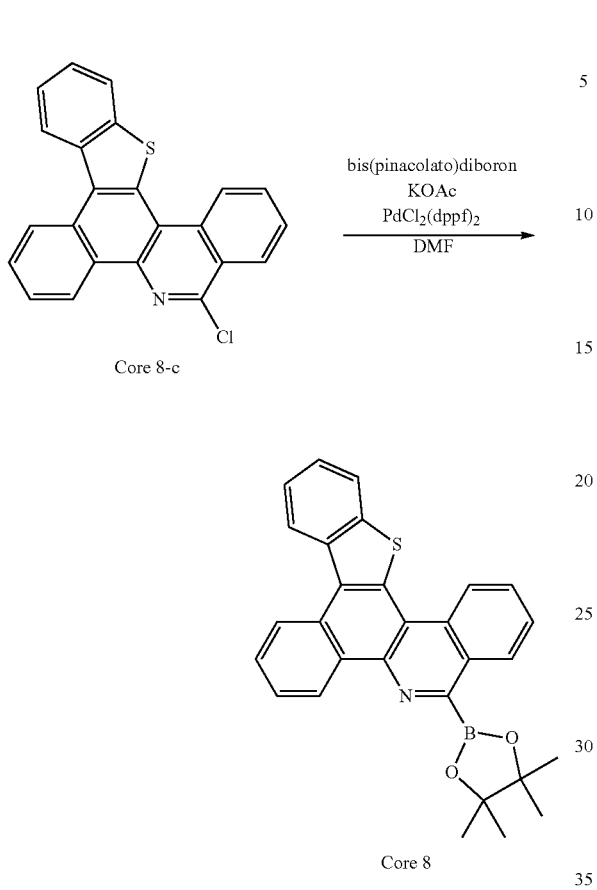

Synthesis of Core 8-a 2-bromobenzamide (10.07 g, 50.34 mmol), Pd(PPh$_3$)$_4$ (1.74 g, 1.51 mmol), K$_2$CO$_3$ (20.87 g, 151.01 mmol), THF (200 ml) and H$_2$O (100 ml) were added to benzo[b]naphtho[1,2-d]thiophen-6-ylboronic acid (14 g, 50.34 mmol), and then 15.66 g (yield: 88%) of the product was obtained by the same method as in synthesis of Core 1-a.

Synthesis of Core 8-b

CuI (0.81 g, 4.24 mmol), PPh$_3$ (2.23 g, 8.49 mmol), potassium tert-butoxide (KO-tBu) (9.52 g, 84.88 mmol) and o-xylene (200 ml) were added to Core 8-a (15 g, 42.44 mmol), and then 12.68 g (yield: 85%) of the product was obtained by the same method as in synthesis of Core 1-b.

Synthesis of Core 8-c

POCl$_3$ (6.28 g, 40.98 mmol), N,N-diisopropylethylamine (DIEA) (3.53 g, 27.32 mmol) and toluene (150 ml) were added to Core 8-b (12 g, 34.15 mmol), and then 8.46 g (yield: 67%) of the product was obtained by the same method as in synthesis of Core 1-c.

Synthesis of Core 8

Bis(pinacolato)diboron (9.32 g, 33.25 mmol), PdCl$_2$(dppf)$_2$ (0.91 g, 1.11 mmol), KOAc (6.53 g, 66.51 mmol) and DMF (100 ml) were added to Core 8-c (8.2 g, 22.17 mmol), and then 9 g (yield: 88%) of the product was obtained by the same method as in synthesis of Core 1.

9. Synthesis Example of Core 9

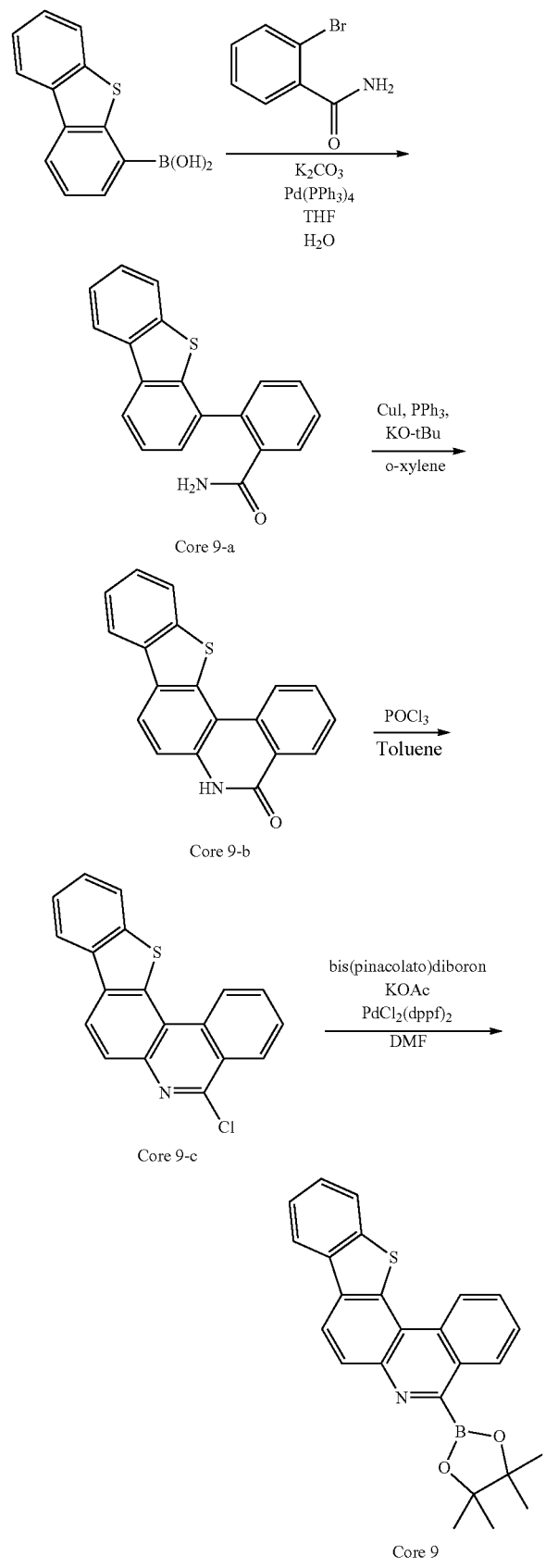

Synthesis of Core 9-a 2-bromobenzamide (6.75 g, 33.76 mmol), Pd(PPh$_3$)$_4$ (1.17 g, 1.01 mmol), K$_2$CO$_3$ (14.00 g, 101.28 mmol), THF (100 ml) and H$_2$O (50 ml) were added to dibenzo[b,d]thiophen-4-ylboronic acid (7.7 g, 33.76 mmol), and then 8.5 g (yield: 83%) of the product was obtained by the same method as in synthesis of Core 1-a.

Synthesis of Core 9-b

CuI (0.51 g, 2.67 mmol), PPh$_3$ (1.40 g, 5.34 mmol), potassium tert-butoxide (KO-tBu) (5.99 g, 53.40 mmol) and o-xylene (100 ml) were added to Core 9-a (8.1 g, 26.70 mmol), and then 7 g (yield: 87%) of the product was obtained by the same method as in synthesis of Core 1-b.

Synthesis of Core 9-c

POCl$_3$ (5.49 g, 35.84 mmol), N,N-diisopropylethylamine (DIEA) (3.09 g, 23.89 mmol) and toluene (100 ml) were added to Core 9-b (9 g, 29.86 mmol), and then 7.35 g (yield: 77%) of the product was obtained by the same method as in synthesis of Core 1-c.

Synthesis of Core 9

Bis(pinacolato)diboron (9.33 g, 33.30 mmol), PdCl$_2$(dppf)$_2$ (0.91 g, 1.11 mmol), KOAc (6.54 g, 66.60 mmol) and DMF (90 ml) were added to Core 9-c (7.1 g, 22.20 mmol), and then 7.4 g (yield: 81%) of the product was obtained by the same method as in synthesis of Core 1.

10. Synthesis Example of Core 10

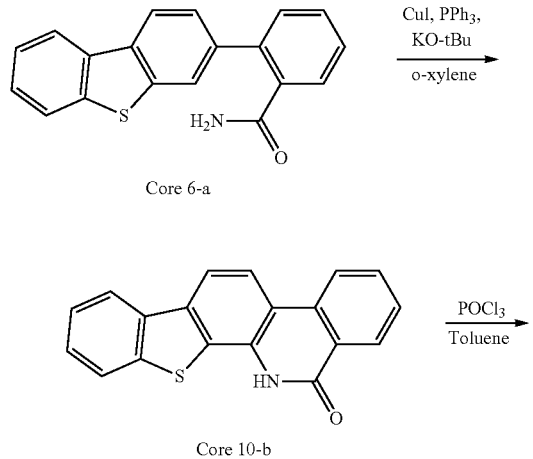

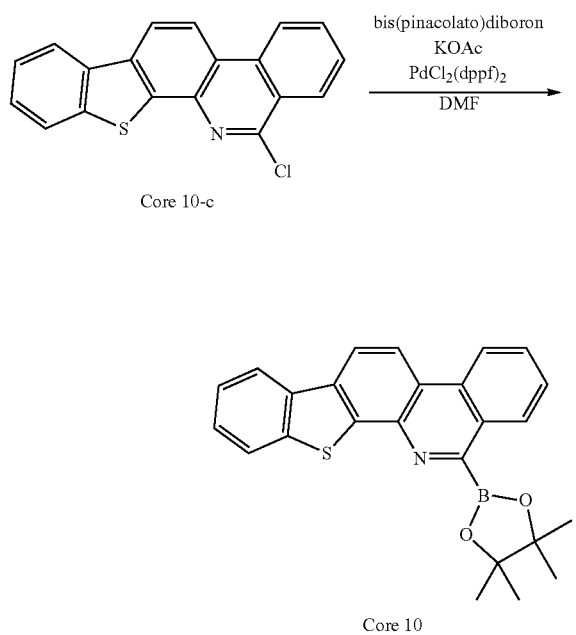

Synthesis of Core 10-b

CuI (1.44 g, 7.58 mmol), PPh$_3$ (4.98 g, 15.16 mmol), potassium tert-butoxide (KO-tBu) (17.01 g, 151.63 mmol) and o-xylene (250 ml) were added to Core 6-a (23 g, 75.81 mmol), and then 9.14 g (yield: 40%) of the product was obtained by the same method as in synthesis of Core 1-b.

Synthesis of Core 10-c

POCl$_3$ (5.43 g, 35.44 mmol), N,N-diisopropylethylamine (DIEA) (3.05 g, 23.63 mmol) and toluene (100 ml) were added to Core 10-b (8.9 g, 29.53 mmol), and then 6.99 g (yield: 74%) of the product was obtained by the same method as in synthesis of Core 1-c.

Synthesis of Core 10

Bis(pinacolato)diboron (7.88 g, 28.14 mmol), PdCl$_2$(dppf)$_2$ (0.77 g, 0.94 mmol), KOAc (5.52 g, 56.28 mmol) and DMF (100 ml) were added to Core 10-c (6 g, 18.76 mmol), and then 6.64 g (yield: 86%) of the product was obtained by the same method as in synthesis of Core 1.

TABLE 1

| compound | FD-MS | compound | FD-MS |
|---|---|---|---|
| Core 1 | m/z = 411.15(C$_{25}$H$_{22}$BNO$_2$S = 411.33) | Core 2 | m/z = 461.16(C$_{29}$H$_{24}$BNO$_2$S = 461.39) |
| Core 3 | m/z = 411.15(C$_{25}$H$_{22}$BNO$_2$S = 411.33) | Core 4 | m/z = 461.16(C$_{29}$H$_{24}$BNO$_2$S = 461.39) |
| Core 5 | m/z = 411.15(C$_{25}$H$_{22}$BNO$_2$S = 411.33) | Core 6 | m/z = 411.15(C$_{25}$H$_{22}$BNO$_2$S = 411.33) |
| Core 7 | m/z = 461.16(C$_{29}$H$_{24}$BNO$_2$S = 461.39) | Core 8 | m/z = 461.16(C$_{29}$H$_{24}$BNO$_2$S = 461.39) |
| Core 9 | m/z = 411.15(C$_{25}$H$_{22}$BNO$_2$S = 411.33) | Core 10 | m/z = 411.15(C$_{25}$H$_{22}$BNO$_2$S = 411.33) |

II. Example of Sub 1
The compound belonging to Sub 1 may be the following compounds but there is no limitation thereto. Table 2 shows FD-MS (Field Desorption-Mass Spectrometry) values of compounds belonging to Sub 1.
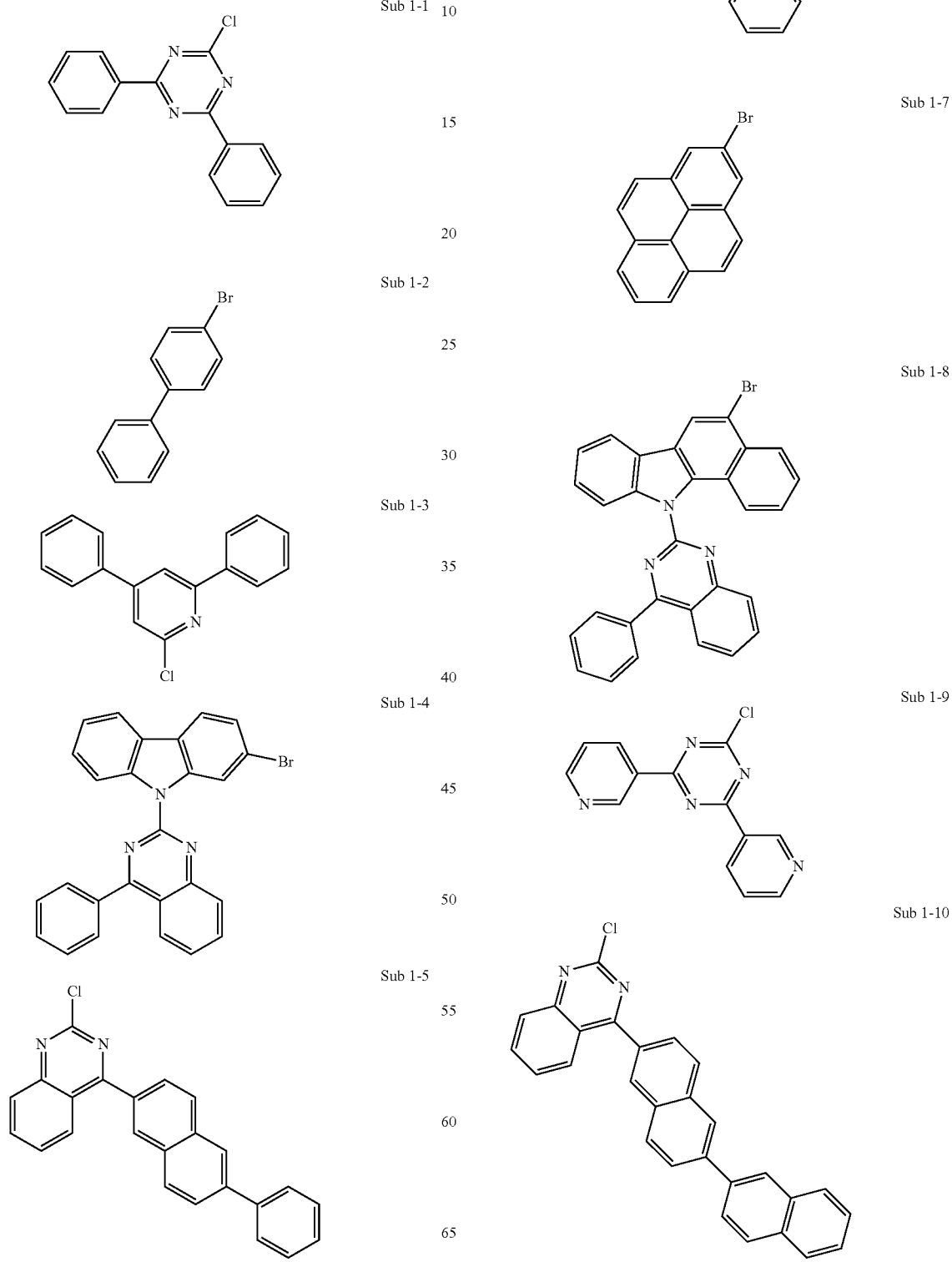

Sub 1-11
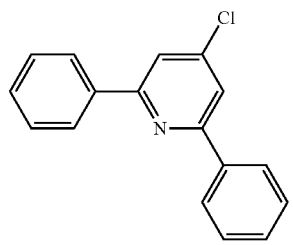
Sub 1-12
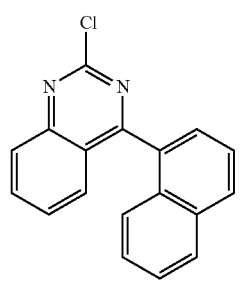
Sub 1-13
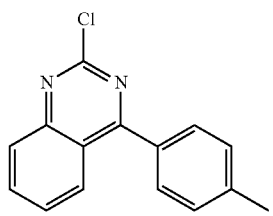
Sub 1-14
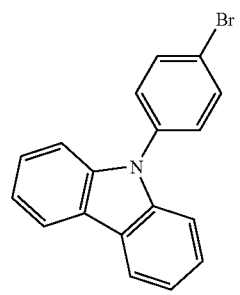
Sub 1-15
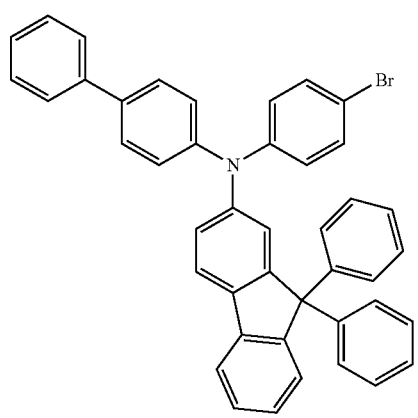
Sub 1-16
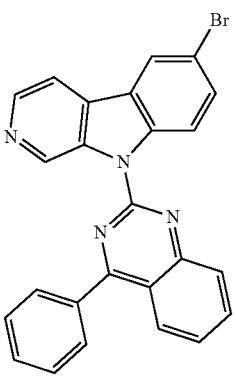
Sub 1-17
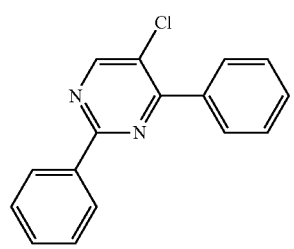
Sub 1-18
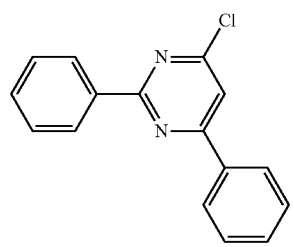
Sub 1-19
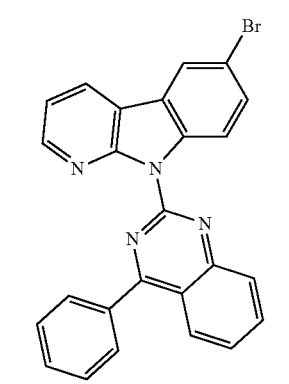
Sub 1-20
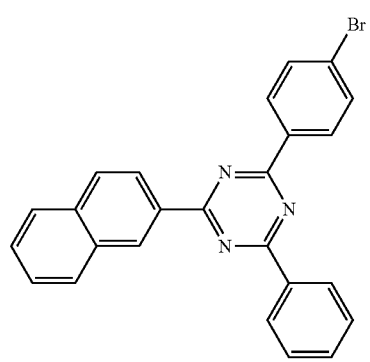

Sub 1-21
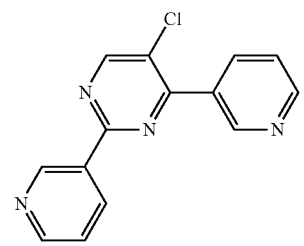
Sub 1-22
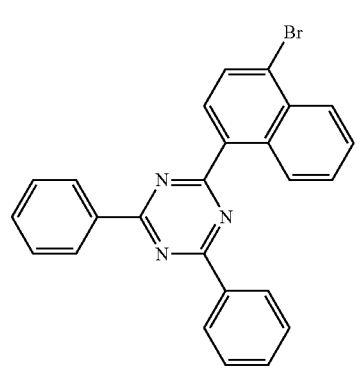
Sub 1-23
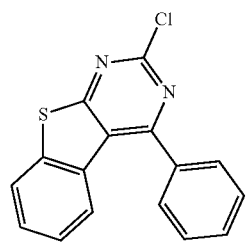
Sub 1-24
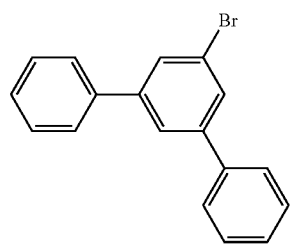
Sub 1-25
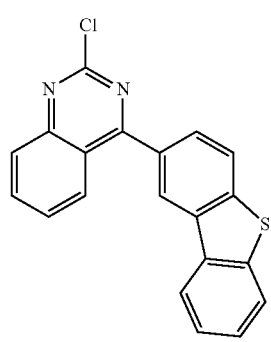
Sub 1-26
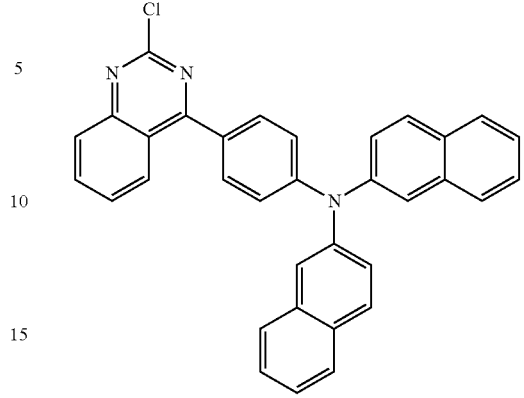
Sub 1-27
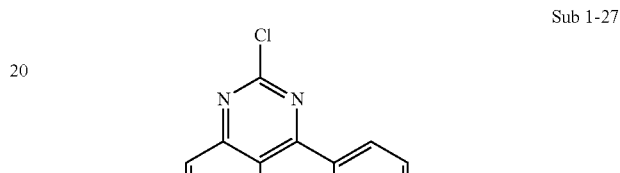
Sub 1-28
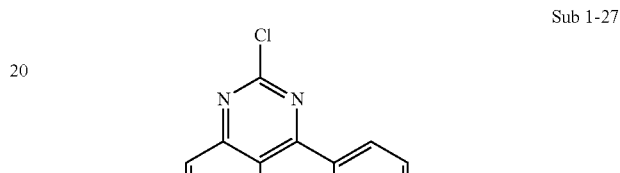
Sub 1-29
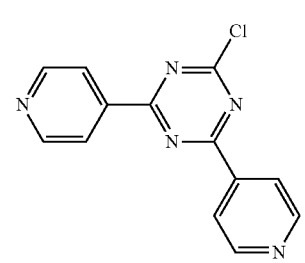
Sub 1-30
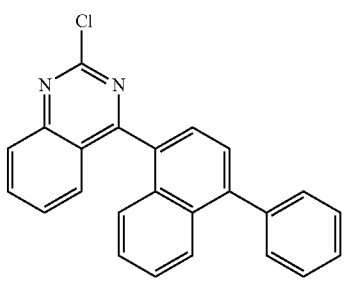
Sub 1-31
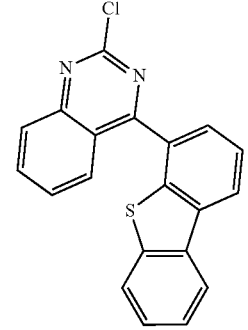

-continued
Sub 1-32
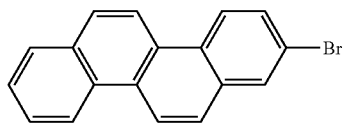
Sub 1-33
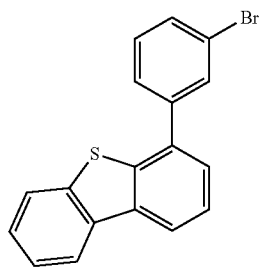
Sub 1-34
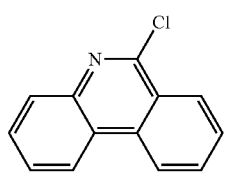
Sub 1-35
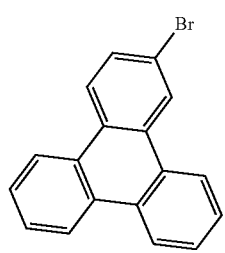
Sub 1-36
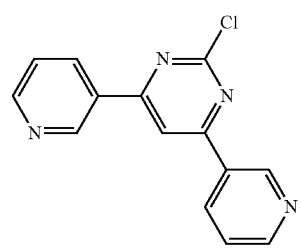
Sub 1-37
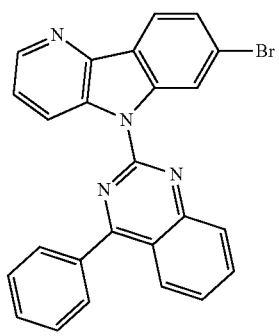
-continued
Sub 1-38
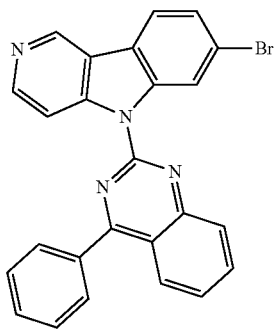
Sub 1-39
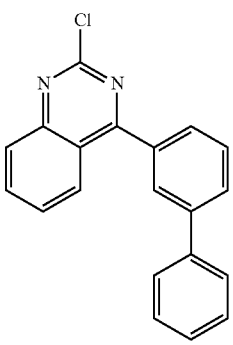
Sub 1-40
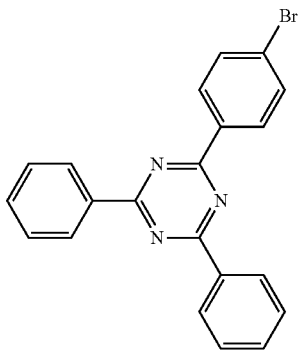
Sub 1-41
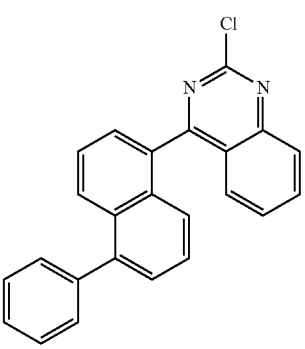

Sub 1-42
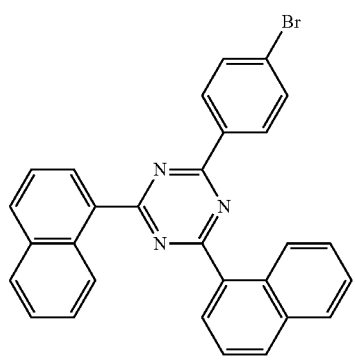
Sub 1-43
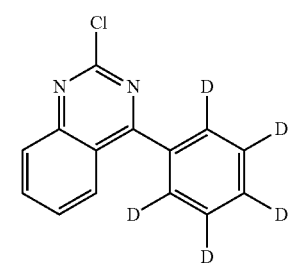
Sub 1-44
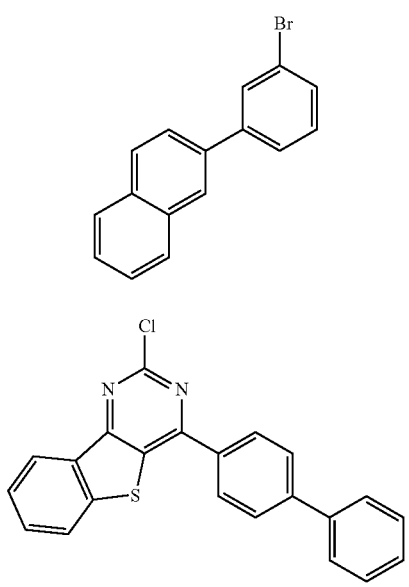
Sub 1-45
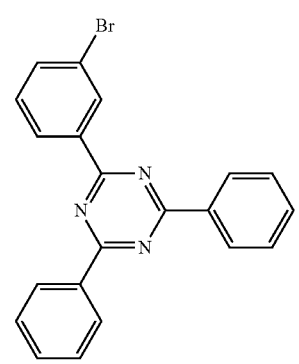
Sub 1-46
Sub 1-47
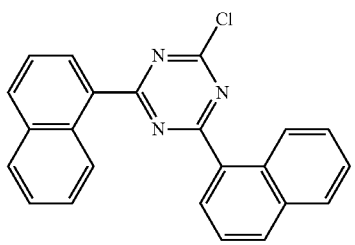
Sub 1-48
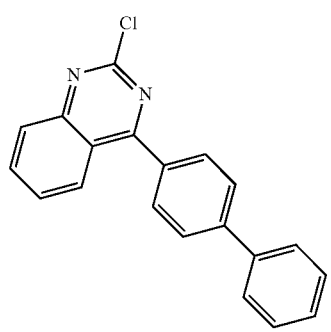
Sub 1-49
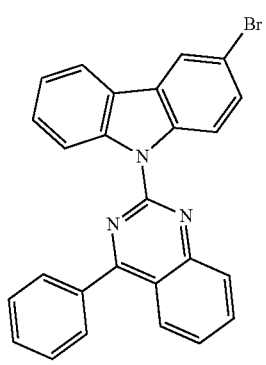
Sub 1-50
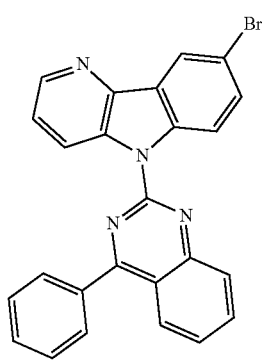
Sub 1-51
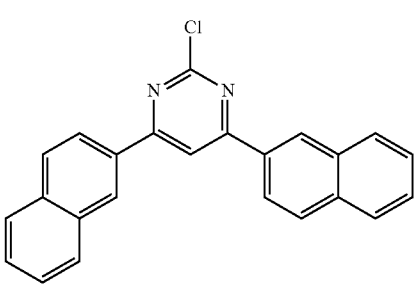

-continued
Sub 1-52
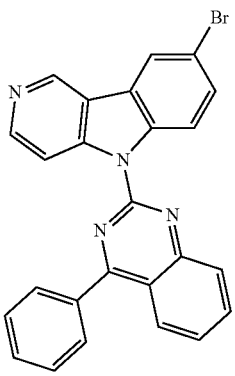
Sub 1-53
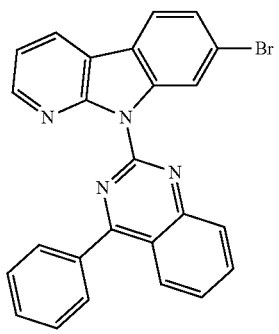
Sub 1-54
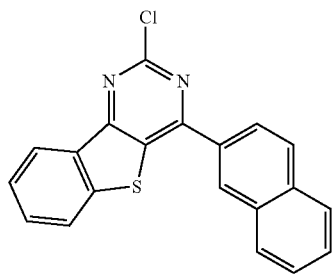
Sub 1-55
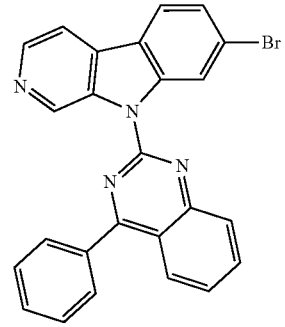
-continued
Sub 1-56
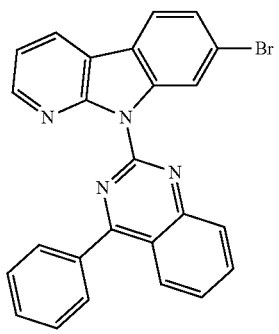
Sub 1-57
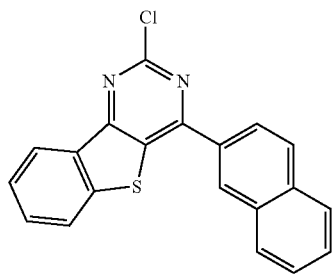
Sub 1-58
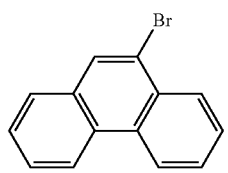
Sub 1-59
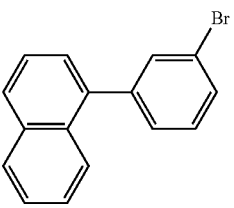
Sub 1-60
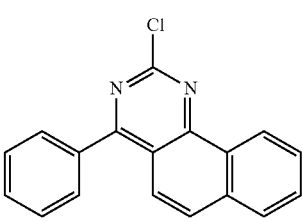
Sub 1-61
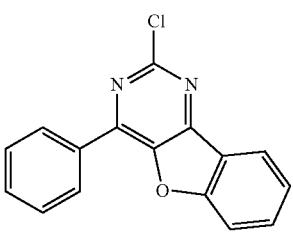

Sub 1-62
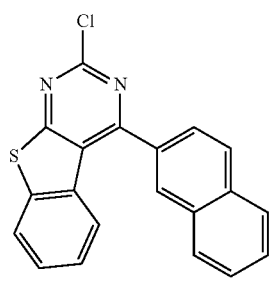
Sub 1-63
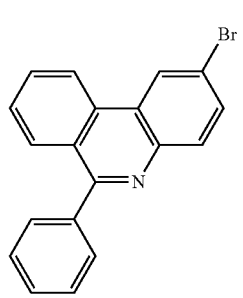
Sub 1-64
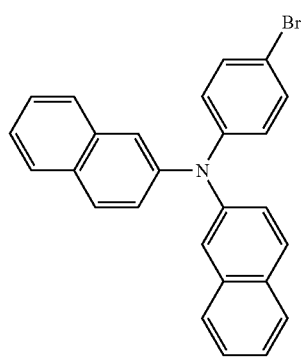
Sub 1-65
Sub 1-66
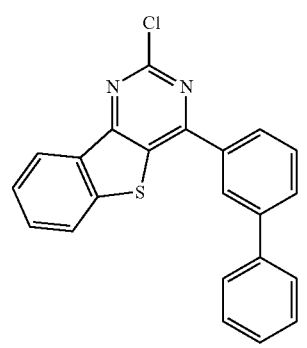
Sub 1-67
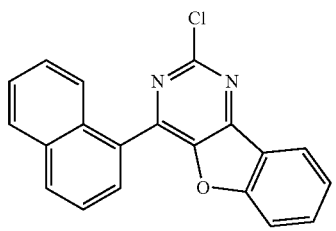
Sub 1-68
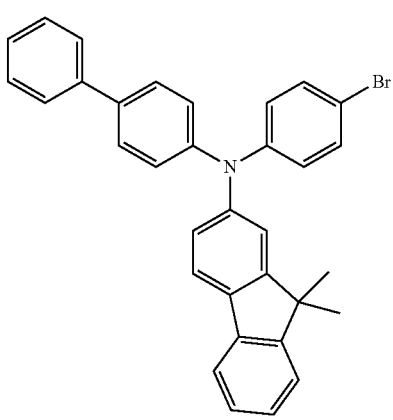
Sub 1-69
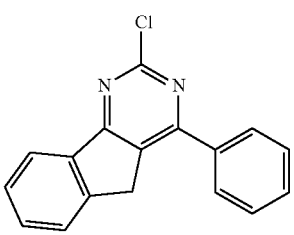
Sub 1-70
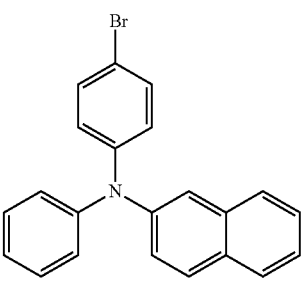
Sub 1-71
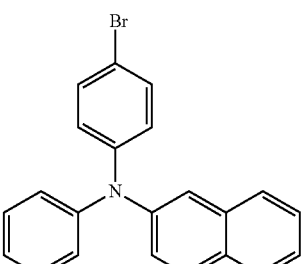
Sub 1-72
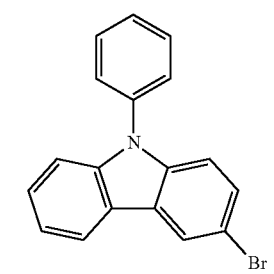

-continued

Sub 1-73
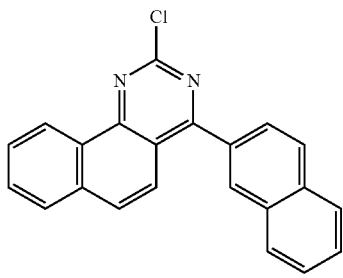

Sub 1-74
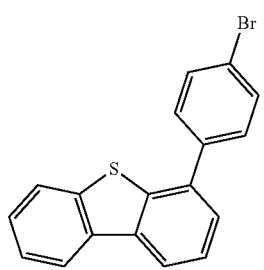

-continued

Sub 1-75
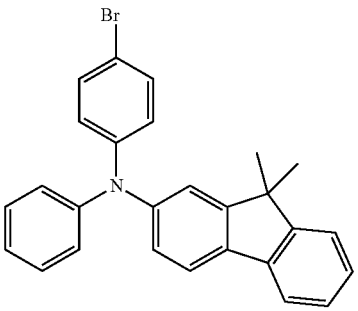

Sub 1-76
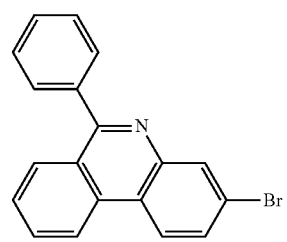

TABLE 2

| compound | FD-MS | compound | FD-MS |
|---|---|---|---|
| Sub 1-1 | m/z = 267.06($C_{15}H_{10}ClN_3$ = 267.72) | Sub 1-2 | m/z = 231.99($C_{12}H_9Br$ = 233.11) |
| Sub 1-3 | m/z = 265.07($C_{17}H_{12}ClN$ = 265.74) | Sub 1-4 | m/z = 449.05($C_{26}H_{16}BrN_3$ = 450.34) |
| Sub 1-5 | m/z = 366.09($C_{24}H_{15}ClN_2$ = 366.85) | Sub 1-6 | m/z = 266.06($C_{16}H_{11}ClN_2$ = 266.73) |
| Sub 1-7 | m/z = 279.99($C_{16}H_9Br$ = 281.15) | Sub 1-8 | m/z = 499.07($C_{30}H_{18}BrN_3$ = 500.40) |
| Sub 1-9 | m/z = 269.05($C_{13}H_8ClN_5$ = 269.69) | Sub 1-10 | m/z = 416.11($C_{26}H_{17}ClN_2$ = 416.91) |
| Sub 1-11 | m/z = 265.07($C_{17}H_{12}ClN$ = 265.74) | Sub 1-12 | m/z = 290.06($C_{18}H_{11}ClN_2$ = 290.75) |
| Sub 1-13 | m/z = 254.06($C_{18}H_{11}ClN_2$ = 290.75) | Sub 1-14 | m/z = 321.02($C_{18}H_{12}BrN$ = 322.21) |
| Sub 1-15 | m/z = 639.16($C_{43}H_{30}BrN$ = 640.62) | Sub 1-16 | m/z = 450.05($C_{25}H_{15}BrN_4$ = 451.33) |
| Sub 1-17 | m/z = 266.06($C_{16}H_{11}ClN_2$ = 266.73) | Sub 1-18 | m/z = 266.06($C_{16}H_{11}ClN_2$ = 266.73) |
| Sub 1-19 | m/z = 450.05($C_{25}H_{15}BrN_4$ = 451.33) | Sub 1-20 | m/z = 437.05($C_{25}H_{15}BrN_3$ = 438.33) |
| Sub 1-21 | m/z = 268.05($C_{14}H_9ClN_4$ = 268.70) | Sub 1-22 | m/z = 437.05($C_{25}H_{16}BrN_3$ = 438.33) |
| Sub 1-23 | m/z = 296.06($C_{16}H_9ClN_2S$ = 266.73) | Sub 1-24 | m/z = 308.02($C_{18}H_{13}Br$ = 309.21) |
| Sub 1-25 | m/z = 346.03($C_{20}H_{11}ClN_2S$ = 346.83) | Sub 1-26 | m/z = 507.15($C_{34}H_{22}ClN_3$ = 508.02) |
| Sub 1-27 | m/z = 240.05($C_{14}H_9ClN_2$ = 240.69) | Sub 1-28 | m/z = 214.03($C_{12}H_7ClN_2$ = 214.65) |
| Sub 1-29 | m/z = 269.05($C_{13}H_8ClN_5$ = 269.69) | Sub 1-30 | m/z = 366.09($C_{24}H_{15}ClN_2$ = 366.85) |
| Sub 1-31 | m/z = 346.03($C_{20}H_{11}ClN_2S$ = 346.83) | Sub 1-32 | m/z = 306.00($C_{18}H_{11}Br$ = 307.19) |
| Sub 1-33 | m/z = 337.98($C_{18}H_{11}BrS$ = 339.25) | Sub 1-34 | m/z = 213.03($C_{13}H_8ClN$ = 213.66) |
| Sub 1-35 | m/z = 306.00($C_{18}H_{11}Br$ = 307.19) | Sub 1-36 | m/z = 268.05($C_{14}H_9ClN_4$ = 268.70) |
| Sub 1-37 | m/z = 450.05($C_{25}H_{15}BrN_4$ = 451.33) | Sub 1-38 | m/z = 450.05($C_{25}H_{15}BrN_4$ = 451.33) |
| Sub 1-39 | m/z = 316.08($C_{20}H_{13}ClN_2$ = 316.79) | Sub 1-40 | m/z = 387.04($C_{21}H_{14}BrN_3$ = 388.27) |
| Sub 1-41 | m/z = 366.09($C_{24}H_{15}ClN_2$ = 366.85) | Sub 1-42 | m/z = 487.07($C_{29}H_{18}BrN_3$ = 488.39) |
| Sub 1-43 | m/z = 245.08($C_{14}H_4D_5ClN_2$ = 245.72) | Sub 1-44 | m/z = 282.00($C_{16}H_{11}Br$ = 283.17) |
| Sub 1-45 | m/z = 372.05($C_{22}H_{13}ClN_2S$ = 372.87) | Sub 1-46 | m/z = 387.04($C_{21}H_{14}BrN_3$ = 388.27) |
| Sub 1-47 | m/z = 367.09($C_{23}H_{14}ClN_3$ = 367.84) | Sub 1-48 | m/z = 316.08($C_{20}H_{13}ClN_2$ = 316.79) |
| Sub 1-49 | m/z = 449.05($C_{26}H_{16}BrN_3$ = 450.34) | Sub 1-50 | m/z = 450.05($C_{25}H_{15}BrN_4$ = 451.33) |
| Sub 1-51 | m/z = 366.09($C_{24}H_{15}ClN_2$ = 366.85) | Sub 1-52 | m/z = 450.05($C_{25}H_{15}BrN_4$ = 451.33) |
| Sub 1-53 | m/z = 290.06($C_{18}H_{11}ClN_2$ = 290.75) | Sub 1-54 | m/z = 407.12($C_{26}H_{18}ClN_3$ = 407.90) |
| Sub 1-55 | m/z = 450.05($C_{25}H_{15}BrN_4$ = 451.33) | Sub 1-56 | m/z = 450.05($C_{25}H_{15}BrN_4$ = 451.33) |
| Sub 1-57 | m/z = 346.03($C_{20}H_{11}ClN_2S$ = 346.83) | Sub 1-58 | m/z = 255.99($C_{14}H_9Br$ = 257.13) |
| Sub 1-59 | m/z = 282.00($C_{16}H_{11}Br$ = 283.17) | Sub 1-60 | m/z = 290.06($C_{18}H_{11}ClN_2$ = 290.75) |
| Sub 1-61 | m/z = 280.04($C_{16}H_9ClN_2O$ = 280.71) | Sub 1-62 | m/z = 346.03($C_{20}H_{11}ClN_2S$ = 346.83) |
| Sub 1-63 | m/z = 333.02($C_{19}H_{12}BrN$ = 334.22) | Sub 1-64 | m/z = 280.04($C_{16}H_9ClN_2O$ = 280.71) |
| Sub 1-65 | m/z = 423.06($C_{26}H_{18}BrN$ = 424.34) | Sub 1-66 | m/z = 372.05($C_{22}H_{13}ClN_2S$ = 372.87) |
| Sub 1-67 | m/z = 330.06($C_{20}H_{11}ClN_2O$ = 330.77) | Sub 1-68 | m/z = 515.12($C_{33}H_{26}BrN$ = 516.48) |
| Sub 1-69 | m/z = 296.02($C_{16}H_9ClN_2S$ = 296.77) | Sub 1-70 | m/z = 373.05($C_{22}H_{16}BrN$ = 374.28) |
| Sub 1-71 | m/z = 321.02($C_{16}H_{12}BrN$ = 322.21) | Sub 1-72 | m/z = 282.00($C_{16}H_{11}Br$ = 283.17) |
| Sub 1-73 | m/z = 340.08($C_{22}H_{13}ClN_2$ = 340.81) | Sub 1-74 | m/z = 337.08($C_{18}H_{11}BrS$ = 340.81) |
| Sub 1-75 | m/z = 439.09($C_{27}H_{22}BrN$ = 440.38) | Sub 1-76 | m/z = 333.02($C_{19}H_{12}BrN$ = 334.22) |

III. Synthesis of Product

1. Synthesis Example of P-1-1

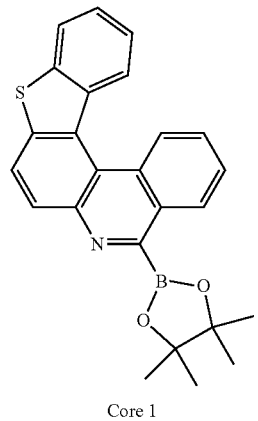

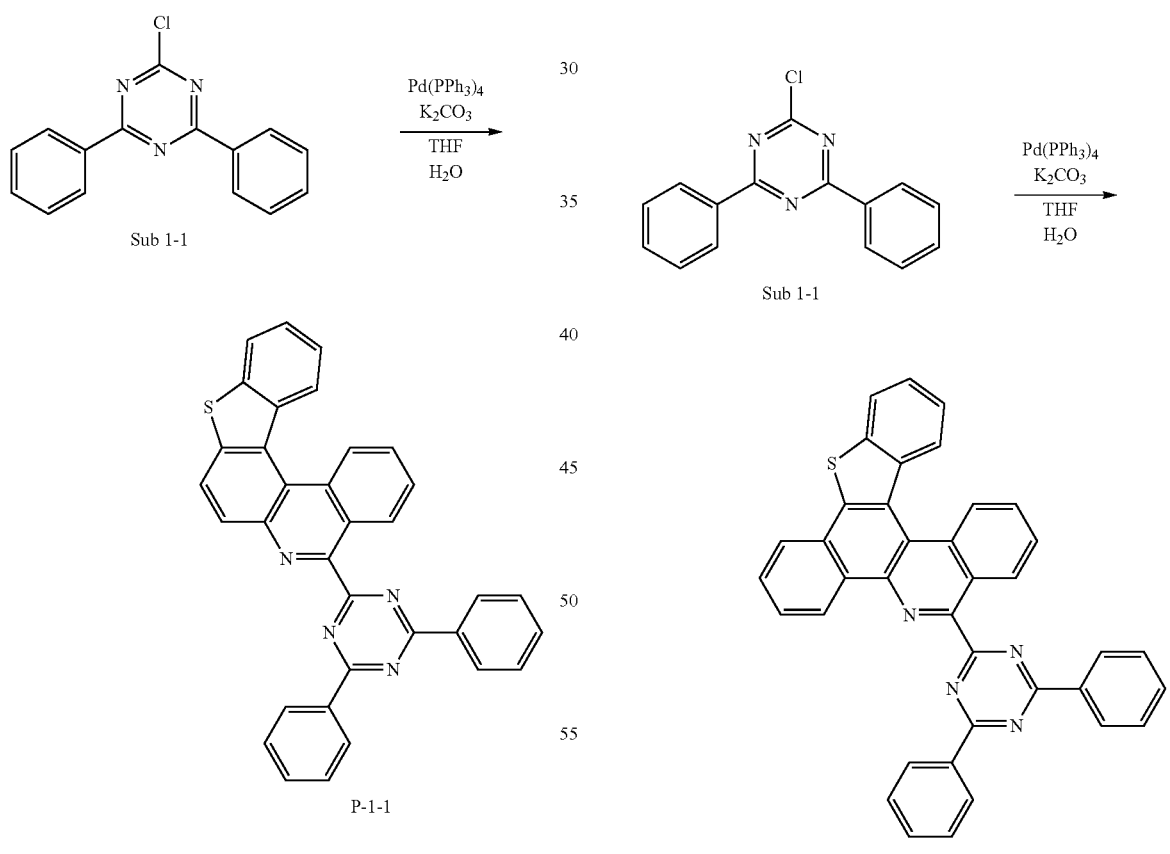

Sub 1-1 (3.58 g, 13.37 mmol), Pd(PPh$_3$)$_4$ (0.46 g, 0.40 mmol), K$_2$CO$_3$ (5.54 g, 40.11 mmol), THF (60 ml) and H$_2$O (30 ml) was added to Core 1 (5.5 g, 13.37 mmol), and then the mixture was refluxed at 90° C. for 12 hours. When the reaction was completed, the reaction product was cooled to room temperature. Then, the reaction product was extracted with MC and washed with water. Then, the organic layer was dried with MgSO$_4$ and concentrated. Then, the concentrate was separated by silica gel column to obtain 5.32 g (yield: 77%) product.

2. Synthesis Example of P-2-1

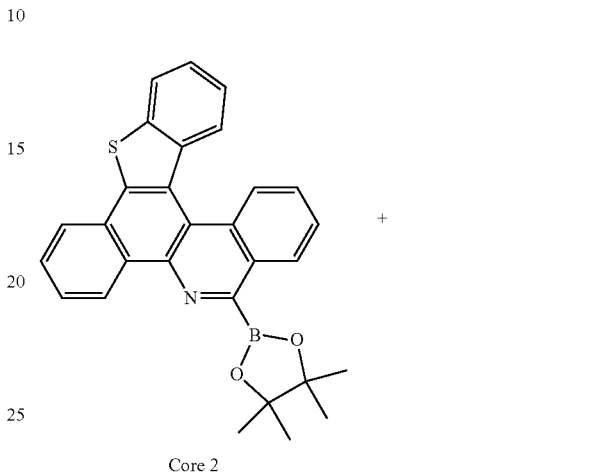

Sub 1-1 (2.15 g, 8.02 mmol), Pd(PPh$_3$)$_4$ (0.28 g, 0.24 mmol), K$_2$CO$_3$ (3.33 g, 24.06 mmol), THF (100 ml) and H$_2$O (50 ml) were added to Core 2 (3.7 g, 8.02 mmol), and then 3.36 g (yield: 74%) of the product was obtained by the same method as in synthesis of P-1-1.

3. Synthesis Example of P-3-3

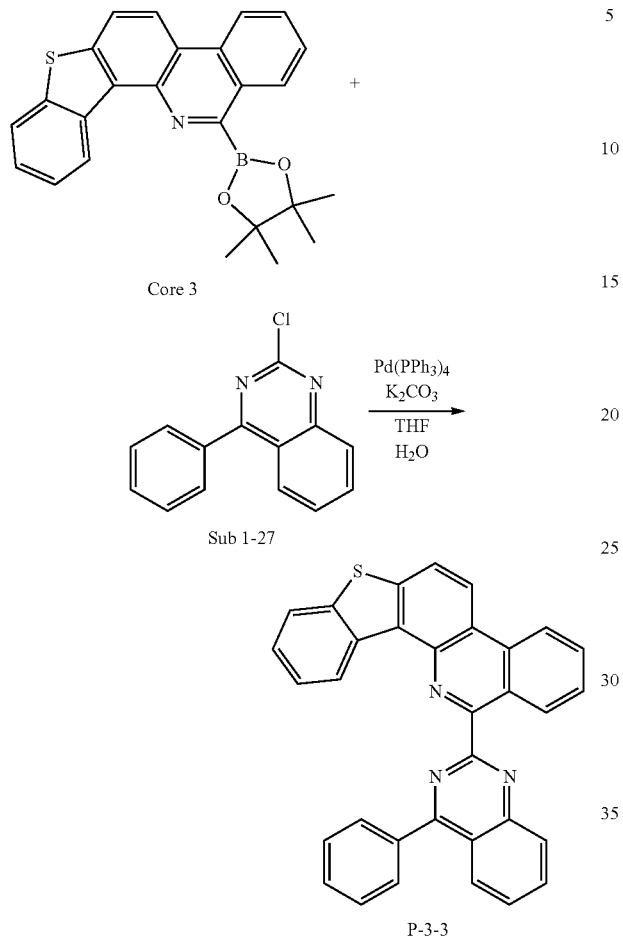

4. Synthesis Example of P-4-8

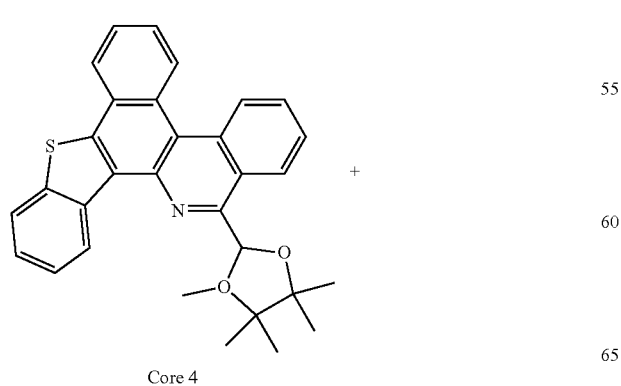

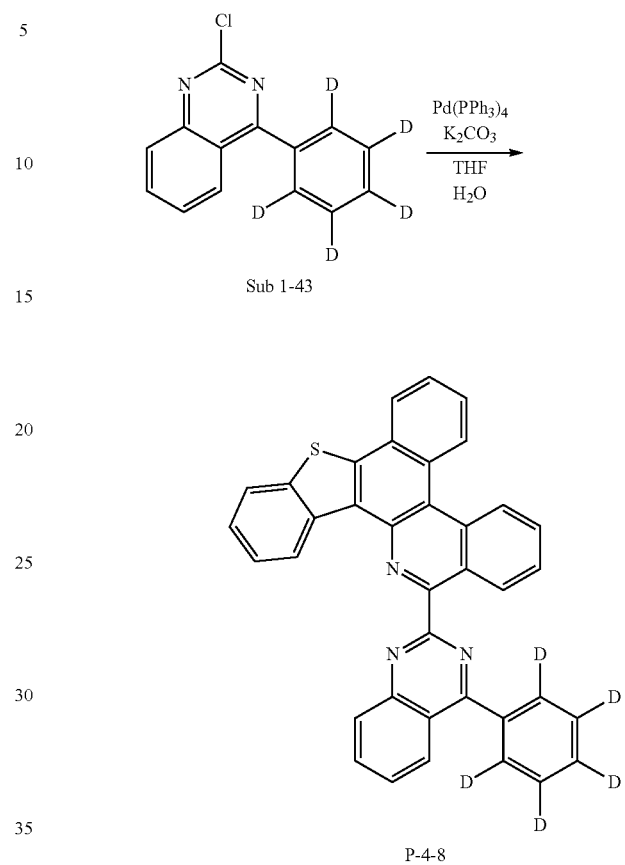

Sub 1-27 (2.34 g, 9.72 mmol), Pd(PPh$_3$)$_4$ (0.34 g, 0.29 mmol), K$_2$CO$_3$ (4.03 g, 29.17 mmol), THF (80 ml) and H$_2$O (40 ml) were added to Core 3 (4 g, 9.72 mmol), and then 3.24 g (yield: 68%) of the product was obtained by the same method as in synthesis of P-1-1.

Sub 1-43 (1.17 g, 4.75 mmol), Pd(PPh$_3$)$_4$ (0.16 g, 0.14 mmol), K$_2$CO$_3$ (1.97 g, 14.24 mmol), THF (50 ml) and H$_2$O (20 ml) were added to Core 4 (2.2 g, 4.75 mmol), and then 1.81 g (yield: 70%) of the product was obtained by the same method as in synthesis of P-1-1.

5. Synthesis Example of P-5-7

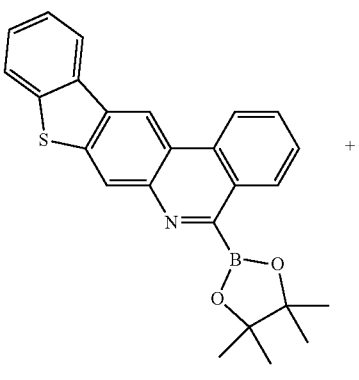

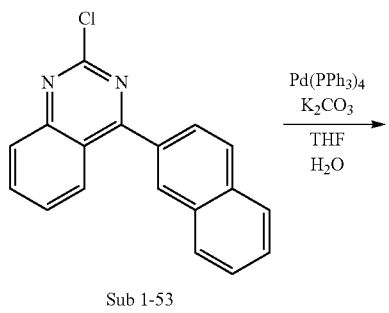

Sub 1-53

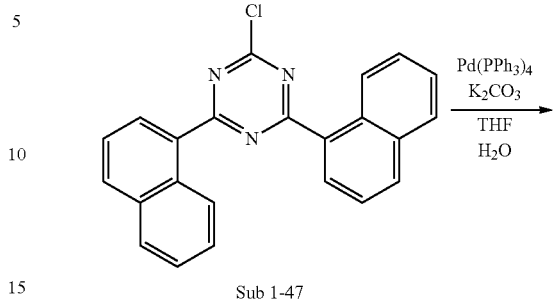

Sub 1-47

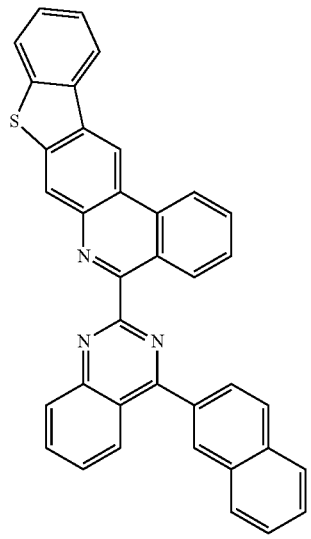

P-5-7

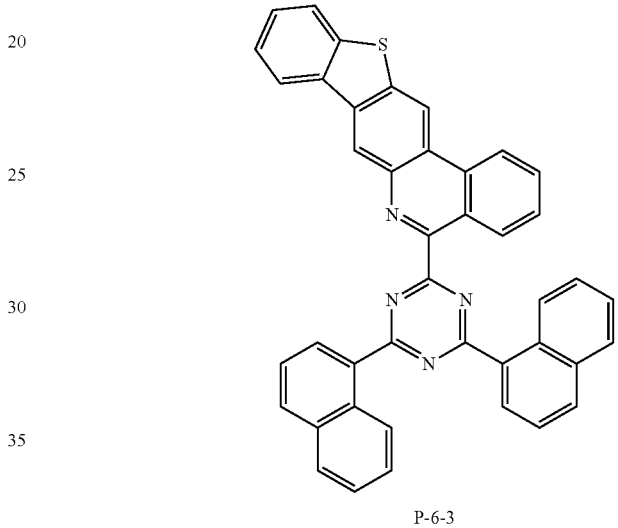

P-6-3

Sub 1-53 (1.27 g, 4.38 mmol), Pd(PPh₃)₄ (0.15 g, 0.13 mmol), K₂CO₃ (1.81 g, 13.13 mmol), THF (50 ml) and H₂O (20 ml) were added to Core 5 (1.80 g, 4.38 mmol), and then 2.13 g (yield: 90%) of the product was obtained by the same method as in synthesis of P-1-1.

6. Synthesis Example of P-6-3

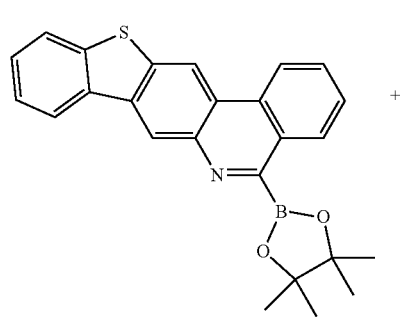

Core 6

Sub 1-47 (2.24 g, 6.08 mmol), Pd(PPh₃)₄ (0.21 g, 0.18 mmol), K₂CO₃ (2.52 g, 18.23 mmol), THF (60 ml) and H₂O (30 ml) were added to Core 6 (2.50 g, 6.08 mmol), and then 3.07 g (yield: 82%) of the product was obtained by the same method as in synthesis of P-1-1.

7. Synthesis Example of P-7-6

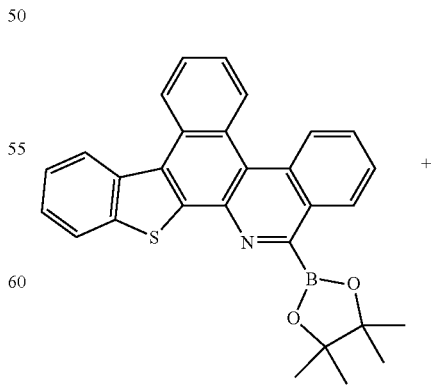

Core 7

121

-continued

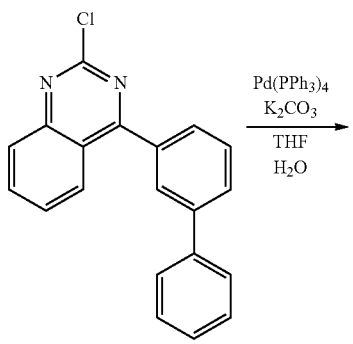

Sub 1-39

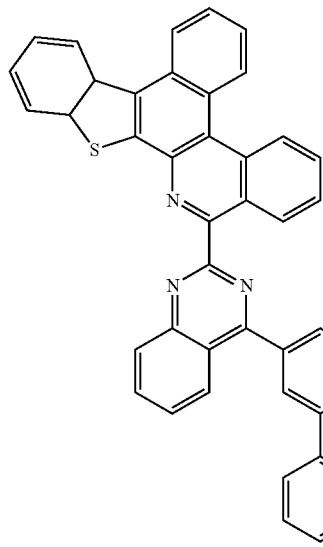

P-7-6

Sub 1-39 (1.17 g, 3.68 mmol), Pd(PPh₃)₄ (0.13 g, 0.11 mmol), K₂CO₃ (1.53 g, 11.05 mmol), THF (50 ml) and H₂O (20 ml) were added to Core 7 (1.70 g, 3.68 mmol), and then 1.93 g (yield: 85%) of the product was obtained by the same method as in synthesis of P-1-1.

8. Synthesis Example of P-8-11

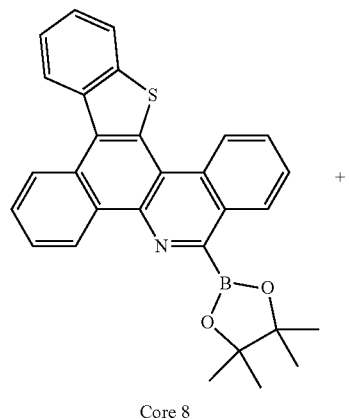

Core 8

122

-continued

Sub 1-61

P-8-11

Sub 1-61 (1.28 g, 4.55 mmol), Pd(PPh₃)₄ (0.16 g, 0.14 mmol), K₂CO₃ (1.89 g, 13.65 mmol), THF (50 ml) and H₂O (20 ml) were added to Core 8 (2.10 g, 4.55 mmol), and then 2.27 g (yield: 86%) of the product was obtained by the same method as in synthesis of P-1-1.

9. Synthesis Example of P-9-10

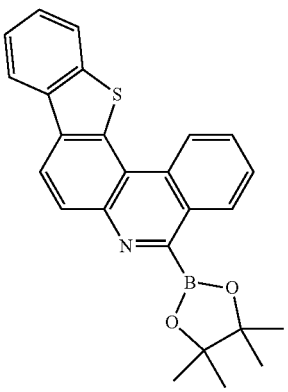

Core 9

10. Synthesis Example of P-10-14

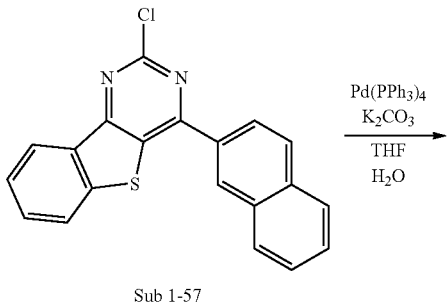

Sub 1-57

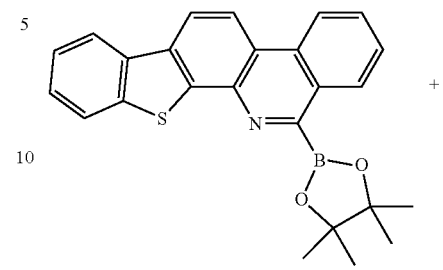

Core 10

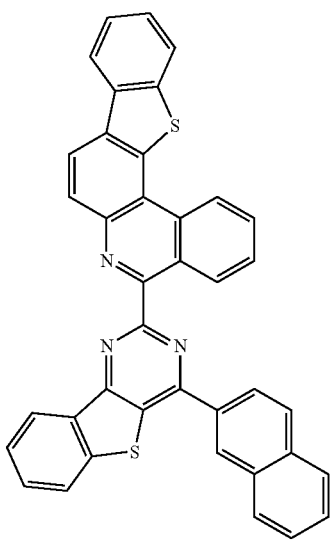

P-9-10

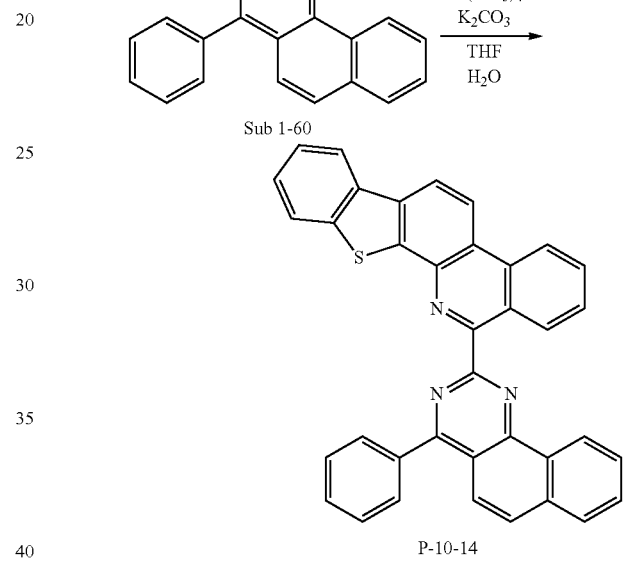

Sub 1-60

P-10-14

Sub 1-57 (2.53 g, 7.29 mmol), Pd(PPh$_3$)$_4$ (0.25 g, 0.22 mmol), K$_2$CO$_3$ (3.02 g, 21.88 mmol), THF (50 ml) and H$_2$O (20 ml) were added to Core 9 (3 g, 7.29 mmol), and then 3.95 g (yield: 91%) of the product was obtained by the same method as in synthesis of P-1-1.

Sub 1-60 (1.84 g, 6.32 mmol), Pd(PPh$_3$)$_4$ (0.22 g, 0.19 mmol), K$_2$CO$_3$ (2.62 g, 18.96 mmol), THF (50 ml) and H$_2$O (20 ml) were added to Core 10 (2.60 g, 6.32 mmol), and then 3.04 g (yield: 89%) of the product was obtained by the same method as in synthesis of P-1-1.

TABLE 3

| compound | FD-MS | compound | FD-MS |
|---|---|---|---|
| P-1-1 | m/z = 516.14(C$_{34}$H$_{20}$N$_4$S = 516.62) | P-1-2 | m/z = 514.15(C$_{36}$H$_{22}$N$_2$S = 515.65) |
| P-1-3 | m/z = 517.14(C$_{33}$H$_{19}$N$_5$S = 517.61) | P-1-4 | m/z = 515.15(C$_{35}$H$_{21}$N$_3$S = 515.63) |
| P-1-5 | m/z = 642.19(C$_{44}$H$_{26}$N$_4$S = 642.78) | P-1-6 | m/z = 592.17(C$_{40}$H$_{24}$N$_4$S = 592.72) |
| P-1-7 | m/z = 517.14(C$_{33}$H$_{19}$N$_5$S = 517.61) | P-1-8 | m/z = 489.13(C$_{33}$H$_{19}$N$_3$S = 489.60) |
| P-1-9 | m/z = 595.12(C$_{39}$H$_{21}$N$_3$S$_2$ = 595.74) | P-1-10 | m/z = 665.19(C$_{47}$H$_{27}$N$_3$S = 665.81) |
| P-1-11 | m/z = 565.16(C$_{39}$H$_{23}$N$_3$S = 565.69) | P-1-12 | m/z = 539.15(C$_{37}$H$_{21}$N$_3$S = 539.66) |
| P-1-13 | m/z = 656.20(C$_{45}$H$_{28}$N$_4$S = 656.81) | P-1-14 | m/z = 539.15(C$_{37}$H$_{21}$N$_3$S = 539.66) |
| P-1-15 | m/z = 545.10(C$_{35}$H$_{19}$N$_3$S$_2$ = 5453.68) | P-1-16 | m/z = 513.15(C$_{35}$H$_{19}$N$_3$O$_2$ = 513.56) |
| P-1-17 | m/z = 828.31(C$_{62}$H$_{40}$N$_2$O = 829.02) | P-1-18 | m/z = 638.21(C$_{45}$H$_{26}$N$_4$O = 638.73) |
| P-1-19 | m/z = 688.23(C$_{49}$H$_{28}$N$_4$O = 688.79) | P-1-20 | m/z = 639.21(C$_{44}$H$_{25}$N$_5$O = 639.72) |
| P-2-1 | m/z = 566.16(C$_{38}$H$_{22}$N$_4$S = 566.68) | P-2-2 | m/z = 564.17(C$_{36}$H$_{20}$N$_6$S = 564.71) |
| P-2-3 | m/z = 568.15(C$_{36}$H$_{20}$N$_6$S = 568.66) | P-2-4 | m/z = 565.16(C$_{39}$H$_{23}$N$_3$S = 565.69) |
| P-2-5 | m/z = 642.19(C$_{44}$H$_{26}$N$_4$S = 642.78) | P-2-6 | m/z = 642.19(C$_{44}$H$_{26}$N$_4$S = 642.78) |
| P-2-7 | m/z = 565.16(C$_{39}$H$_{23}$N$_3$S = 565.69) | P-2-8 | m/z = 539.15(C$_{17}$H$_{21}$N$_3$S = 539.66) |
| P-2-9 | m/z = 645.13(C$_{43}$H$_{23}$N$_3$S$_2$ = 645.80) | P-2-10 | m/z = 589.16(C$_{41}$H$_{23}$N$_3$S = 589.72) |
| P-2-11 | m/z = 615.18(C$_{43}$H$_{25}$N$_3$S = 615.75) | P-2-12 | m/z = 589.16(C$_{41}$H$_{23}$N$_3$S = 589.72) |
| P-2-13 | m/z = 706.22(C$_{49}$H$_{30}$N$_4$S = 706.87) | P-2-14 | m/z = 589.16(C$_{41}$H$_{23}$N$_3$S = 589.72) |
| P-2-15 | m/z = 645.13(C$_{43}$H$_{23}$N$_3$S$_2$ = 645.80) | P-2-16 | m/z = 563.16(C$_{39}$H$_{21}$N$_3$O$_2$ = 563.62) |
| P-2-17 | m/z = 754.30(C$_{56}$H$_{38}$N$_2$O = 754.93) | P-2-18 | m/z = 688.23(C$_{49}$H$_{28}$N$_4$O = 688.79) |

TABLE 3-continued

| compound | FD-MS | compound | FD-MS |
| --- | --- | --- | --- |
| P-2-19 | m/z = 689.22($C_{48}H_{27}N_5O$ = 689.78) | P-2-20 | m/z = 689.22($C_{38}H_{27}N_5O$ = 689.78) |
| P-3-1 | m/z = 592.17($C_{40}H_{24}N_4S$ = 592.72) | P-3-2 | m/z = 515.15($C_{35}H_{21}N_3S$ = 515.63) |
| P-3-3 | m/z = 489.13($C_{33}H_{19}N_3S$ = 489.13) | P-3-4 | m/z = 595.12($C_{39}H_{21}N_3S_2$ = 595.74) |
| P-3-5 | m/z = 615.18($C_{43}H_{25}N_3S$ = 615.75) | P-3-6 | m/z = 565.16($C_{39}H_{23}N_3S$ = 565.69) |
| P-3-7 | m/z = 539.15($C_{37}H_{21}N_3S$ = 539.66) | P-3-8 | m/z = 656.20($C_{45}H_{28}N_4S$ = 656.81) |
| P-3-9 | m/z = 539.15($C_{37}H_{21}N_3S$ = 539.66) | P-3-10 | m/z = 545.10($C_{35}H_{19}N_3S_2$ = 545.68) |
| P-3-11 | m/z = 529.12($C_{35}H_{19}N_3OS$ = 529.62) | P-3-12 | m/z = 644.23($C_{46}H_{32}N_2S$ = 644.84) |
| P-3-13 | m/z = 654.19($C_{45}H_{26}N_4S$ = 654.79) | P-3-14 | m/z = 655.18($C_{44}H_{25}N_5S$ = 655.78) |
| P-3-15 | m/z = 655.18($C_{44}H_{25}N_5S$ = 655.78) | P-3-16 | m/z = 471.16($C_{35}H_{21}NO$ = 471.56) |
| P-3-17 | m/z = 497.18($C_{37}H_{23}NO$ = 497.60) | P-3-18 | m/z = 522.17($C_{38}H_{22}N_2O$ = 522.61) |
| P-3-19 | m/z = 445.15($C_{33}H_{19}NO$ = 445.52) | P-3-20 | m/z = 527.13($C_{37}H_{21}NOS$ = 527.64) |
| P-4-1 | m/z = 566.16($C_{38}H_{22}N_4S$ = 566.68) | P-4-2 | m/z = 564.17($C_{40}H_{24}N_2S$ = 564.71) |
| P-4-3 | m/z = 567.15($C_{37}H_{21}N_5S$ = 567.67) | P-4-4 | m/z = 565.16($C_{39}H_{23}N_3S$ = 565.69) |
| P-4-5 | m/z = 692.20($C_{48}H_{28}N_4S$ = 692.84) | P-4-6 | m/z = 642.19($C_{44}H_{26}N_4S$ = 642.78) |
| P-4-7 | m/z = 565.16($C_{39}H_{23}N_3S$ = 565.69) | P-4-8 | m/z = 544.18($C_{37}H_{16}D_5N_3S$ = 544.69) |
| P-4-9 | m/z = 553.16($C_{38}H_{23}N_3S$ = 553.68) | P-4-10 | m/z = 645.13($C_{43}H_{23}N_3S_2$ = 645.80) |
| P-4-11 | m/z = 629.16($C_{43}H_{23}N_3OS$ = 629.74) | P-4-12 | m/z = 628.20($C_{45}H_{28}N_2S$ = 628.79) |
| P-4-13 | m/z = 704.20($C_{49}H_{28}N_4S$ = 704.85) | P-4-14 | m/z = 705.20($C_{48}H_{27}N_5S$ = 705.84) |
| P-4-15 | m/z = 705.20($C_{48}H_{27}N_5S$ = 705.84) | P-4-16 | m/z = 519.16($C_{39}H_{21}NO$ = 519.60) |
| P-4-17 | m/z = 560.19($C_{41}H_{24}N_2O$ = 560.66) | P-4-18 | m/z = 496.16($C_{36}H_{20}N_2O$ = 496.57) |
| P-4-19 | m/z = 579.14($C_{39}H_{21}N_3OS$ = 579.68) | P-4-20 | m/z = 550.18($C_{38}H_{22}N_4O$ = 550.62) |
| P-5-1 | m/z = 516.14($C_{34}H_{20}N_4S$ = 516.62) | P-5-2 | m/z = 515.15($C_{35}H_{21}N_3S$ = 515.63) |
| P-5-3 | m/z = 518.13($C_{32}H_{18}N_6S$ = 518.60) | P-5-4 | m/z = 515.15($C_{35}H_{21}N_3S$ = 515.63) |
| P-5-5 | m/z = 592.17($C_{40}H_{24}N_4S$ = 592.72) | P-5-6 | m/z = 565.16($C_{39}H_{23}N_3S$ = 565.69) |
| P-5-7 | m/z = 539.15($C_{37}H_{21}N_3S$ = 539.66) | P-5-8 | m/z = 656.20($C_{45}H_{28}N_4S$ = 656.81) |
| P-5-9 | m/z = 539.15($C_{37}H_{21}N_3S$ = 539.66) | P-5-10 | m/z = 595.12($C_{39}H_{21}N_3S_2$ = 595.74) |
| P-5-11 | m/z = 579.14($C_{39}H_{21}N_3OS$ = 579.68) | P-5-12 | m/z = 628.20($C_{45}H_{28}N_2S$ = 628.79) |
| P-5-13 | m/z = 654.19($C_{45}H_{26}N_4S$ = 654.79) | P-5-14 | m/z = 655.18($C_{44}H_{25}N_5S$ = 655.78) |
| P-5-15 | m/z = 655.18($C_{44}H_{25}N_5S$ = 655.78) | P-5-16 | m/z = 471.16($C_{35}H_{21}NO$ = 471.56) |
| P-5-17 | m/z = 498.17($C_{36}H_{22}N_2O$ = 498.59) | P-5-18 | m/z = 473.15($C_{33}H_{19}N_3O$ = 473.54) |
| P-5-19 | m/z = 447.14($C_{31}H_{17}N_3O$ = 447.50) | P-5-20 | m/z = 527.13($C_{37}H_{21}NOS$ = 527.64) |
| P-6-1 | m/z = 516.14($C_{34}H_{20}N_4S$ = 516.62) | P-6-2 | m/z = 615.18($C_{43}H_{25}N_3S$ = 615.75) |
| P-6-3 | m/z = 616.14($C_{42}H_{24}N_4S$ = 616.74) | P-6-4 | m/z = 515.15($C_{35}H_{21}N_3S$ = 515.63) |
| P-6-5 | m/z = 642.19($C_{44}H_{26}N_4S$ = 642.78) | P-6-6 | m/z = 592.17($C_{40}H_{24}N_4S$ = 592.72) |
| P-6-7 | m/z = 515.15($C_{35}H_{21}N_3S$ = 515.63) | P-6-8 | m/z = 489.13($C_{33}H_{19}N_3S$ = 489.60) |
| P-6-9 | m/z = 595.12($C_{39}H_{21}N_3S_2$ = 595.74) | P-6-10 | m/z = 615.18($C_{43}H_{25}N_3S$ = 615.75) |
| P-6-11 | m/z = 565.16($C_{39}H_{23}N_3S$ = 565.69) | P-6-12 | m/z = 539.15($C_{37}H_{21}N_3S$ = 539.66) |
| P-6-13 | m/z = 756.23($C_{53}H_{32}N_4S$ = 756.93) | P-6-14 | m/z = 589.16(($C_{41}H_{23}N_3S$ = 589.72) |
| P-6-15 | m/z = 545.10($C_{35}H_{19}N_3S_2$ = 545.68) | P-6-16 | m/z = 513.15($C_{35}H_{19}N_3O_2$ = 513.56) |
| P-6-17 | m/z = 828.31($C_{62}H_{40}N_2O$ = 829.02) | P-6-18 | m/z = 638.21($C_{45}H_{26}N_4O$ = 638.73) |
| P-6-19 | m/z = 688.23($C_{49}H_{28}N_4O$ = 688.79) | P-6-20 | m/z = 639.21($C_{44}H_{25}N_5O$ = 639.60) |
| P-7-1 | m/z = 642.19($C_{44}H_{26}N_4S$ = 642.78) | P-7-2 | m/z = 565.16($C_{39}H_{23}N_3S$ = 565.69) |
| P-7-3 | m/z = 544.18($C_{37}H_{16}D_5N_3S$ = 544.69) | P-7-4 | m/z = 553.16($C_{38}H_{23}N_3S$ = 553.68) |
| P-7-5 | m/z = 645.13($C_{43}H_{23}N_3S_2$ = 645.80) | P-7-6 | m/z = 615.18($C_{43}H_{25}N_3S$ = 615.75) |
| P-7-7 | m/z = 589.16($C_{41}H_{23}N_3S$ = 589.72) | P-7-8 | m/z = 706.22($C_{49}H_{30}N_4S$ = 706.87) |
| P-7-9 | m/z = 589.16($C_{41}H_{23}N_3S$ = 589.72) | P-7-10 | m/z = 645.13($C_{43}H_{23}N_3S_2$ = 645.80) |
| P-7-11 | m/z = 629.16($C_{43}H_{23}N_3OS$ = 629.74) | P-7-12 | m/z = 628.20($C_{45}H_{28}N_2S$ = 628.79) |
| P-7-13 | m/z = 704.20($C_{49}H_{28}N_4S$ = 704.85) | P-7-14 | m/z = 705.20($C_{48}H_{27}N_5S$ = 705.84) |
| P-7-15 | m/z = 705.20($C_{48}H_{27}N_5S$ = 705.84) | P-7-16 | m/z = 519.16($C_{39}H_{21}NO$ = 519.60) |
| P-7-17 | m/z = 560.19($C_{39}H_{21}NO$ = 560.60) | P-7-18 | m/z = 496.16($C_{36}H_{20}N_2O$ = 496.57) |
| P-7-19 | m/z = 523.17($C_{37}H_{21}N_3O$ = 523.60) | P-7-20 | m/z = 550.18($C_{38}H_{22}N_4O$ = 550.62) |
| P-8-1 | m/z = 566.16($C_{38}H_{22}N_4S$ = 566.68) | P-8-2 | m/z = 564.17($C_{40}H_{24}N_2S$ = 564.71) |
| P-8-3 | m/z = 568.16($C_{36}H_{20}N_6S$ = 568.66) | P-8-4 | m/z = 565.16($C_{39}H_{23}N_3S$ = 565.69) |
| P-8-5 | m/z = 642.19($C_{44}H_{26}N_4S$ = 642.78) | P-8-6 | m/z = 642.19($C_{44}H_{26}N_4S$ = 642.78) |
| P-8-7 | m/z = 565.16($C_{39}H_{23}N_3S$ = 565.69) | P-8-8 | m/z = 539.15($C_{37}H_{21}N_3S$ = 539.66) |
| P-8-9 | m/z = 645.13($C_{43}H_{23}N_3S_2$ = 645.80) | P-8-10 | m/z = 665.19($C_{47}H_{27}N_5S$ = 665.81) |
| P-8-11 | m/z = 579.14($C_{39}H_{21}N_3OS$ = 579.68) | P-8-12 | m/z = 694.24($C_{50}H_{34}N_2S$ = 694.90) |
| P-8-13 | m/z = 704.20($C_{49}H_{28}N_4S$ = 704.85) | P-8-14 | m/z = 705.20($C_{48}H_{27}N_5S$ = 705.84) |
| P-8-15 | m/z = 705.20($C_{48}N_{27}N_5S$ = 705.84) | P-8-16 | m/z = 521.18($C_{39}H_{23}NO$ = 521.62) |
| P-8-17 | m/z = 547.19($C_{41}H_{25}NO$ = 547.66) | P-8-18 | m/z = 572.19($C_{42}H_{24}N_2O$ = 572.67) |
| P-8-19 | m/z = 495.16($C_{37}H_{21}NO$ = 495.58) | P-8-20 | m/z = 577.15($C_{41}H_{23}NOS$ = 577.70) |
| P-9-1 | m/z = 516.14($C_{34}H_{20}N_4S$ = 516.62) | P-9-2 | m/z = 515.15($C_{35}H_{21}N_3S$ = 515.63) |
| P-9-3 | m/z = 518.13($C_{32}H_{18}N_6S$ = 518.60) | P-9-4 | m/z = 515.15($C_{35}H_{21}N_3S$ = 515.63) |
| P-9-5 | m/z = 692.20($C_{48}H_{28}N_4S$ = 692.84) | P-9-6 | m/z = 565.16($C_{39}H_{23}N_3S$ = 565.69) |
| P-9-7 | m/z = 539.15($C_{37}H_{21}N_3S$ = 539.66) | P-9-8 | m/z = 656.20($C_{45}H_{28}N_4S$ = 656.81) |
| P-9-9 | m/z = 621.13($C_{41}H_{23}N_3S_2$ = 621.78) | P-9-10 | m/z = 595.12($C_{39}H_{21}N_3S_2$ = 595.74) |
| P-9-11 | m/z = 621.13($C_{41}H_{23}N_3S_2$ = 621.78) | P-9-12 | m/z = 628.20($C_{45}H_{28}N_2S$ = 628.79) |
| P-9-13 | m/z = 654.19($C_{45}H_{26}N_4S$ = 654.79) | P-9-14 | m/z = 655.18($C_{44}H_{25}N_5S$ = 655.78) |
| P-9-15 | m/z = 655.18($C_{44}H_{25}N_5S$ = 655.78) | P-9-16 | m/z = 471.16($C_{35}H_{21}NO$ = 471.56) |
| P-9-17 | m/z = 498.17($C_{36}H_{22}N_2O$ = 498.59) | P-9-18 | m/z = 522.17($C_{38}H_{22}N_2O$ = 522.61) |
| P-9-19 | m/z = 447.14($C_{31}H_{17}N_3O$ = 447.50) | P-9-20 | m/z = 527.13($C_{37}H_{21}NOS$ = 527.64) |
| P-10-1 | m/z = 516.14($C_{34}H_{20}N_4S$ = 516.62) | P-10-2 | m/z = 515.15($C_{35}H_{21}N_3S$ = 515.63) |
| P-10-3 | m/z = 518.13($C_{32}H_{18}N_6S$ = 518.60) | P-10-4 | m/z = 515.15($C_{35}H_{21}N_3S$ = 515.63) |
| P-10-5 | m/z = 592.17($C_{40}H_{24}N_4S$ = 592.72) | P-10-6 | m/z = 592.17($C_{40}H_{24}N_4S$ = 592.72) |
| P-10-7 | m/z = 515.15($C_{35}H_{21}N_3S$ = 515.63) | P-10-8 | m/z = 489.13($C_{33}H_{19}N_3S$ = 489.60) |
| P-10-9 | m/z = 595.12($C_{39}H_{21}N_3S$ = 595.74) | P-10-10 | m/z = 615.18($C_{43}H_{25}N_3S$ = 615.75) |
| P 10 11 | m/z = 565.16($C_{39}H_{23}N_3S$ = 565.69) | P-10-12 | m/z = 539.15($C_{37}H_{21}N_3S$ = 539.66) |
| P-10-13 | m/z = 656.20($C_{45}H_{28}N_4S$ = 656.81) | P-10-14 | m/z = 539.15($C_{37}H_{21}N_3S$ = 539.66) |

TABLE 3-continued

| compound | FD-MS | compound | FD-MS |
|---|---|---|---|
| P-10-15 | m/z = 545.10($C_{35}H_{19}N_3S_2$ = 545.68) | P-10-16 | m/z = 522.17($C_{38}H_{22}N_2O$ = 522.61) |
| P-10-17 | m/z = 421.15($C_{31}H_{19}NO$ = 421.50) | P-10-18 | m/z = 471.16($C_{35}H_{21}NO$ = 471.56) |
| P-10-19 | m/z = 495.16($C_{37}H_{21}NO$ = 495.58) | P-10-20 | m/z = 495.16($C_{37}H_{21}NO$ = 495.58) |

Fabrication and Evaluation of Organic Electronic Element

[Example 1] Red OLED

First, an ITO layer (anode) was formed on a glass substrate, and then $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") was vacuum-deposited on the ITO layer to form a hole injection layer with a thickness of 60 nm. Subsequently, 4,4-bis[N-(1-naphthyl)-N-phenylamino]biphenyl (hereinafter, "NPB") was vacuum-deposited on the hole injection layer to form a hole transport layer with a thickness of 60 nm. Then, a light emitting layer with a thickness of 30 nm was formed on the hole transport layer by using compound P-1-1 of the present invention as a host material and (piq)$_2$Ir(acac) [Bis(1-phenylisoquinoline)iridium(III)acetylacetonate] as a dopant material in a weight ratio—of 95:5. Subsequently, (1,1'-biphenyl)-4-olato)bis(2-methyl-8-quinolinolato)aluminum (hereinafter, "BAlq") was vacuum-deposited with a thickness of 10 nm on the light emitting layer to form a hole blocking layer, and tris-(8-hydroxyquinoline)aluminum (hereinafter, "Alq$_3$") was formed with a thickness of 40 nm to form an electron transport layer. Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 50] Red OLED

The OLEDs were fabricated in the same manner as described in Example 1 except that one of the compounds P-1-2 to P-10-20 according to one embodiment of the present invention described in Table 4 below instead of the compound P-1-1 of the present invention was used as host material of a light emitting layer.

[Comparative Example 1] to [Comparative Example 5] Red OLED

The OLEDs were fabricated in the same manner as described in Example 1 except that one of the Comparative compounds A to E below instead of the compound P-1-1 of the present invention was used as host material of a light emitting layer.

<Comp. compd A>

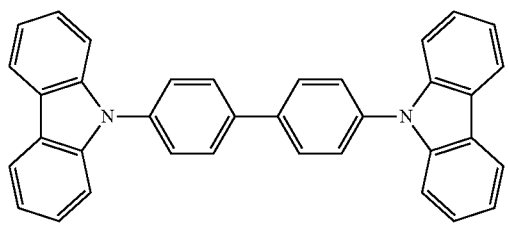

<Comp.compd B>

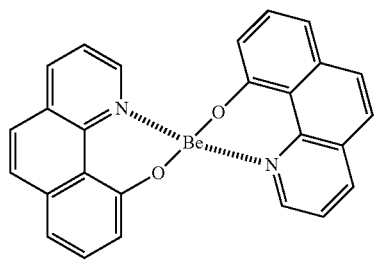

<Comp.compd C>

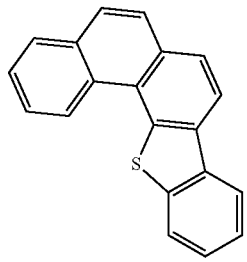

<Comp.compd D>

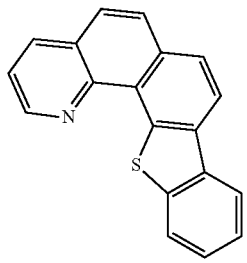

<Comp.compd E>

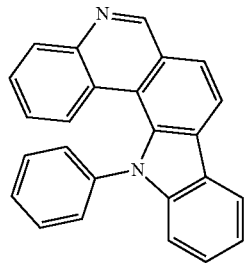

Electroluminescence (EL) characteristics were measured with a PR-650 (Photoresearch) by applying a forward bias DC voltage to the OLEDs prepared in Examples 1 to 50 of the present invention and Comparative Examples 1 to 5. And, the T95 life time was measured using a life time measuring apparatus manufactured by Macscience Inc. at reference brightness of 2500 cd/m$^2$. The measurement results are shown in Tables 4 below.

TABLE 4

| | compound | Voltage (V) | Current Density (mA/cm²) | Brightness (cd/m²) | Efficiency (cd/A) | Lifetime T(95) | CIE (x, y) |
|---|---|---|---|---|---|---|---|
| comp. Ex (1) | Com. (A) | 6.2 | 34.7 | 2500.0 | 7.2 | 69.1 | (0.66, 0.32) |
| comp. Ex (2) | Com. (B) | 5.7 | 32.5 | 2500.0 | 7.7 | 73.1 | (0.67, 0.32) |
| comp. Ex (3) | Com. (C) | 5.5 | 30.1 | 2500.0 | 8.3 | 90.8 | (0.66, 0.32) |
| comp. Ex (4) | Com. (D) | 5.3 | 27.5 | 2500.0 | 9.1 | 96.4 | (0.66, 0.35) |
| comp. Ex (5) | Com. (E) | 5.1 | 26.3 | 2500.0 | 9.5 | 98.1 | (0.66, 0.35) |
| Ex. (1) | Com. (P-1-1) | 4.6 | 17.8 | 2500.0 | 14.0 | 112.5 | (0.65, 0.35) |
| Ex. (2) | Com. (P-1-8) | 4.5 | 17.9 | 2500.0 | 14.0 | 112.5 | (0.65, 0.35) |
| Ex. (3) | Com. (P-1-14) | 4.6 | 18.5 | 2500.0 | 13.5 | 110.7 | (0.66, 0.35) |
| Ex. (4) | Com. (P-1-15) | 4.6 | 19.3 | 2500.0 | 13.0 | 118.3 | (0.66, 0.35) |
| Ex. (5) | Com. (P-1-18) | 4.8 | 17.2 | 2500.0 | 14.5 | 118.5 | (0.66, 0.35) |
| Ex. (6) | Com. (P-2-1) | 4.4 | 15.4 | 2500.0 | 16.2 | 121.3 | (0.66, 0.35) |
| Ex. (7) | Com. (P-2-8) | 4.4 | 16.4 | 2500.0 | 15.3 | 127.1 | (0.66, 0.35) |
| Ex. (8) | Com. (P-2-14) | 4.5 | 16.3 | 2500.0 | 15.3 | 121.0 | (0.66, 0.35) |
| Ex. (9) | Com. (P-2-15) | 4.4 | 16.1 | 2500.0 | 15.6 | 120.1 | (0.66, 0.35) |
| Ex. (10) | Com. (P-2-18) | 4.4 | 15.4 | 2500.0 | 16.3 | 120.3 | (0.66, 0.35) |
| Ex. (11) | Com. (P-3-1) | 4.6 | 18.6 | 2500.0 | 13.5 | 112.4 | (0.66, 0.35) |
| Ex. (12) | Com. (P-3-8) | 4.5 | 20.0 | 2500.0 | 12.5 | 110.8 | (0.66, 0.35) |
| Ex. (13) | Com. (P-3-14) | 4.6 | 20.3 | 2500.0 | 12.3 | 113.4 | (0.66, 0.35) |
| Ex. (14) | Com. (P-3-15) | 4.7 | 18.1 | 2500.0 | 13.8 | 116.6 | (0.66, 0.35) |
| Ex. (15) | Com. (P-3-18) | 4.7 | 18.9 | 2500.0 | 13.2 | 112.5 | (0.66, 0.35) |
| Ex. (16) | Com. (P-4-1) | 4.5 | 15.0 | 2500.0 | 16.6 | 127.3 | (0.66, 0.35) |
| Ex. (17) | Com. (P-4-8) | 4.4 | 15.3 | 2500.0 | 16.3 | 122.1 | (0.66, 0.35) |
| Ex. (18) | Com. (P-4-14) | 4.3 | 15.3 | 2500.0 | 16.3 | 126.8 | (0.66, 0.35) |
| Ex. (19) | Com. (P-4-15) | 4.4 | 16.2 | 2500.0 | 15.4 | 126.5 | (0.66, 0.35) |
| Ex. (20) | Com. (P-4-18) | 4.5 | 15.8 | 2500.0 | 15.9 | 128.6 | (0.66, 0.35) |
| Ex. (21) | Com. (P-5-1) | 4.8 | 18.3 | 2500.0 | 13.7 | 115.2 | (0.66, 0.35) |
| Ex. (22) | Com. (P-5-8) | 4.6 | 18.8 | 2500.0 | 13.3 | 119.5 | (0.66, 0.35) |
| Ex. (23) | Com. (P-5-14) | 4.7 | 18.1 | 2500.0 | 13.8 | 114.6 | (0.66, 0.35) |
| Ex. (24) | Com. (P-5-15) | 4.6 | 17.1 | 2500.0 | 14.7 | 118.3 | (0.66, 0.35) |
| Ex. (25) | Com. (P-5-18) | 4.5 | 20.4 | 2500.0 | 12.2 | 112.6 | (0.66, 0.35) |
| Ex. (26) | Com. (P-6-1) | 4.7 | 17.2 | 2500.0 | 14.5 | 119.0 | (0.66, 0.35) |
| Ex. (27) | Com. (P-6-8) | 4.6 | 17.0 | 2500.0 | 14.7 | 118.2 | (0.66, 0.35) |
| Ex. (28) | Com. (P-6-14) | 4.8 | 19.6 | 2500.0 | 12.8 | 111.7 | (0.66, 0.35) |
| Ex. (29) | Com. (P-6-15) | 4.5 | 18.8 | 2500.0 | 13.3 | 119.2 | (0.66, 0.35) |
| Ex. (30) | Com. (P-6-18) | 4.5 | 18.3 | 2500.0 | 13.6 | 115.9 | (0.66, 0.35) |
| Ex. (31) | Com. (P-7-1) | 4.4 | 15.9 | 2500.0 | 15.8 | 122.8 | (0.66, 0.35) |
| Ex. (32) | Com. (P-7-8) | 4.3 | 14.9 | 2500.0 | 16.8 | 123.8 | (0.66, 0.35) |
| Ex. (33) | Com. (P-7-14) | 4.4 | 15.6 | 2500.0 | 16.1 | 127.5 | (0.66, 0.35) |
| Ex. (34) | Com. (P-7-15) | 4.5 | 15.6 | 2500.0 | 16.1 | 128.0 | (0.66, 0.35) |
| Ex. (35) | Com. (P-7-18) | 4.4 | 15.7 | 2500.0 | 15.9 | 120.5 | (0.66, 0.35) |
| Ex. (36) | Com. (P-8-1) | 4.4 | 16.1 | 2500.0 | 15.5 | 120.5 | (0.66, 0.35) |
| Ex. (37) | Com. (P-8-8) | 4.4 | 14.9 | 2500.0 | 16.8 | 121.9 | (0.66, 0.35) |
| Ex. (38) | Com. (P-8-14) | 4.3 | 15.6 | 2500.0 | 16.1 | 121.7 | (0.66, 0.35) |
| Ex. (39) | Com. (P-8-15) | 4.4 | 15.8 | 2500.0 | 15.8 | 120.5 | (0.66, 0.35) |
| Ex. (40) | Com. (P-8-18) | 4.4 | 14.8 | 2500.0 | 16.9 | 129.0 | (0.66, 0.35) |
| Ex. (41) | Com. (P-9-1) | 4.6 | 20.2 | 2500.0 | 12.4 | 119.5 | (0.66, 0.35) |
| Ex. (42) | Com. (P-9-8) | 4.7 | 19.0 | 2500.0 | 13.2 | 118.5 | (0.66, 0.35) |
| Ex. (43) | Com. (P-9-14) | 4.7 | 18.5 | 2500.0 | 13.5 | 116.6 | (0.66, 0.35) |
| Ex. (44) | Com. (P-9-15) | 4.6 | 17.3 | 2500.0 | 14.5 | 119.2 | (0.66, 0.35) |
| Ex. (45) | Com. (P-9-18) | 4.7 | 17.1 | 2500.0 | 14.6 | 115.4 | (0.66, 0.35) |
| Ex. (46) | Com. (P-10-1) | 4.6 | 17.5 | 2500.0 | 14.3 | 119.6 | (0.66, 0.35) |
| Ex. (47) | Com. (P-10-8) | 4.7 | 18.4 | 2500.0 | 13.6 | 112.8 | (0.66, 0.35) |
| Ex. (48) | Com. (P-10-14) | 4.8 | 19.1 | 2500.0 | 13.1 | 113.9 | (0.66, 0.35) |
| Ex. (49) | Com. (P-10-15) | 4.5 | 18.0 | 2500.0 | 13.9 | 115.1 | (0.66, 0.35) |
| Ex. (50) | Com. (P-10-18) | 4.7 | 16.9 | 2500.0 | 14.8 | 117.6 | (0.66, 0.35) |

From the results of the above table 4, it is found that luminous efficiency gets higher, driving force is lowered and lifetime is remarkably improved when the material for a organic light emitting element of the present invention is used as phosphorescent host material.

That is, Comparative compound C shows better device results than CBP (Comparative compound A) or Bebq₂ (Comparative compound B), wherein CBP is commonly used as a used a host material and Comparative compound C is a structure in which naphthalene is fused to a dibenzothiophene. Further, driving force is lowered and luminous efficiency gets higher when using Comparative compounds D and E as host material rather than Comparative compounds C, wherein Comparative compounds D and E are a structure in which quinoline is fused to a dibenzothiophene and Comparative compounds C is a structure in which naphthalene is fused to a dibenzothiophene.

Further, Comparative compound D and Comparative compound E are different from each other in the position at which quinoline is fused to heterocycle such as dibenzothiophen or cabazole. As a result, it can be seen that the characteristics of the compound and the results of the device are different. This suggests that the characteristics may vary depending on the position where the heterocyclic compound is fused to quinoline and the substitution position of nitrogen.

The compounds of the present invention show better device results than Comparative compounds A to E, wherein the compound of the present invention is similar to Comparative compound E in the position of nitrogen comprised in quinoline and in the fused position of quinoline and heterocyle but differs in that heteroatom is sulfur (S) or oxygen (O), not N. This is teaching that the characteristics of the compound and the results of the device are significantly different depending on the kind of the hetero element.

Among the compounds of the present invention, in particular, the compounds represented by formulas 1-1 to 1-4 show the best device results, wherein the compound is a structure in which $R^{10}$ and $R^{11}$ or $R^{22}$ and $R^{23}$ are bonded to each other to form a ring. It can be explained that this is because the ring-formed compound has a higher thermal stability and an energy level suitable for improving the energy balance in the device.

Although the exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed herein is intended to illustrate the scope of the technical idea of the present invention, and the scope of the present invention is not limited by the embodiments. The scope of the present invention shall be construed on the basis of the accompanying claims, and it shall be construed that all of the technical ideas included within the scope equivalent to the claims belong to the present invention.

The invention claimed is:

1. A compound of formula 1:

[Formula 1]

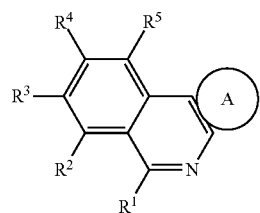

wherein:

$R^1$ is

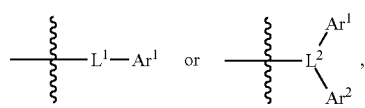

A ring is one of formulas 2 to 4,

<Formula 2>

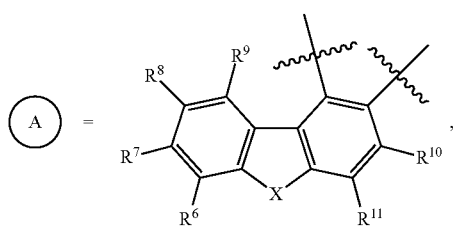

, <Formula 3>

, or <Formula 4>

X is —O— or —S—, $R^2$ to $R^{23}$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, a $C_2$-$C_{20}$ alkenyl group, a $C_1$-$C_{30}$ alkoxyl group and a $C_6$-$C_{30}$ aryloxy group, and neighboring groups of $R^6$ to $R^{23}$ are optionally linked to each other to form a ring, $L^1$ is selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, $L^2$ is selected from the group consisting of a $C_6$-$C_{60}$ arylene group, a fluorenylene group, and a $C_2$-$C_{60}$ heterocyclic group containing at least one heteroatom selected from the group consisting of O, N, S, Si, and P, $Ar^1$ and Are are each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si, and P, and -L'-N($R_a$)($R_b$), in -L'-N($R_a$)($R_b$), L' is selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and $R_a$ and $R_b$ are each independently selected from the group consisting of a $C_6$-$C_{60}$ aryl group, a fluorenyl group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and $R^1$-$R^{23}$, $R_a$, $R_b$, $L^1$, $L^2$, L', $Ar^1$, $Ar^2$, and a ring formed by bonding neighboring groups of $R^6$ to $R^{23}$ to each other are each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

2. The compound of claim 1, wherein the Formula 1 is represented by one of Formulas 5 to 10:

<Formula 5>

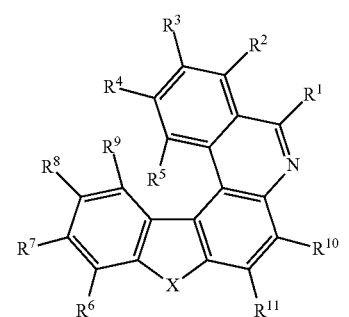

<Formula 6>

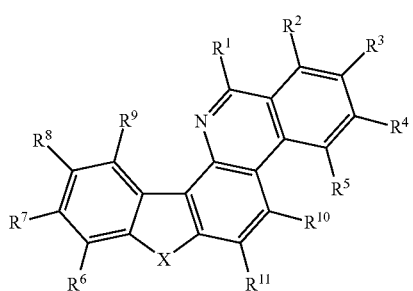

<Formula 7>

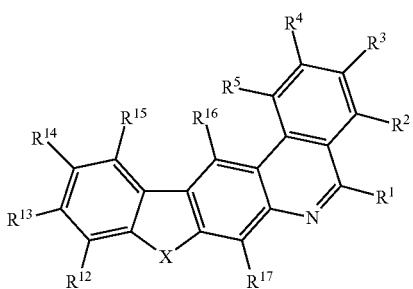

<Formula 8>

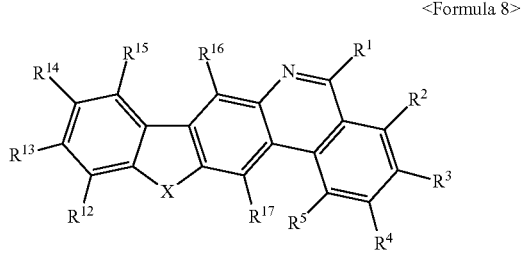

<Formula 9>

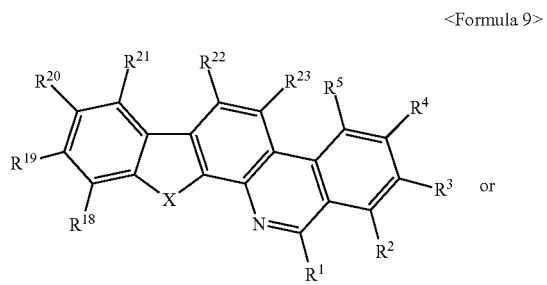

or

<Formula 10>

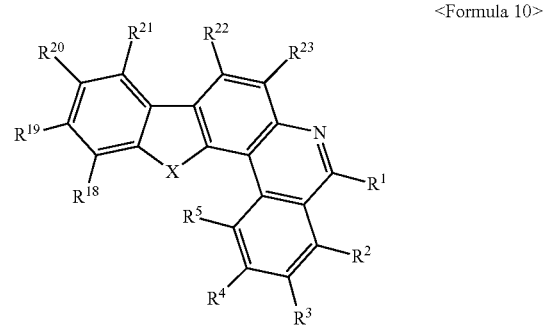

in formulas 5 to 10, X and $R^1$-$R^{23}$ are the same as defined in claim 1.

3. The compound of claim 1, wherein Formula 1 is represented by one of Formulas 1-1 to 1-4:

<Formula 1-1>

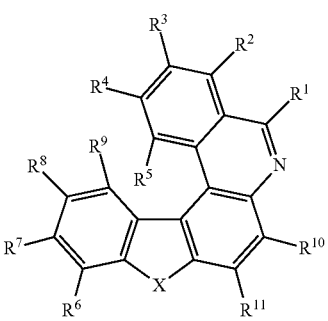

<Formula 1-2>

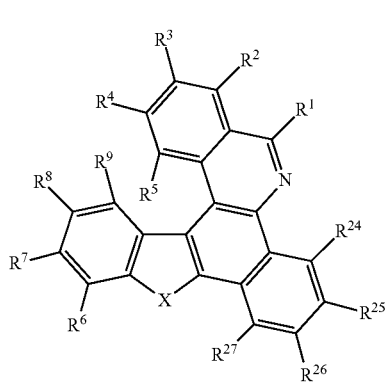

<Formula 1-3>

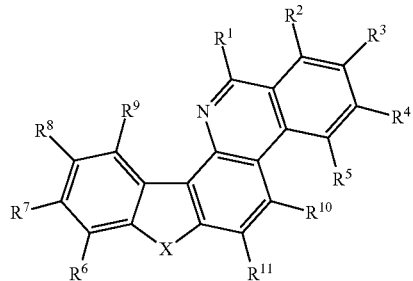

or

<Formula 1-4>

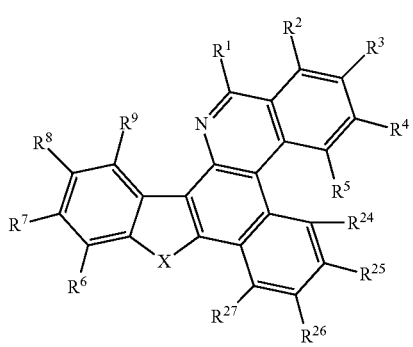

in formulas 1-1 to 1-4, X, $R^1$ to $R^9$, and $R^{18}$ to $R^{21}$ are the same as defined in claim 1, and $R^{24}$ to $R^{27}$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_6$-$C_{60}$ aromatic ring and a $C_3$-$C_{60}$ aliphatic ring, a $C_2$-$C_{20}$ alkenyl group, a $C_1$-$C_{30}$ alkoxyl group, and a $C_6$-$C_{30}$ aryloxy group.

4. The compound of claim 1, wherein the compound represented by Formula 1 is one of the following compounds:

P-1-1

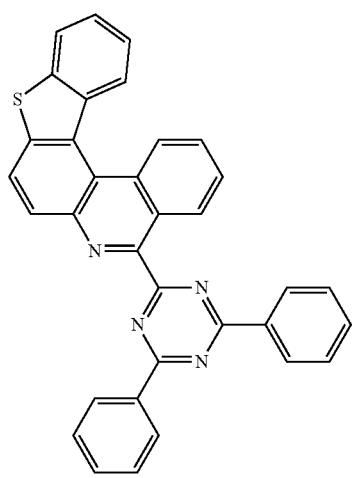

P-1-2

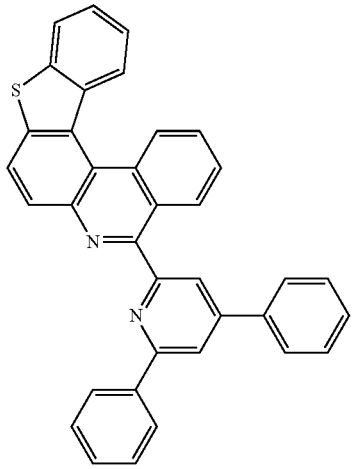

P-1-3

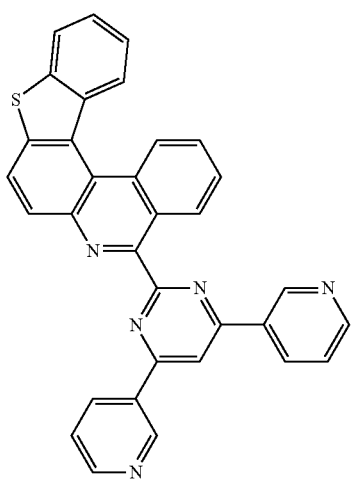

P-1-4

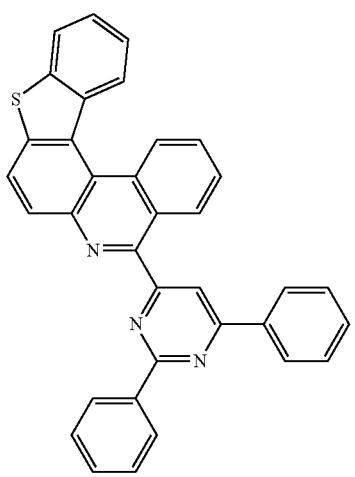

P-1-5
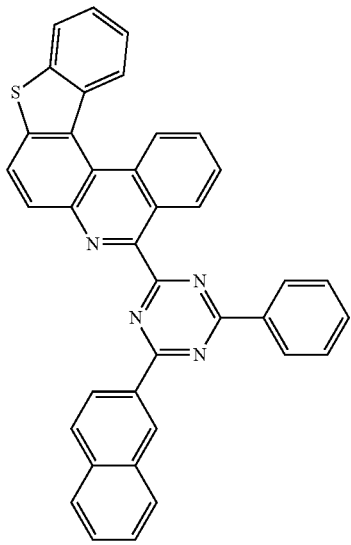
P-1-6
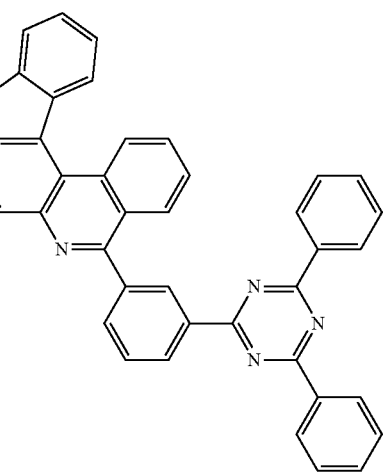
P-1-7
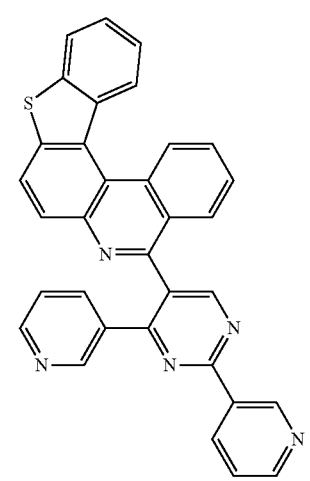
P-1-8
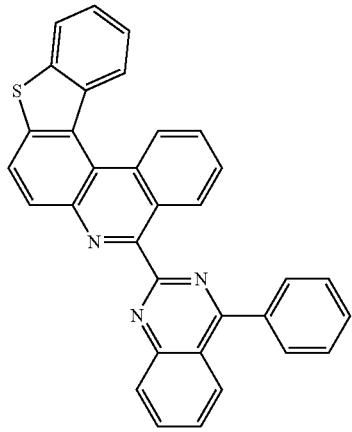
P-1-9
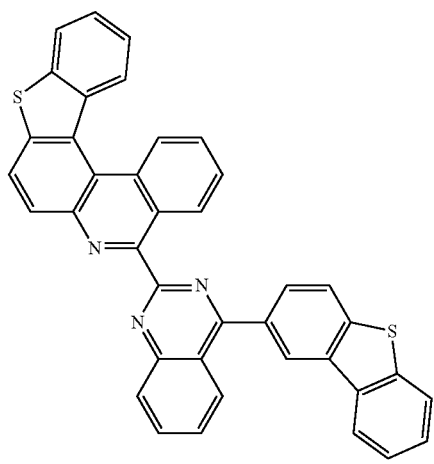
P-1-10
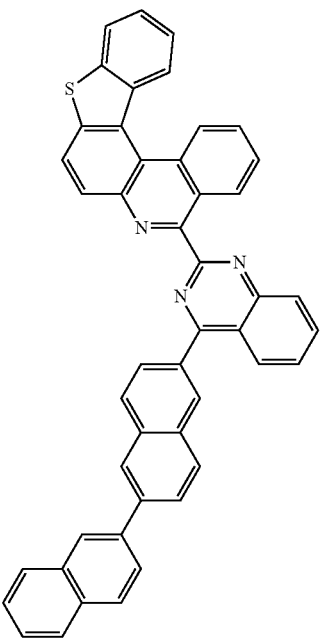

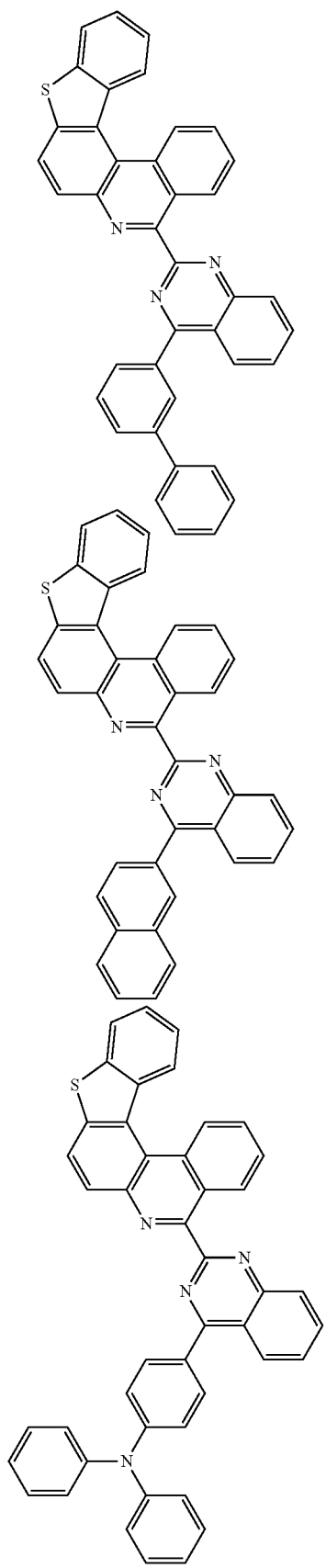
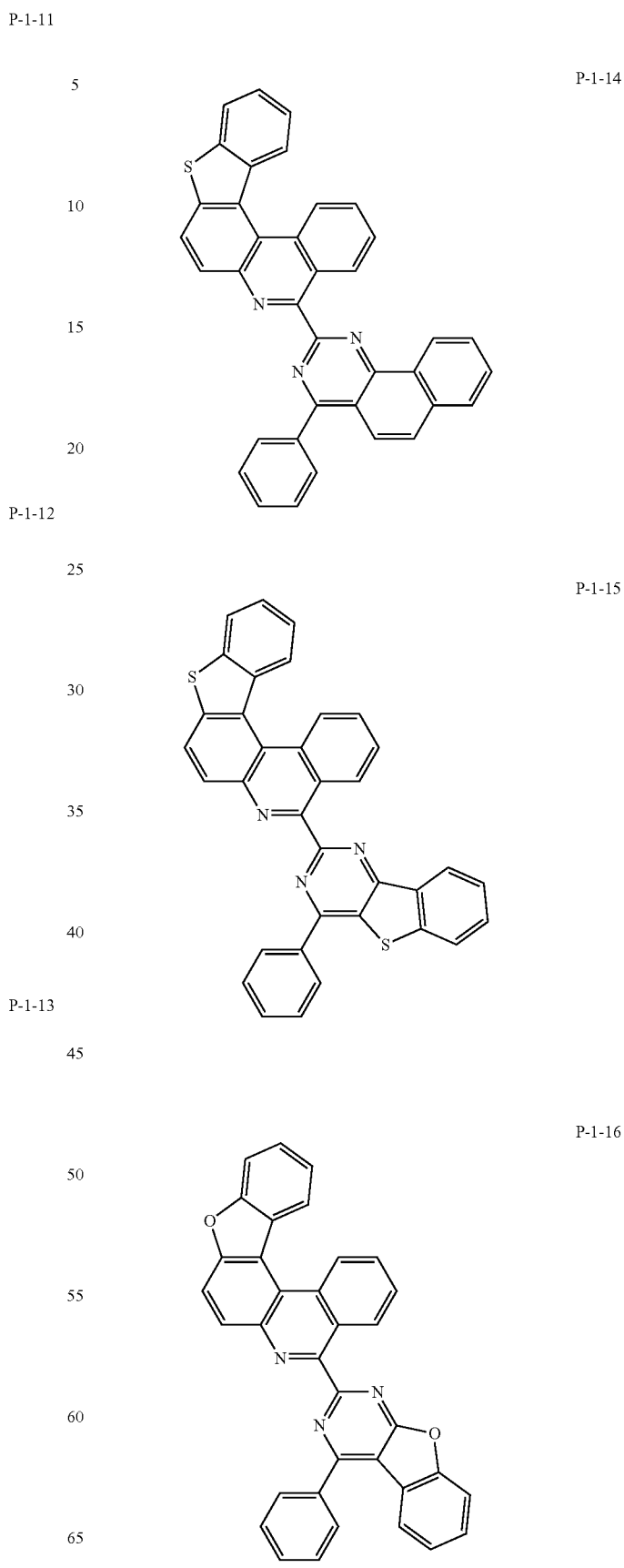

P-1-17
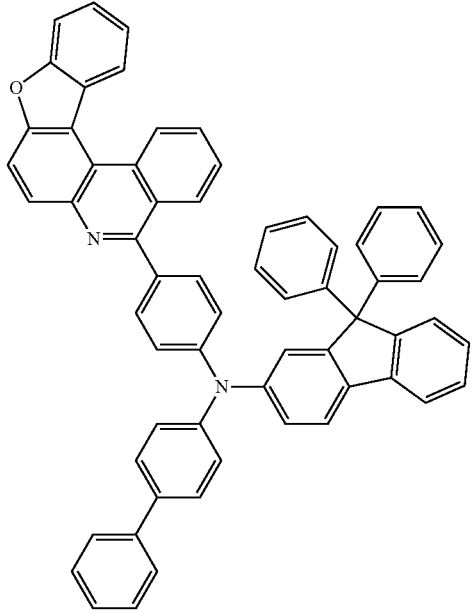
P-1-18
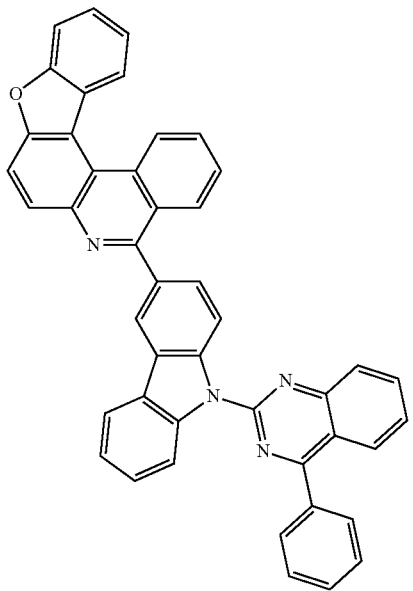
P-1-19
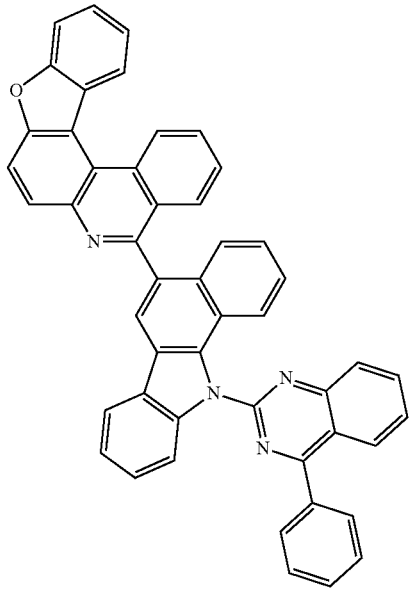
P-1-20
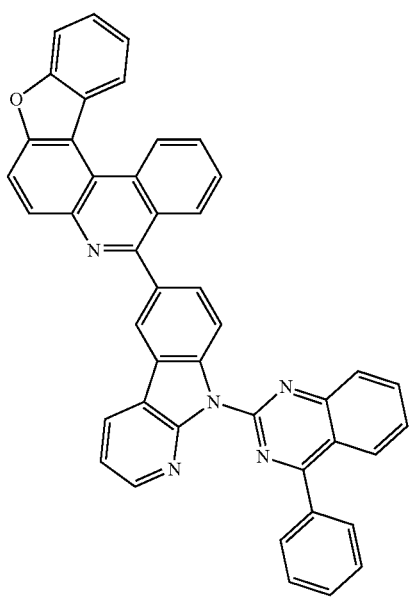
P-2-1
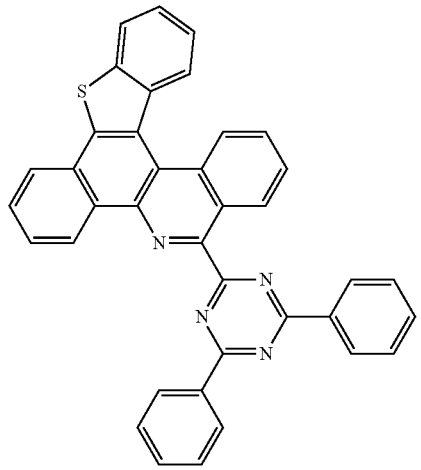

P-2-2
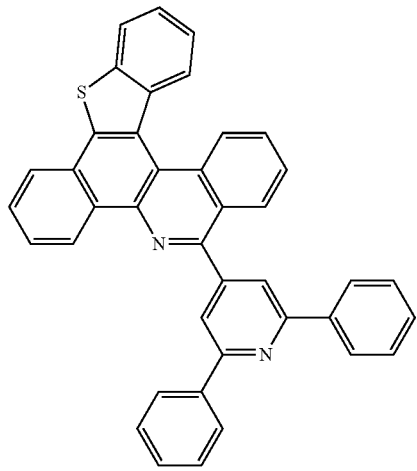
P-2-3
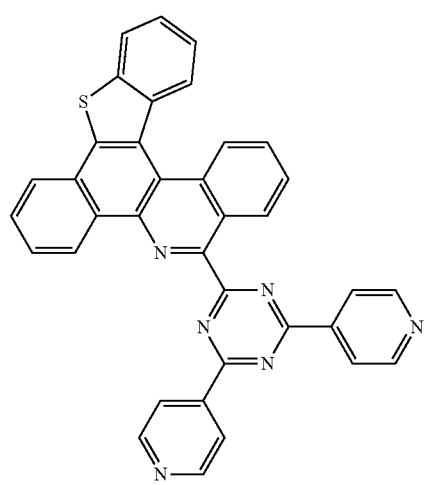
P-2-4
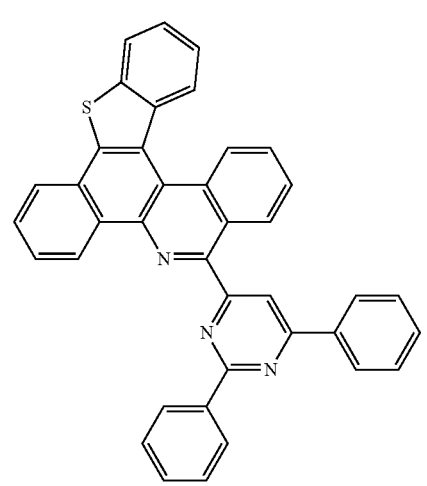
P-2-5
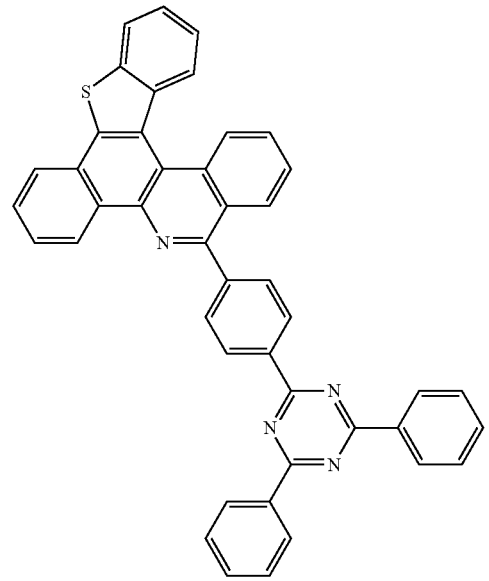
P-2-6
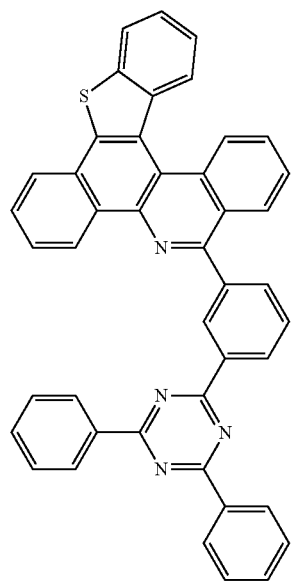
P-2-7
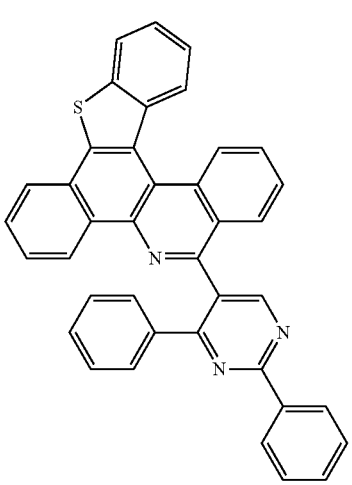

P-2-8
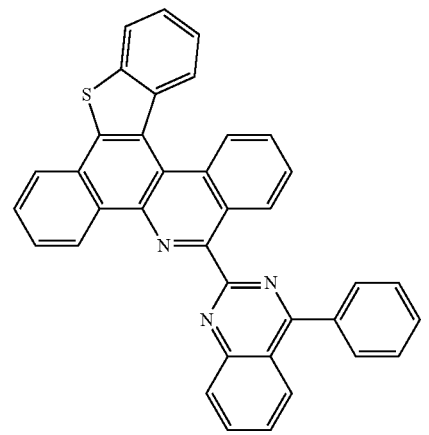
P-2-9
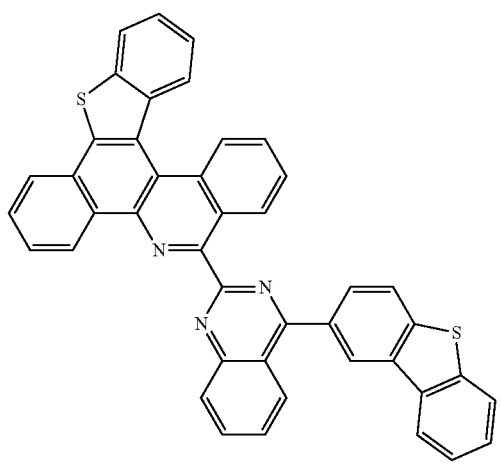
P-2-10
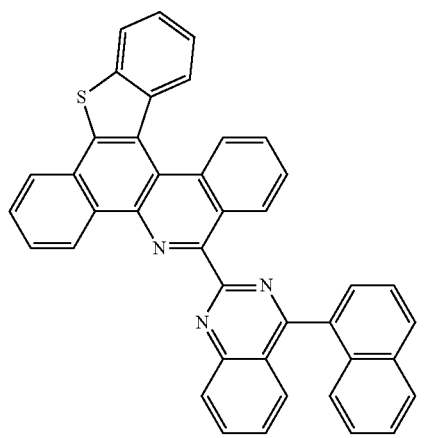
P-2-11
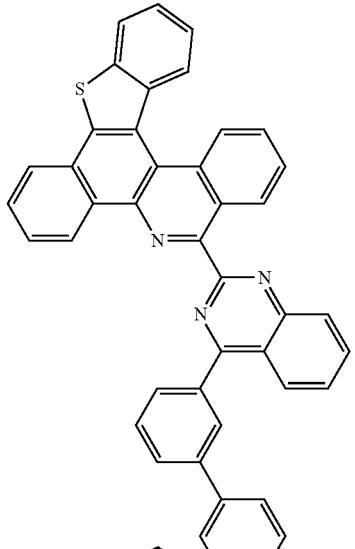
P-2-12
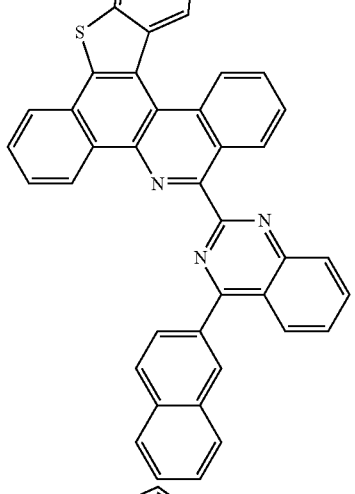
P-2-13
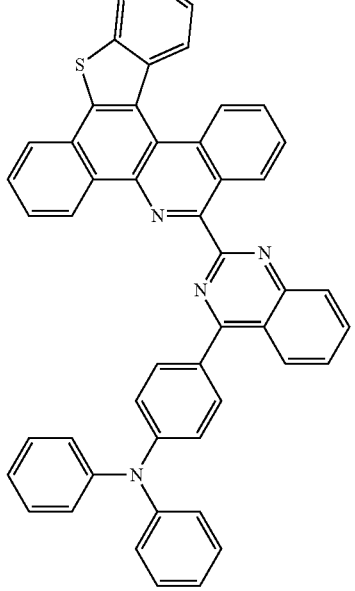

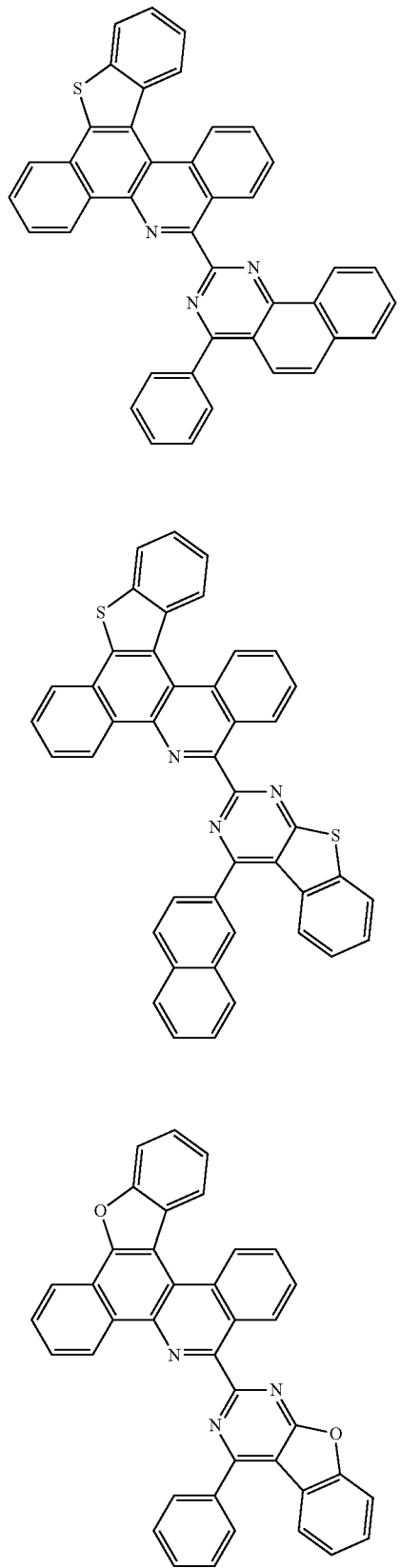

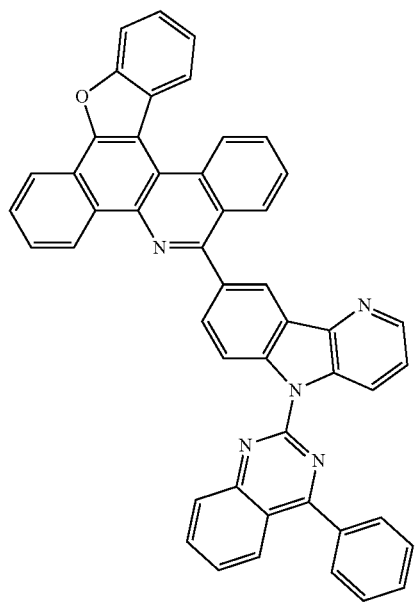
P-2-19
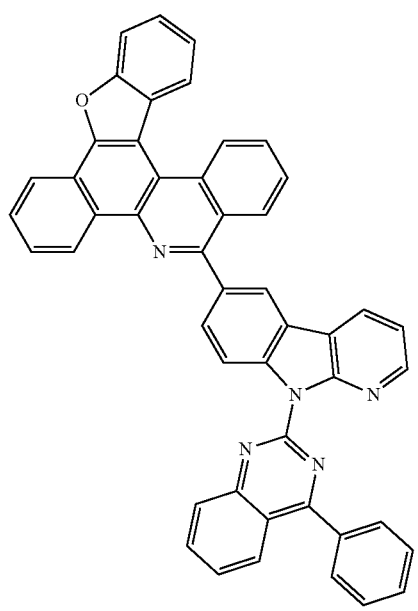
P-2-20
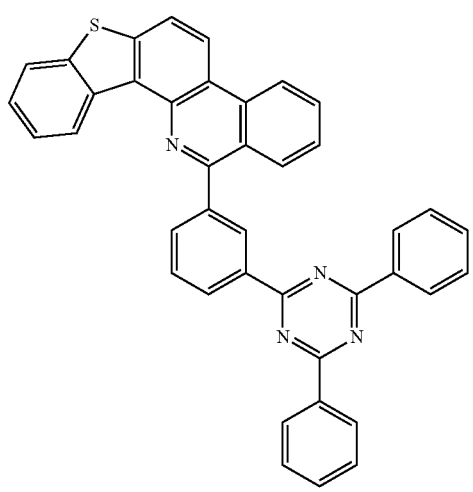
P-3-1
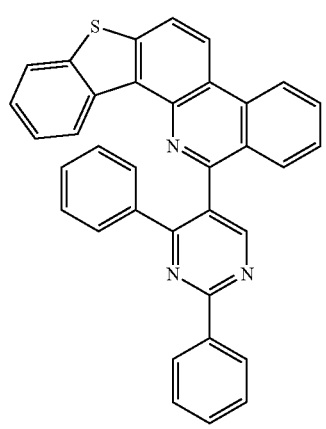
P-3-2
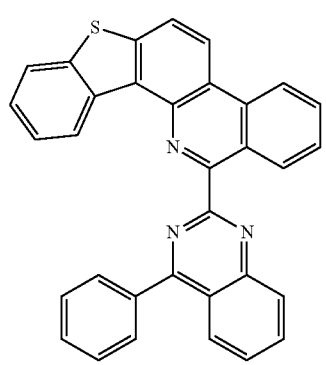
P-3-3

P-3-4
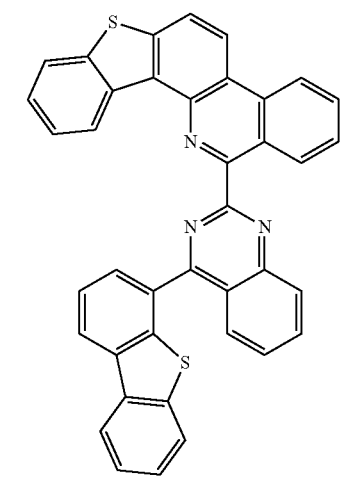
P-3-5
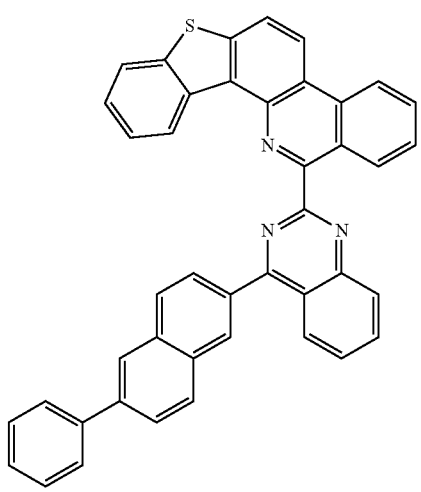
P-3-6
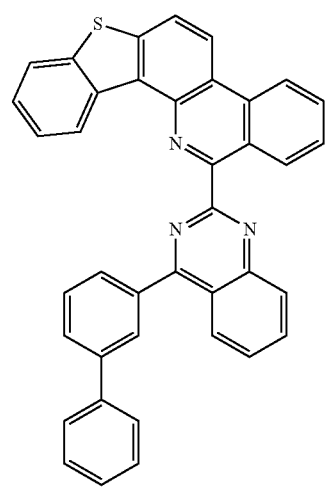
P-3-7
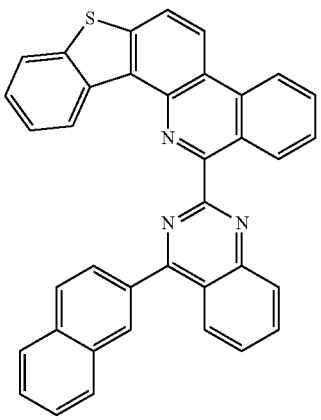
P-3-8
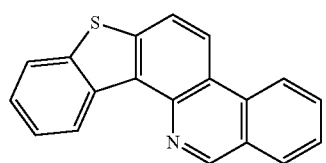
P-3-9
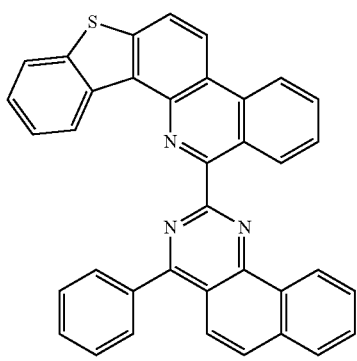
P-3-10
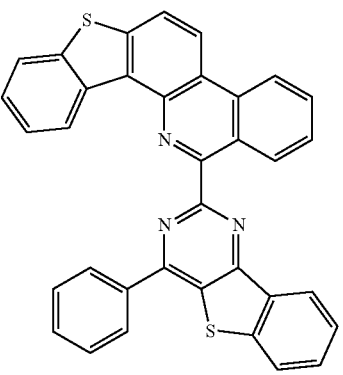

P-3-11
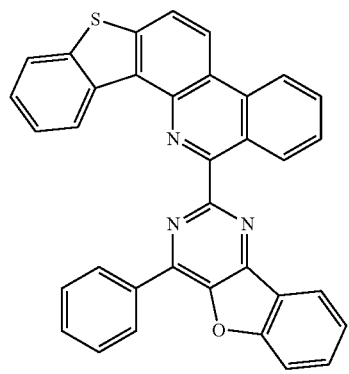
P-3-12
P-3-13
P-3-14
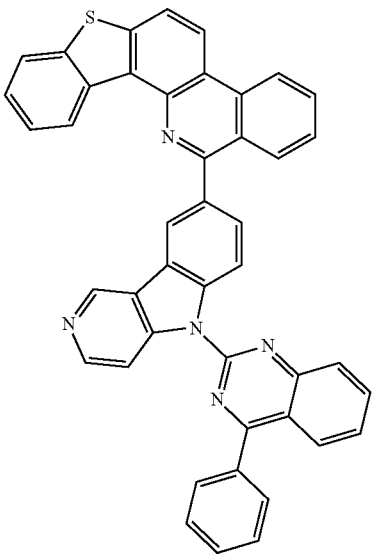
P-3-15
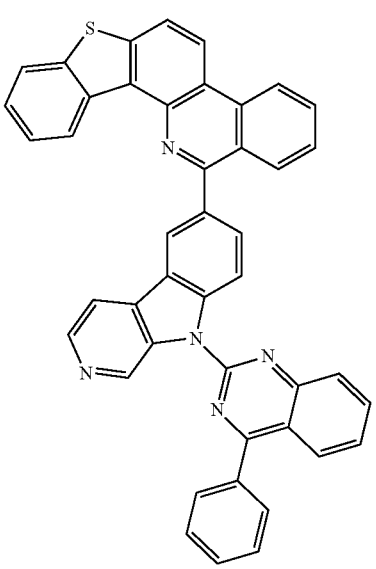
P-3-16
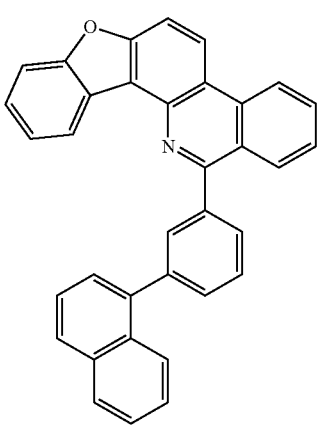

P-3-17
P-3-18
P-3-19
P-3-20
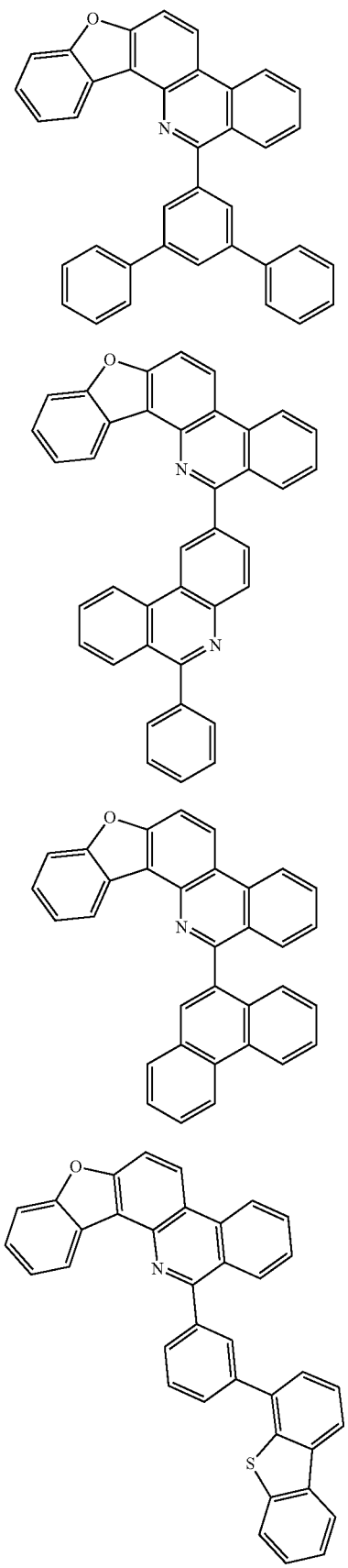
P-4-1
P-4-2
P-4-3
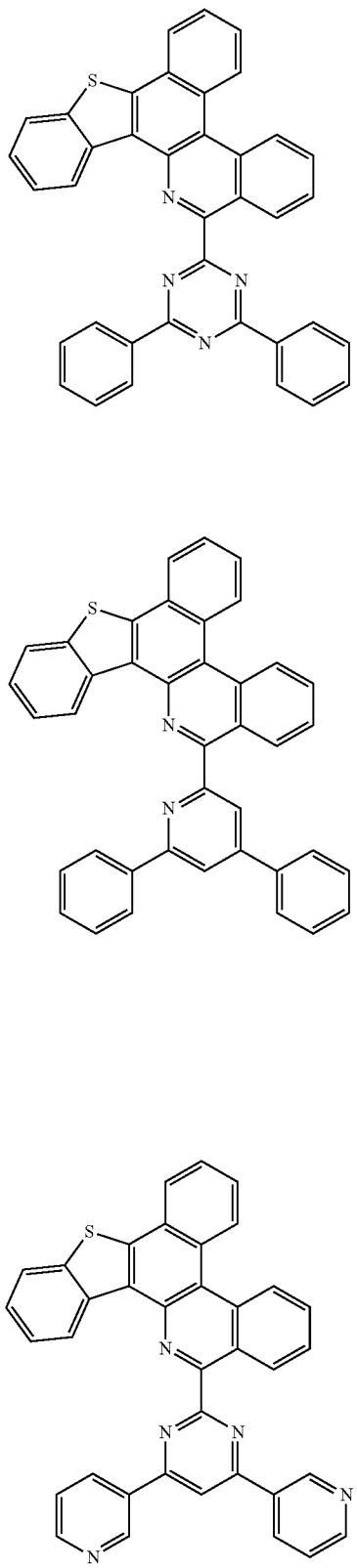

P-4-4
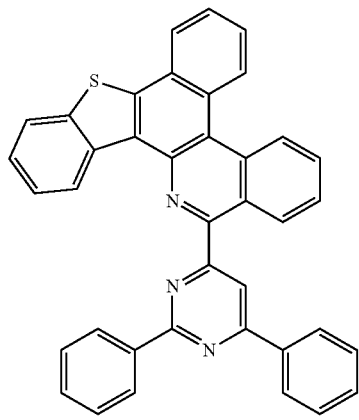
P-4-5
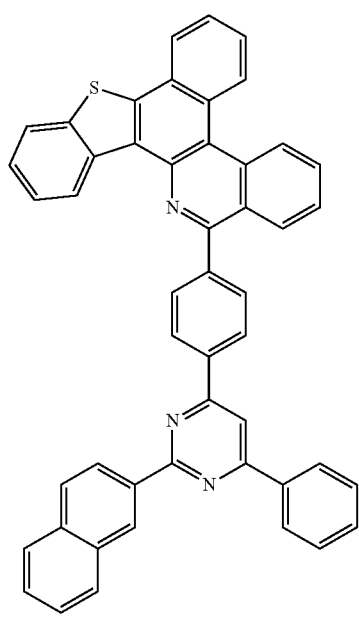
P-4-6
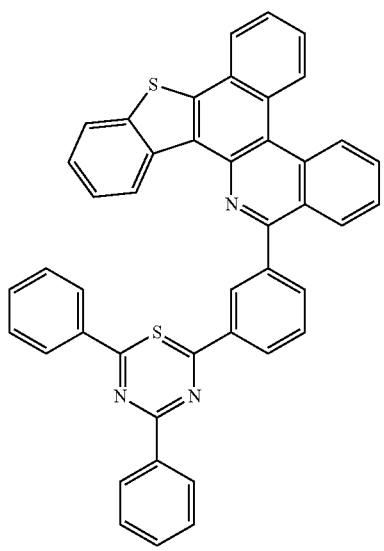
P-4-7
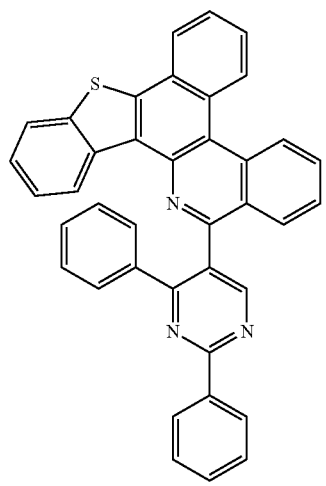
P-4-8
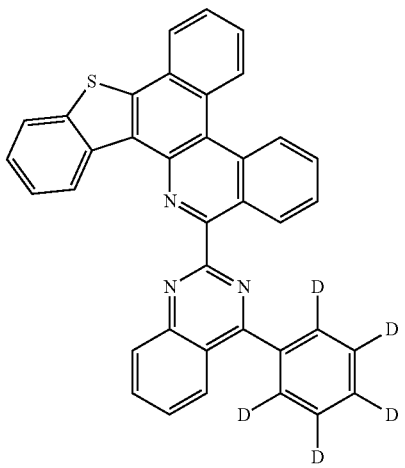
P-4-9
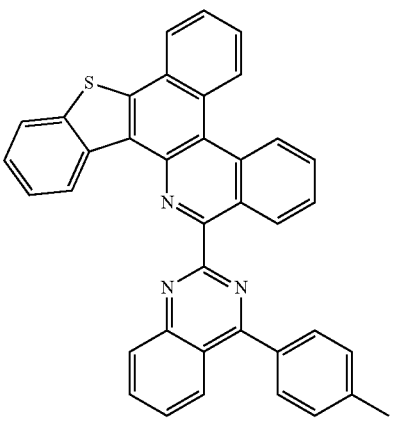

-continued
P-4-10
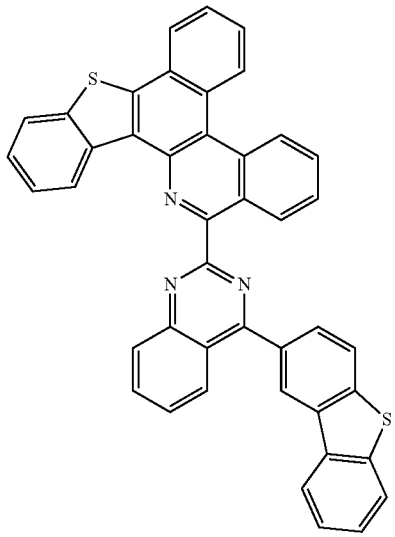
P-4-11
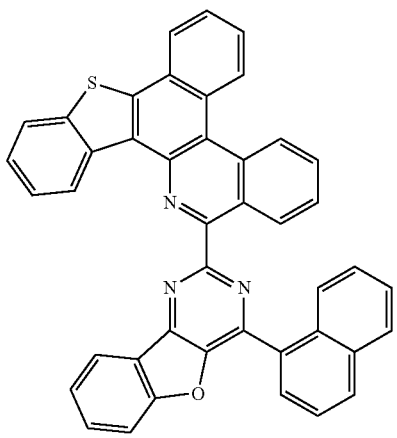
P-4-12
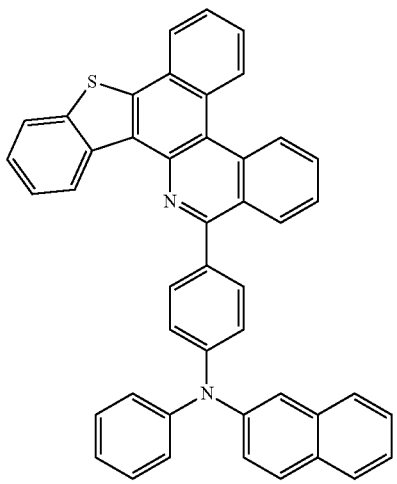
-continued
P-4-13
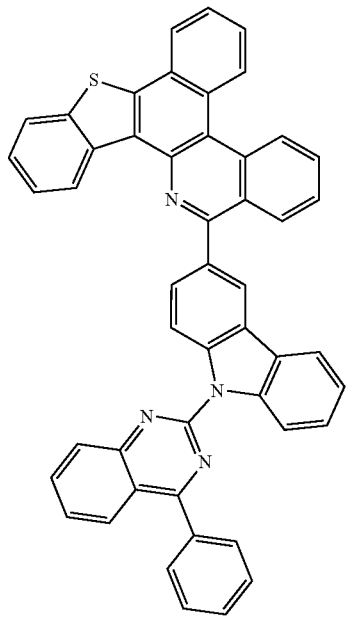
P-4-14
P-4-15

P-4-16
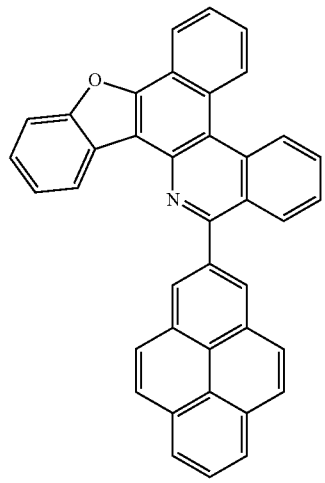
P-4-17
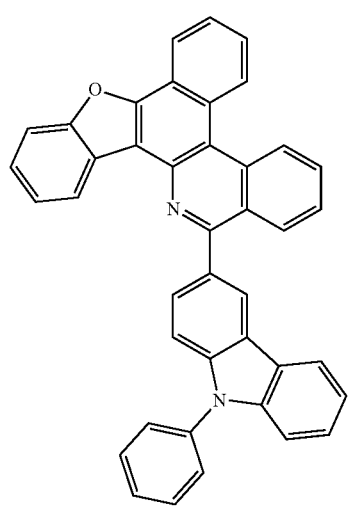
P-4-18
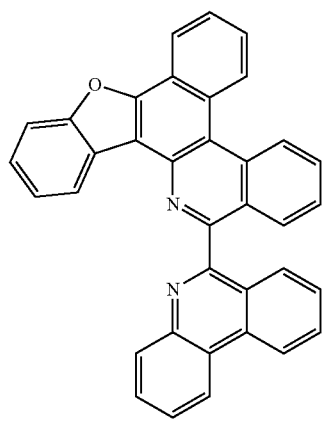
P-4-19
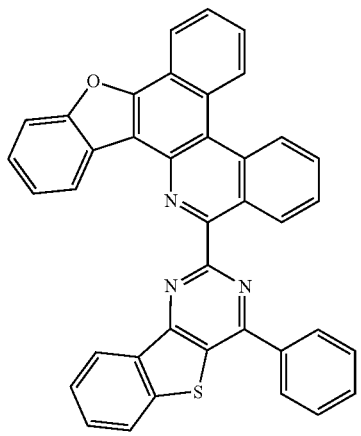
P-4-20
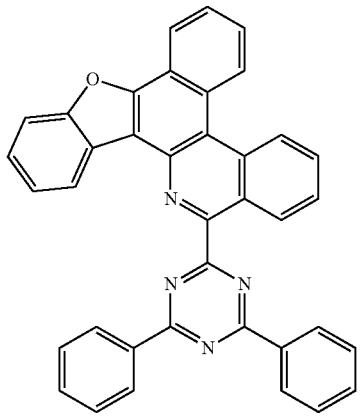
P-5-1
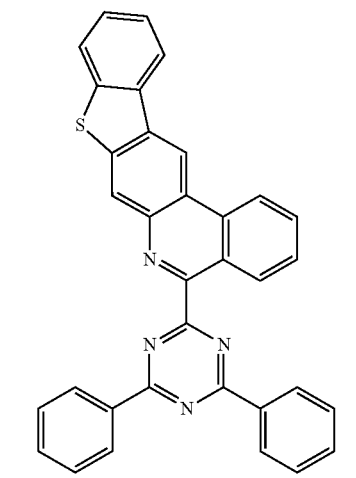

-continued
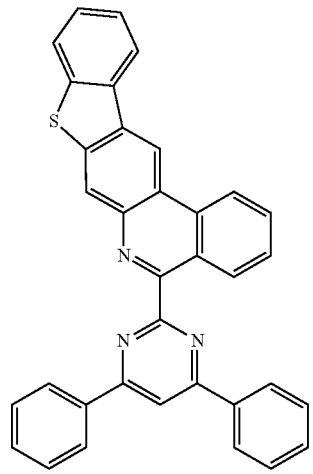
P-5-2
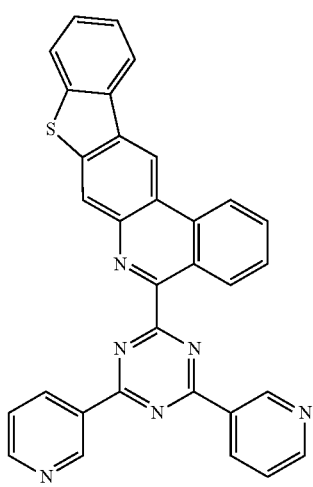
P-5-3
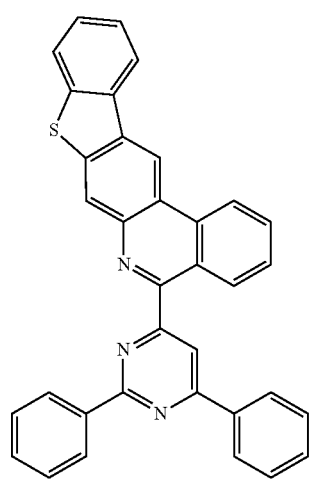
P-5-4
-continued
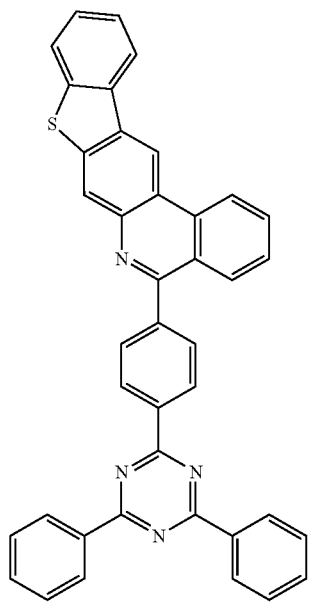
P-5-5
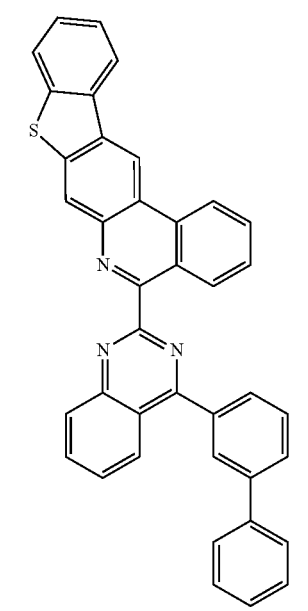
P-5-6

P-5-7
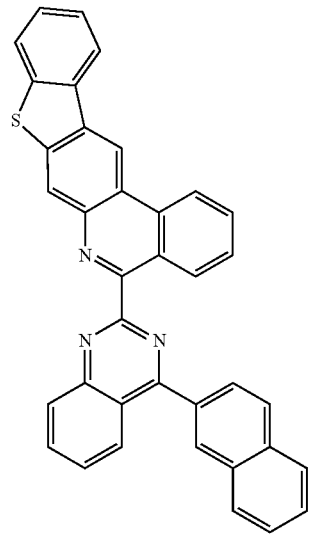
P-5-8
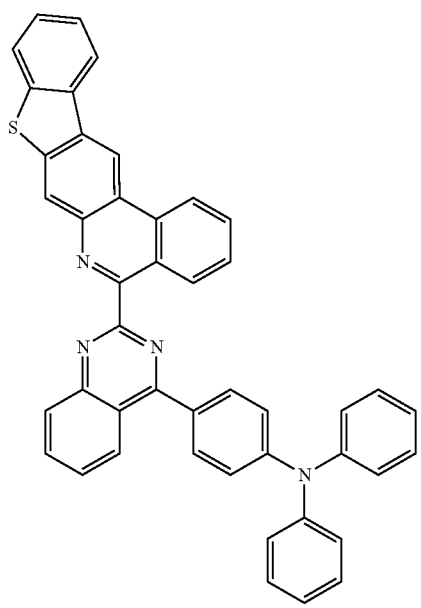
P-5-9
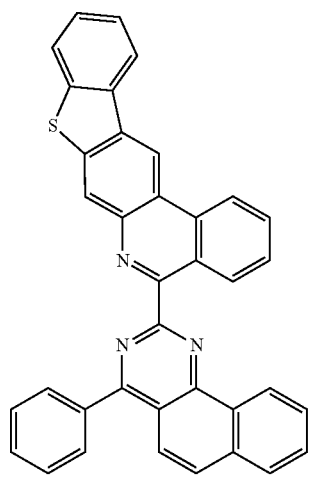
P-5-10
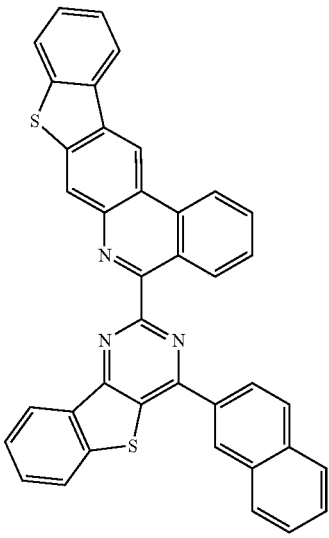
P-5-11
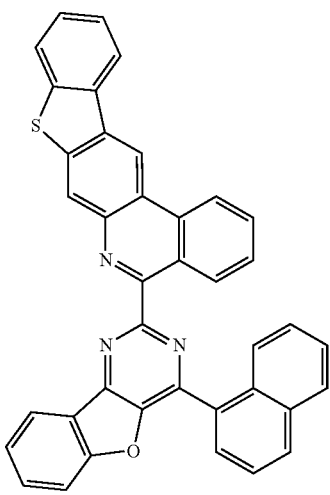
P-5-12
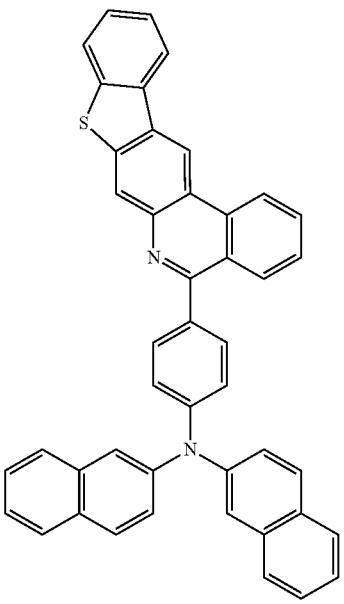

P-5-13
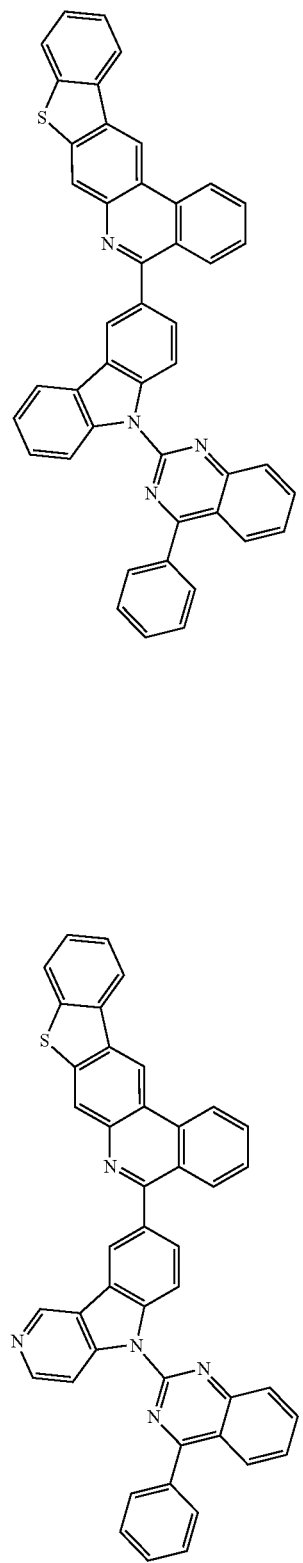
P-5-14
P-5-15
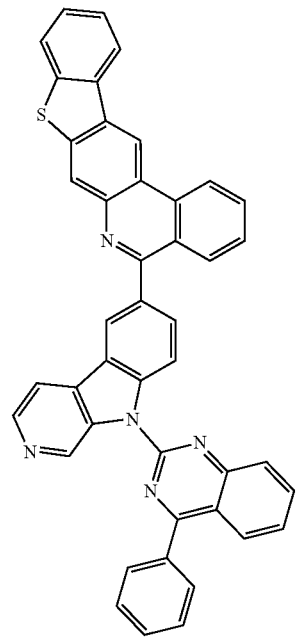
P-5-16
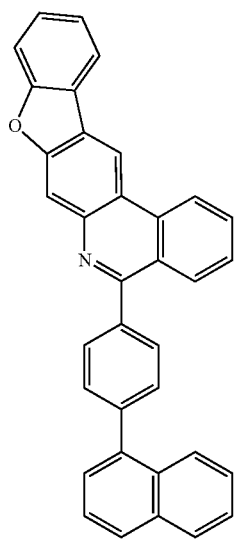
P-5-17
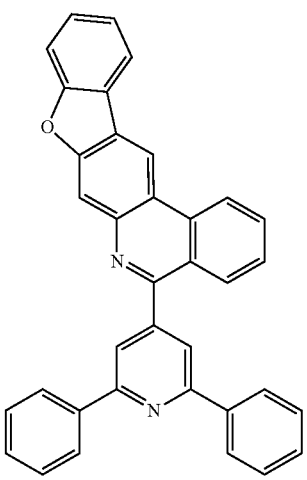

P-5-18
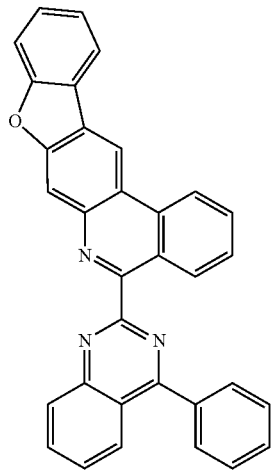
P-6-1
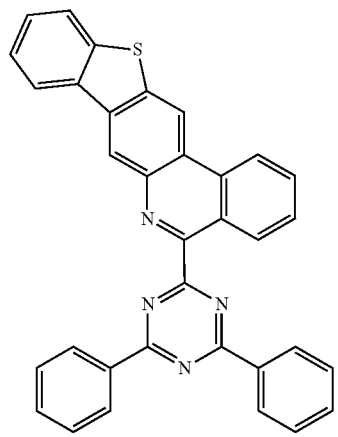
P-5-19
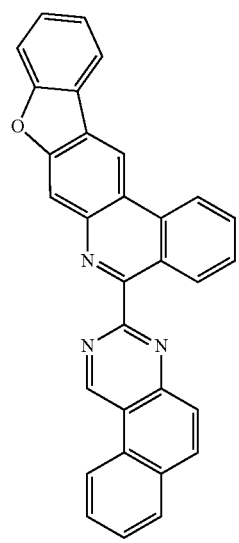
P-6-2
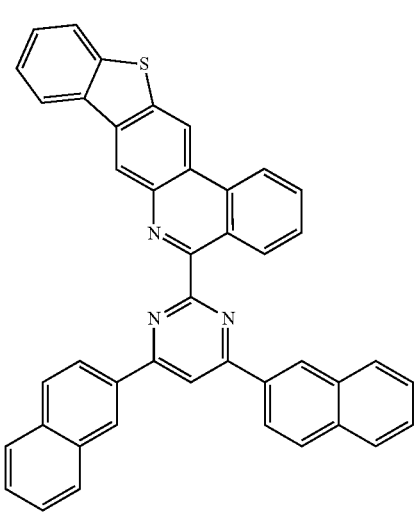
P-5-20
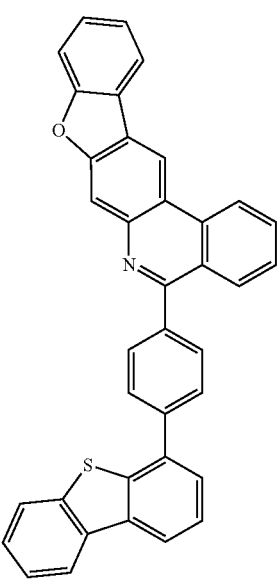
P-6-3
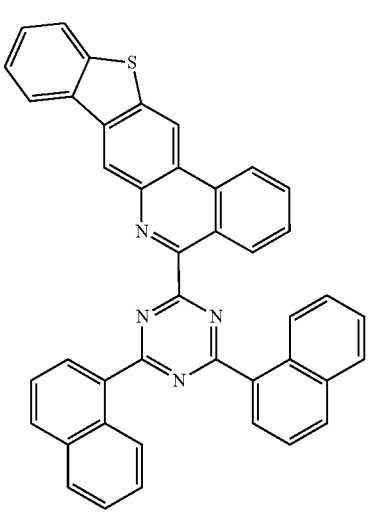

-continued
P-6-4
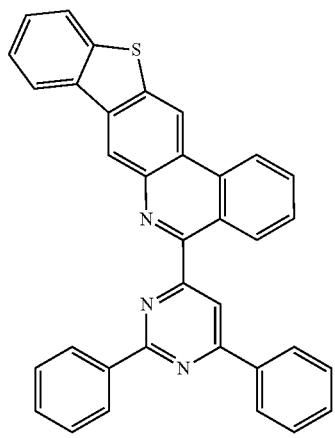
P-6-5
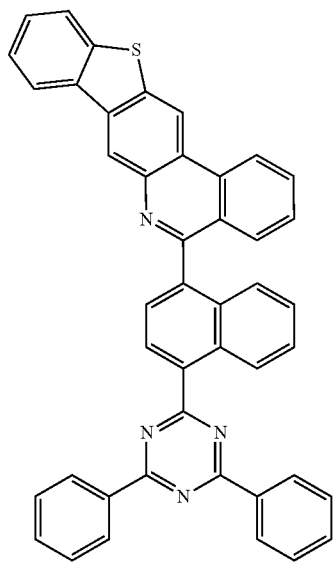
P-6-6
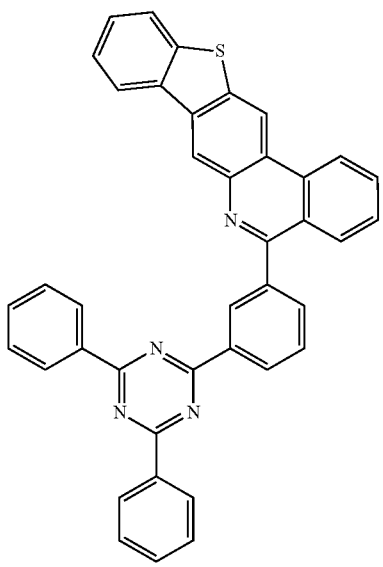
-continued
P-6-7
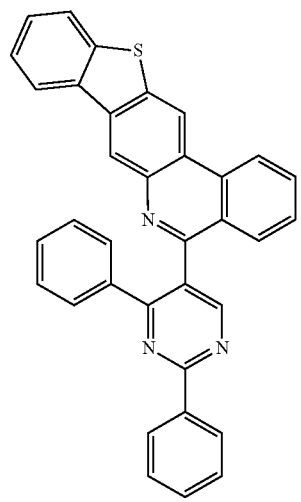
P-6-8
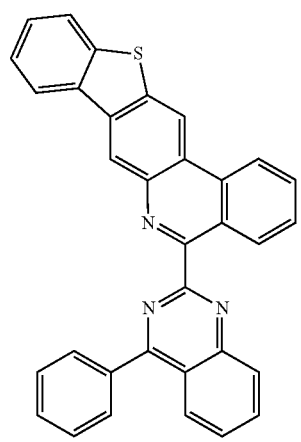
P-6-9
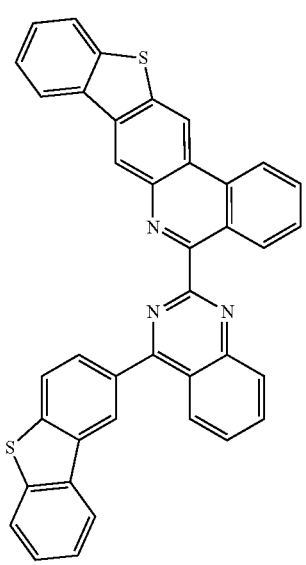

-continued
P-6-10
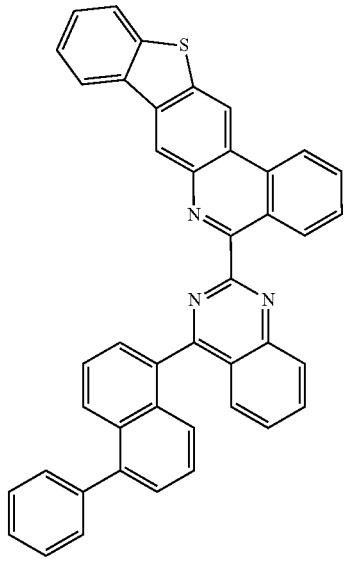
P-6-11
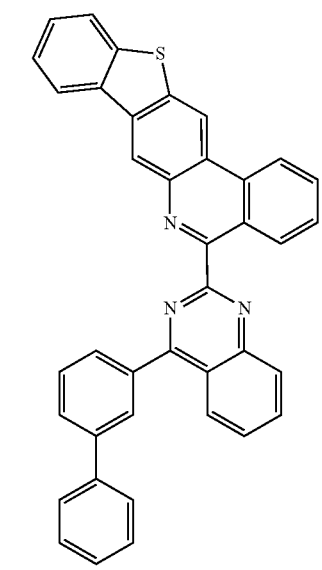
P-6-12
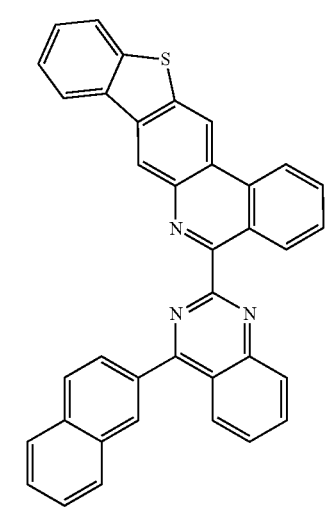
-continued
P-6-13
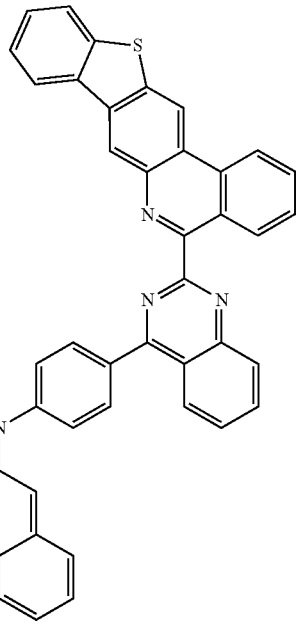
P-6-14
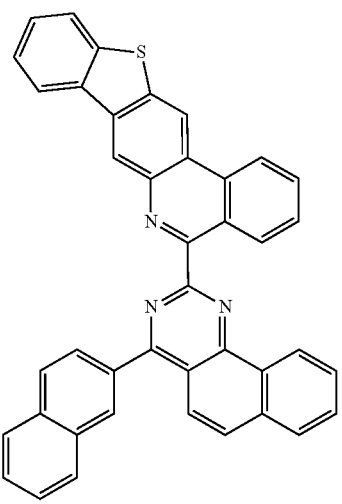
P-6-15
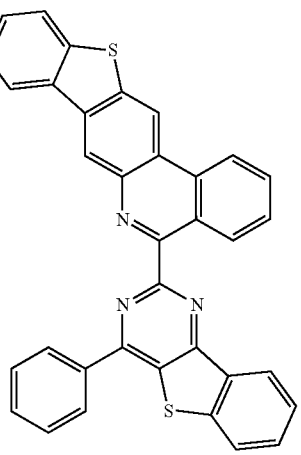

-continued
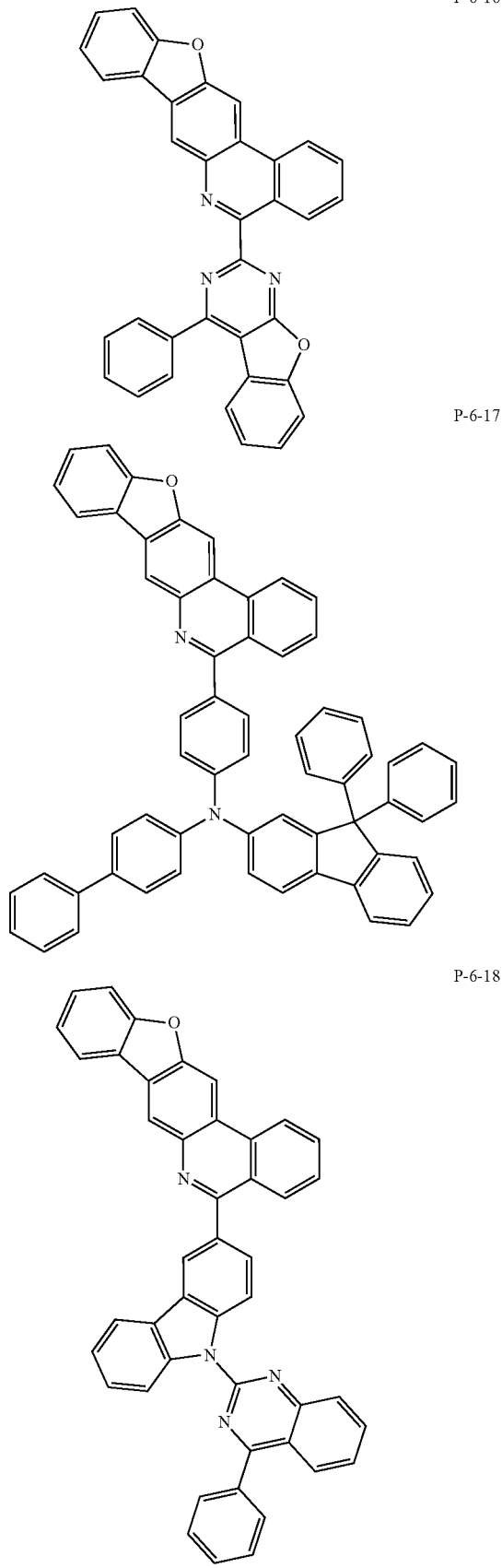
P-6-16
P-6-17
P-6-18
-continued
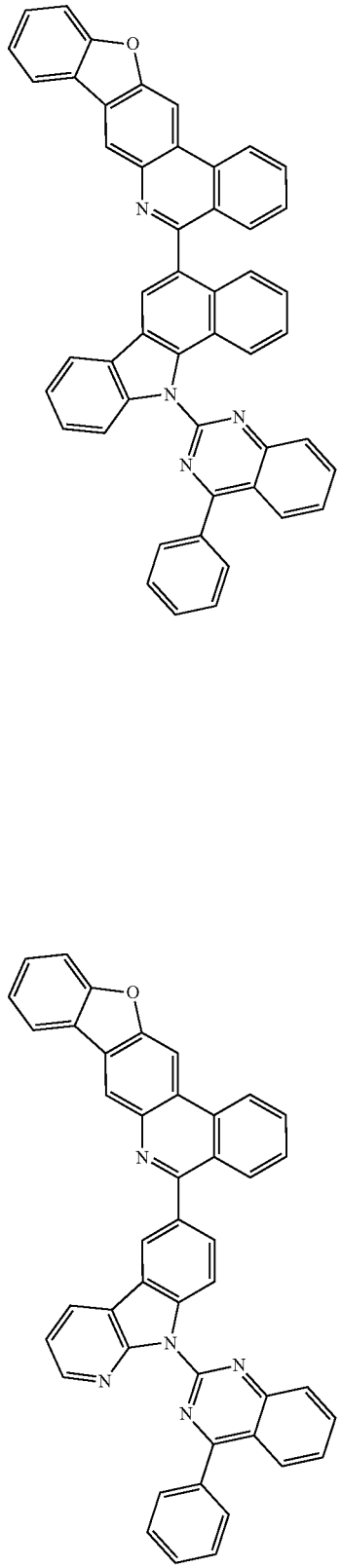
P-6-19
P-6-20

-continued
P-7-1
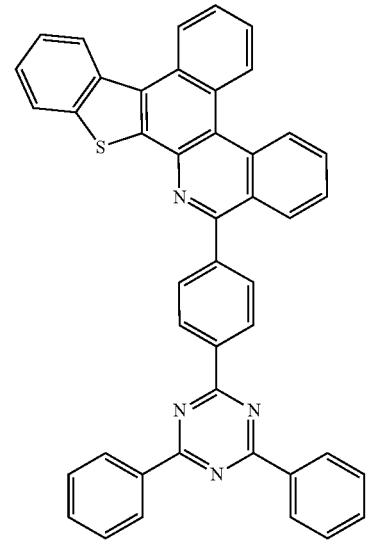
P-7-2
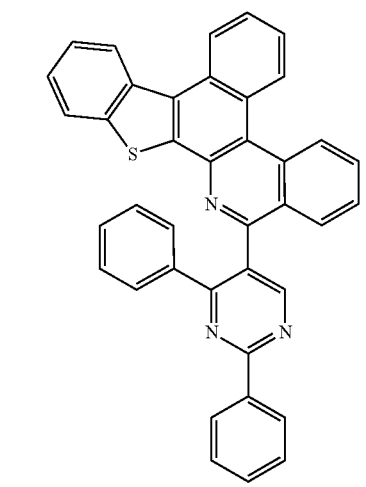
P-7-3
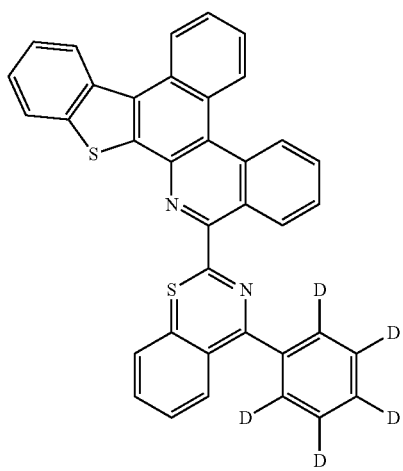
-continued
P-7-4
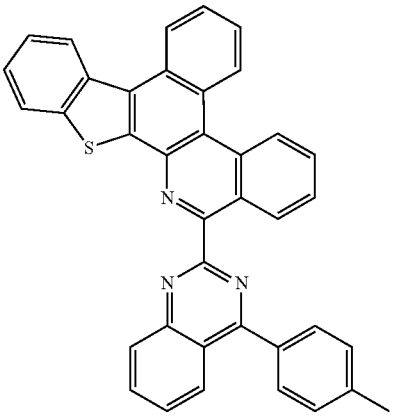
P-7-5
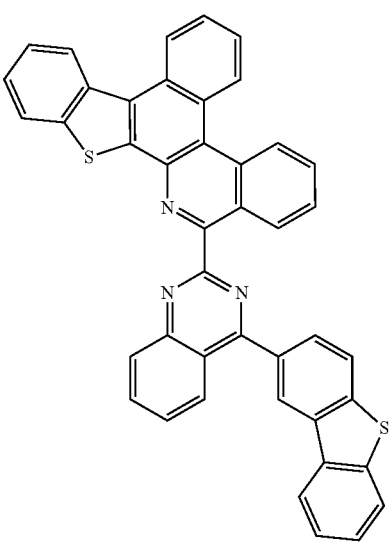
P-7-6
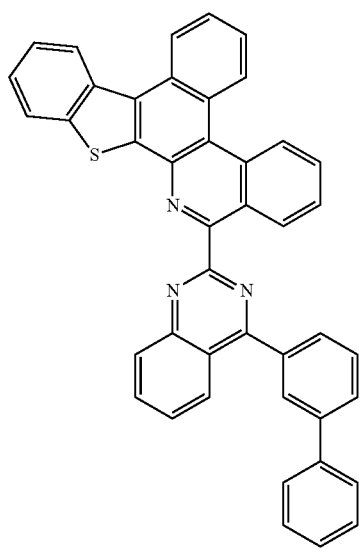

P-7-7
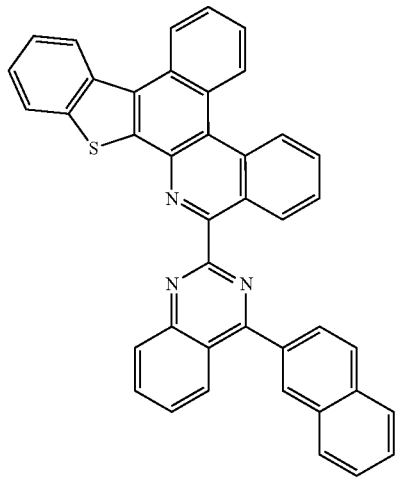
P-7-8
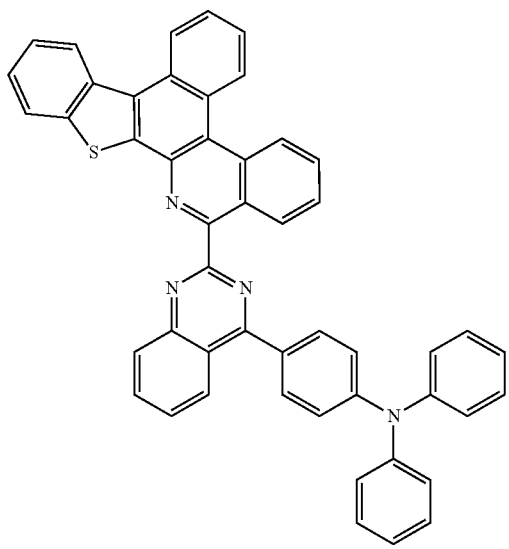
P-7-9
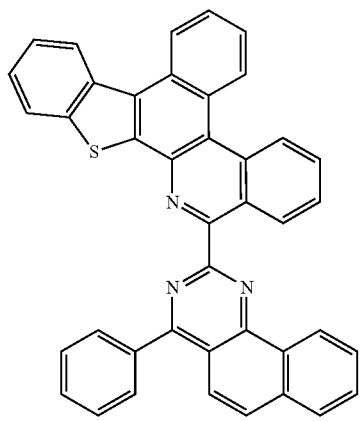
P-7-10
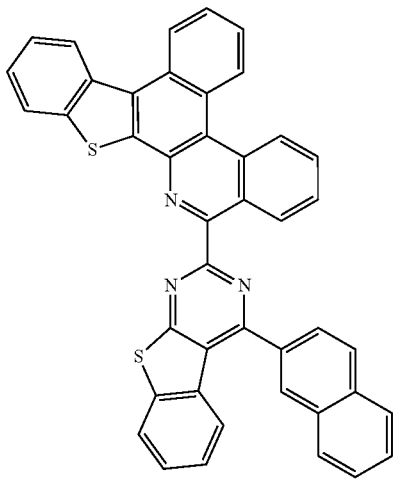
P-7-11
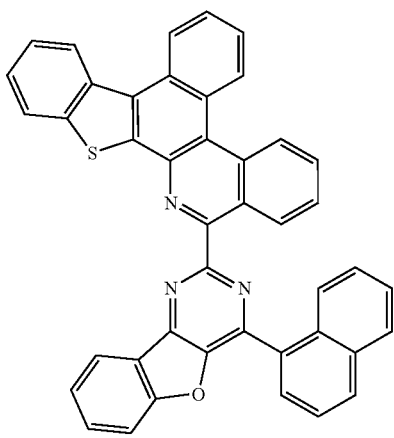
P-7-12
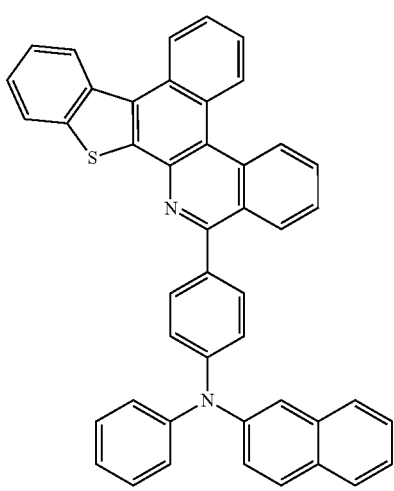

P-7-13
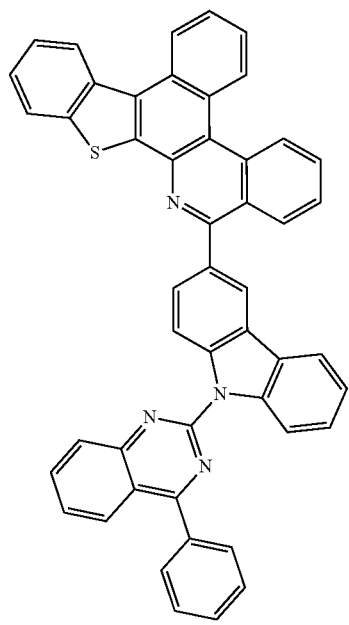
P-7-16
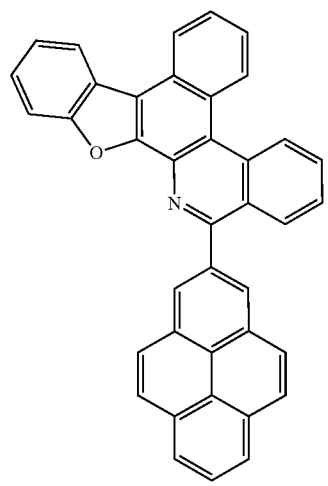
P-7-14
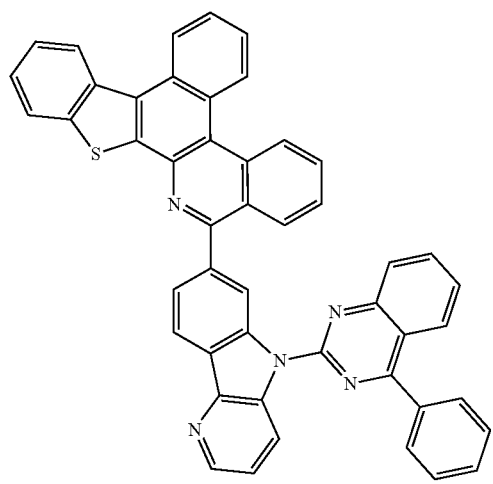
P-7-17
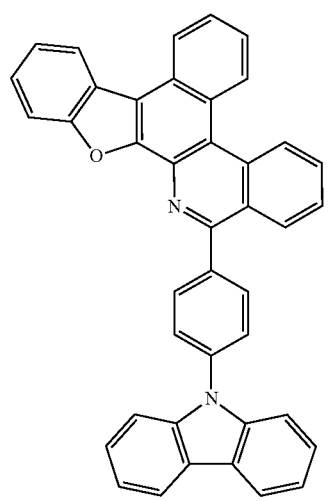
P-7-15
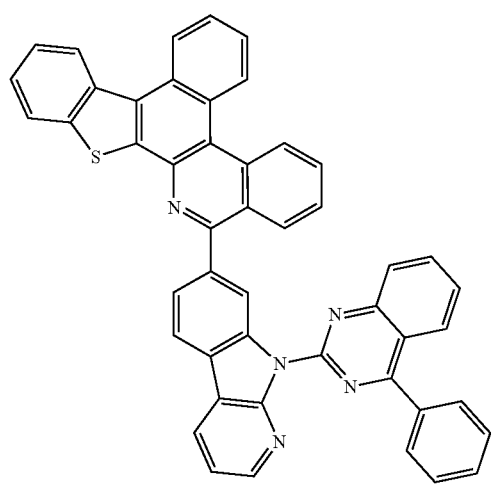
P-7-18
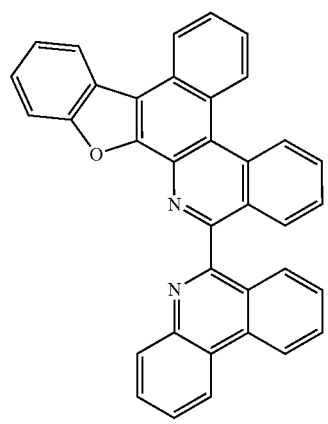

P-7-19
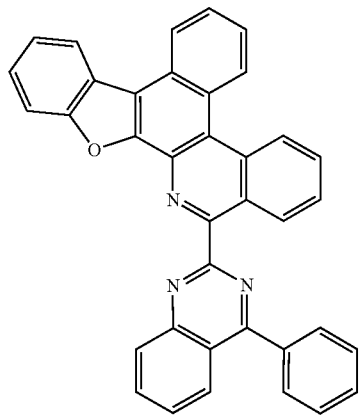
P-7-20
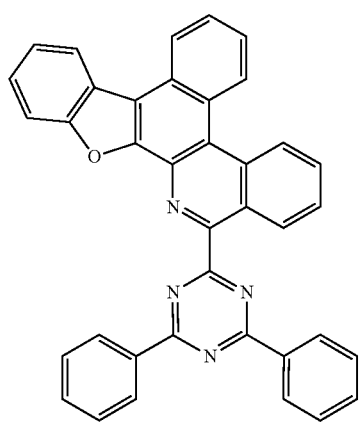
P-8-1
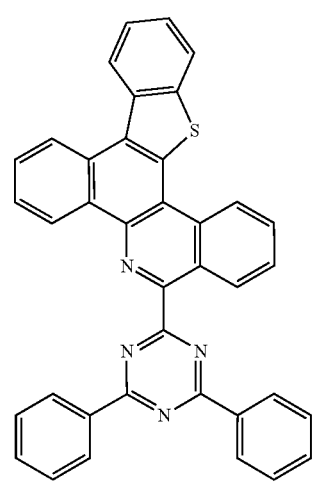
P-8-2
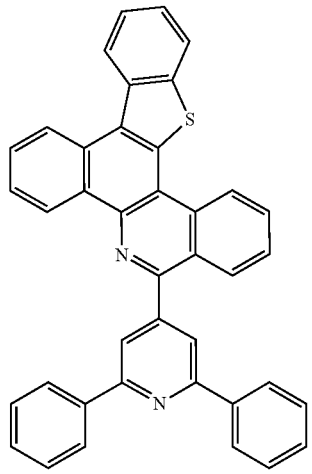
P-8-3
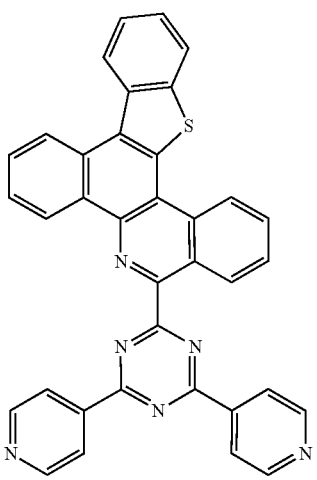
P-8-4
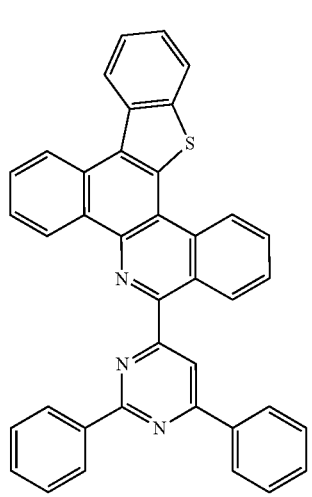

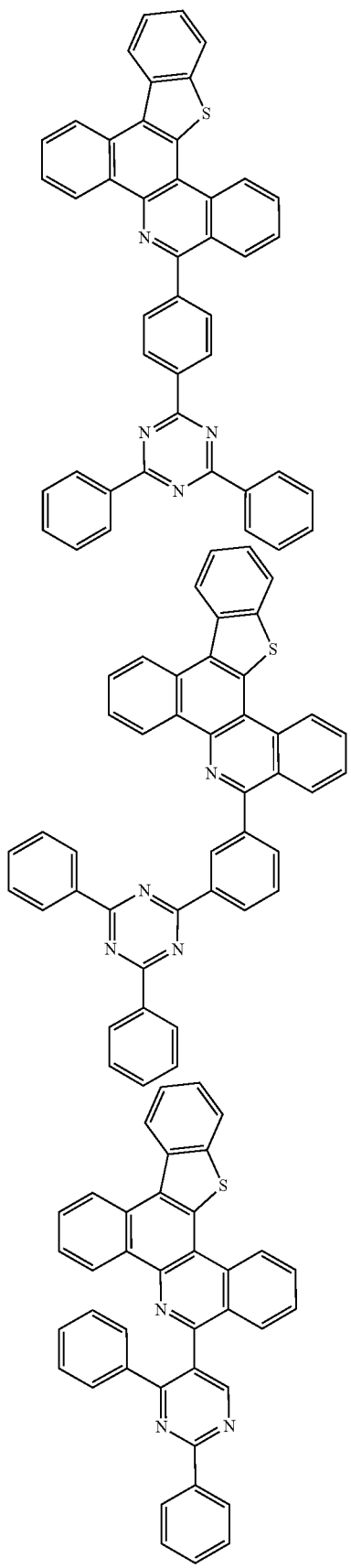
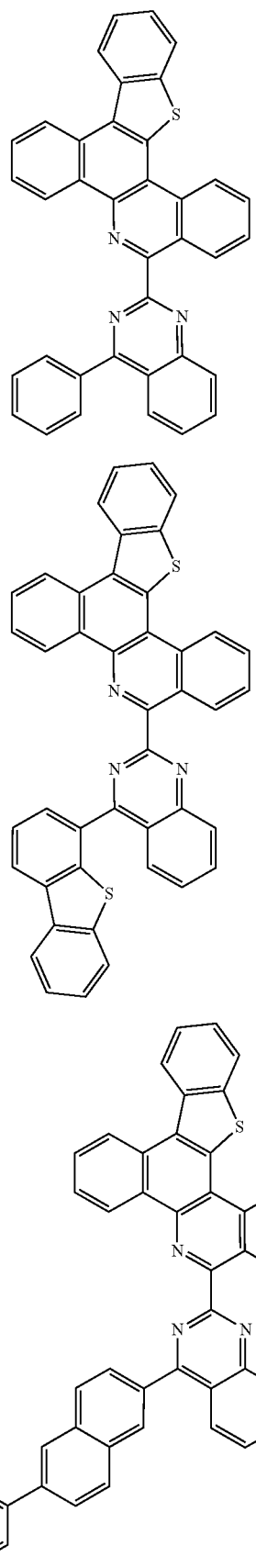

P-8-11
P-8-12
P-8-13
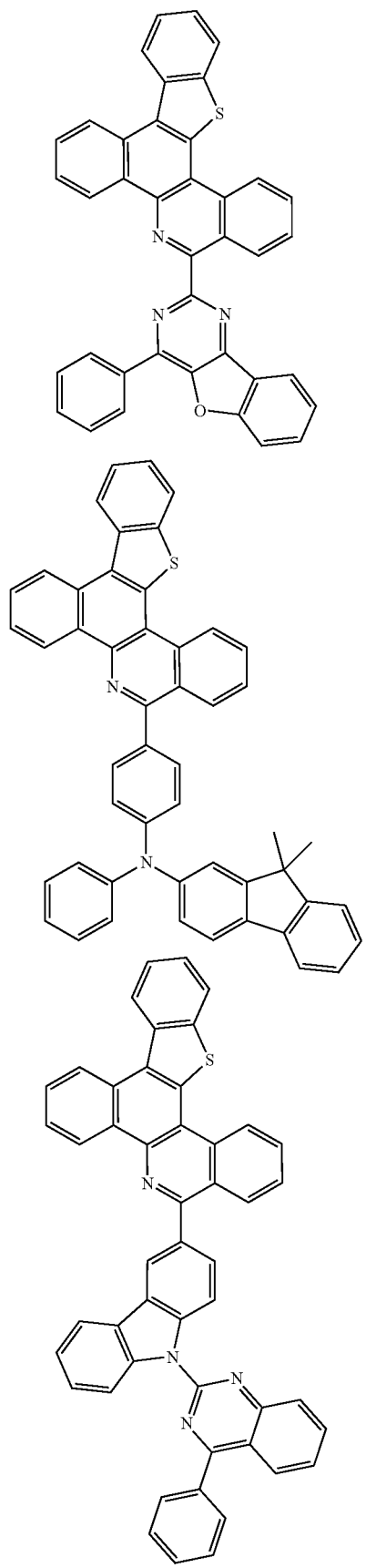
P-8-14
P-8-15
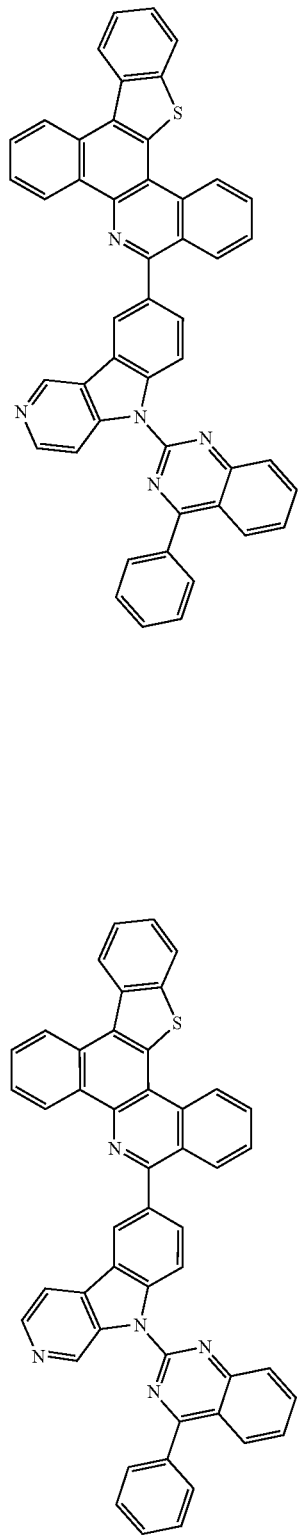

P-8-16
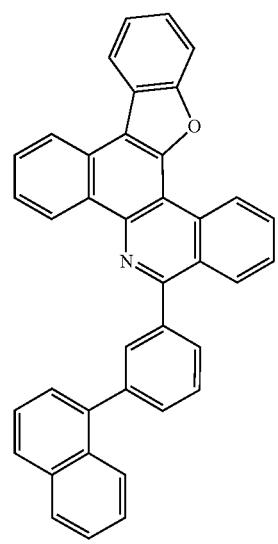
P-8-19
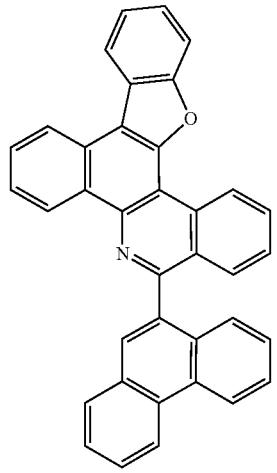
P-8-17
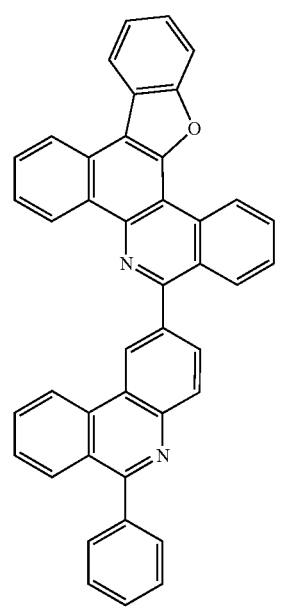
P-8-20
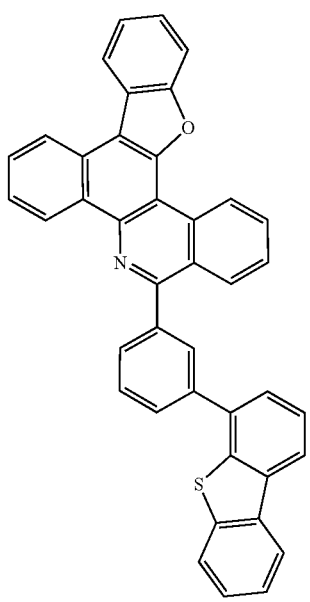
P-8-18
P-9-1
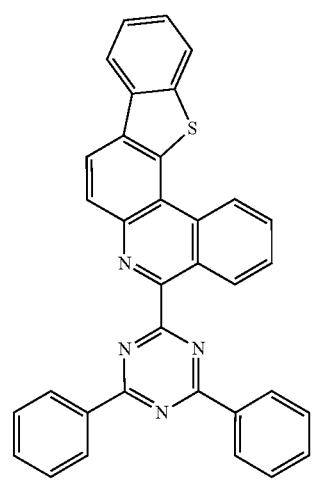

-continued
P-9-2
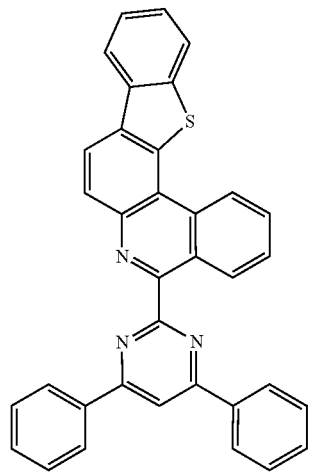
P-9-3
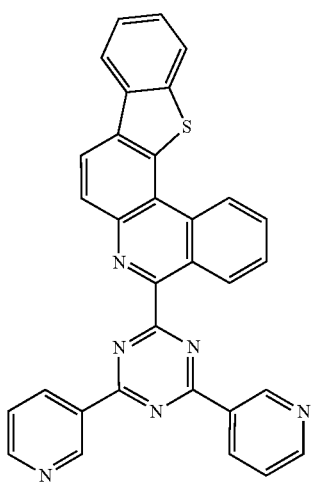
P-9-4
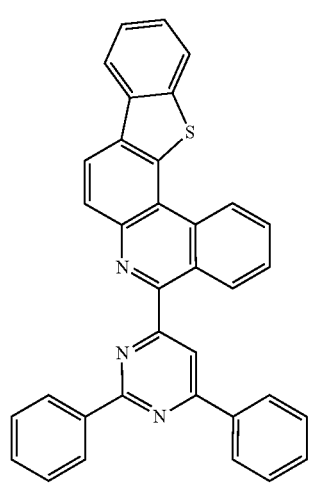
-continued
P-9-5
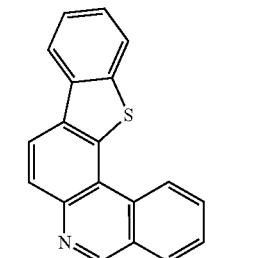
P-9-6
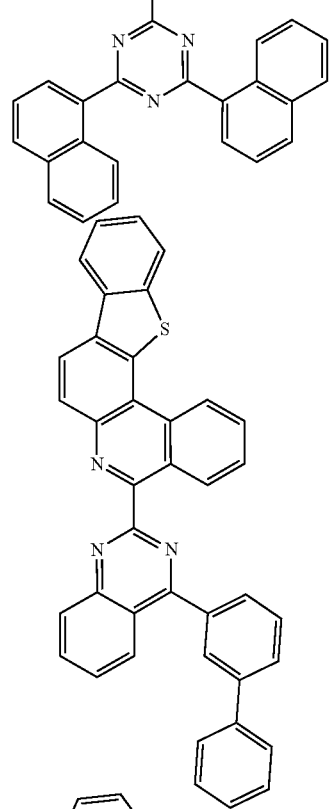
P-9-7
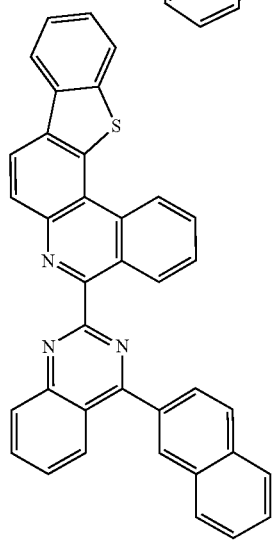

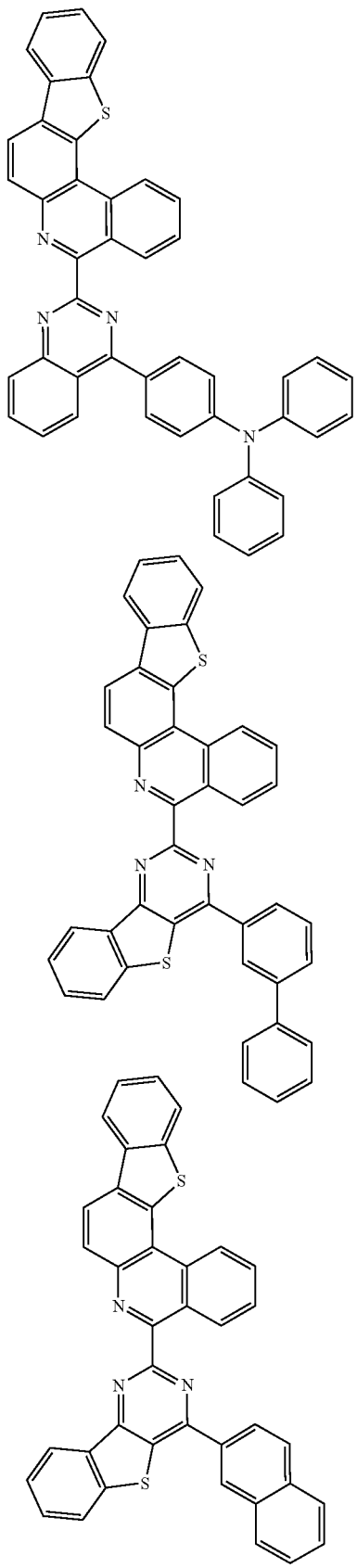
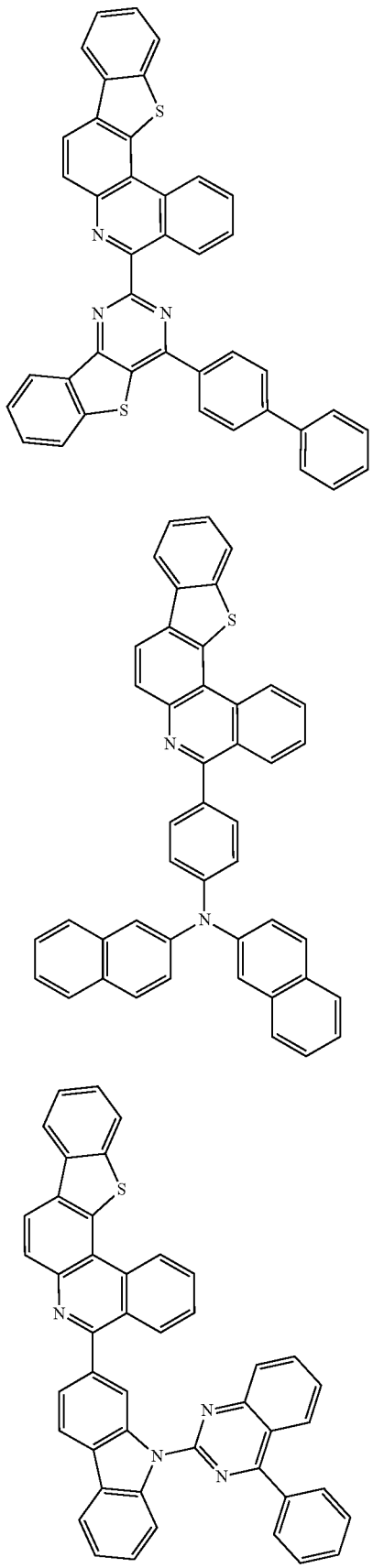

P-9-14
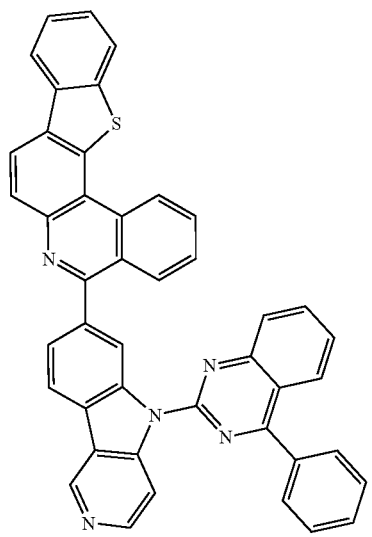
P-9-15
P-9-16
P-9-17
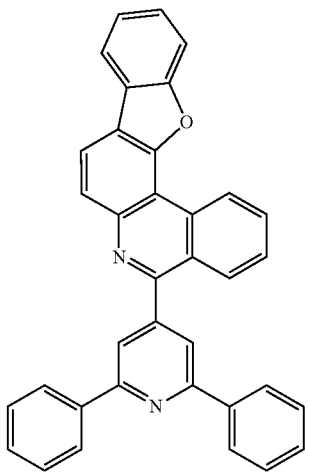
P-9-18
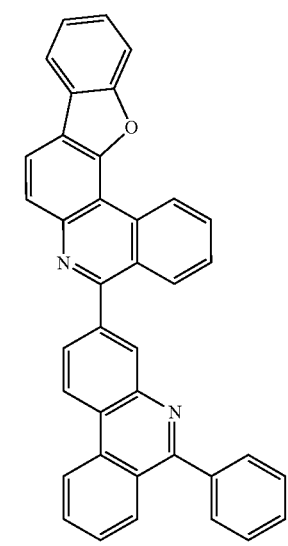
P-9-19
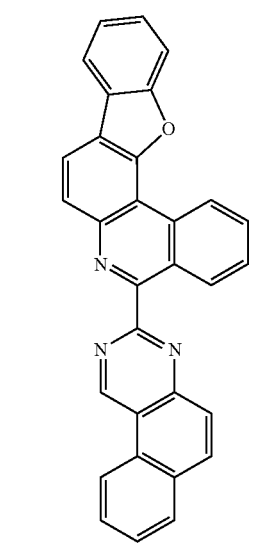

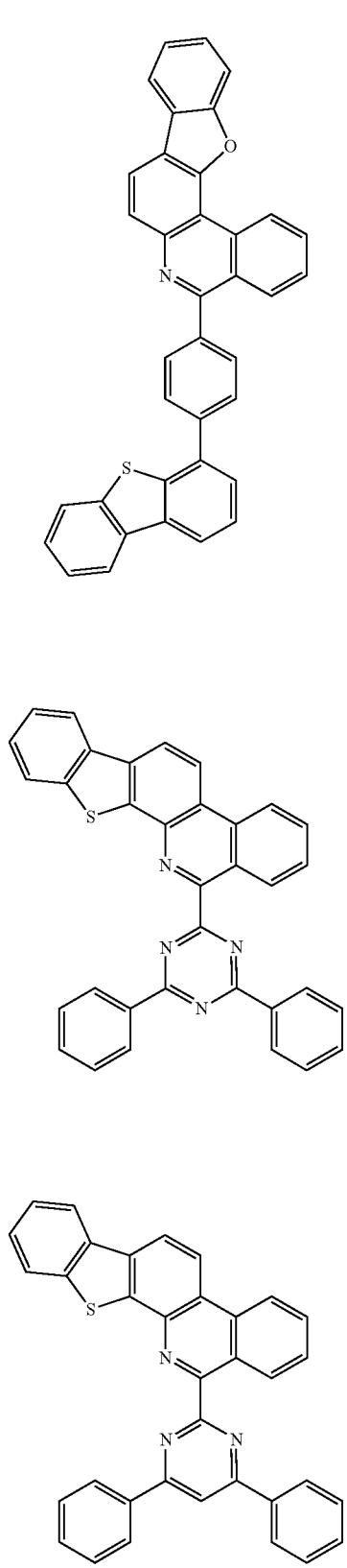

P-10-6
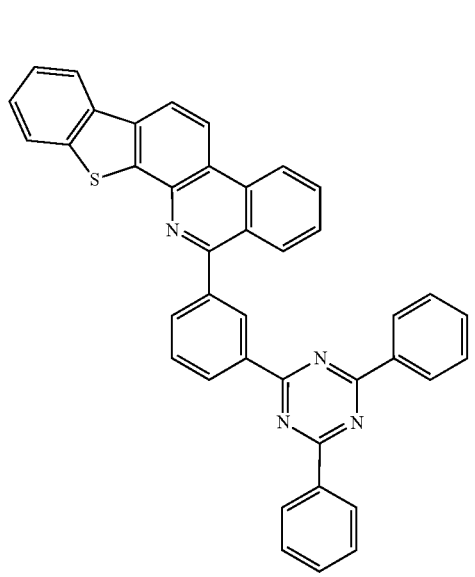
P-10-9
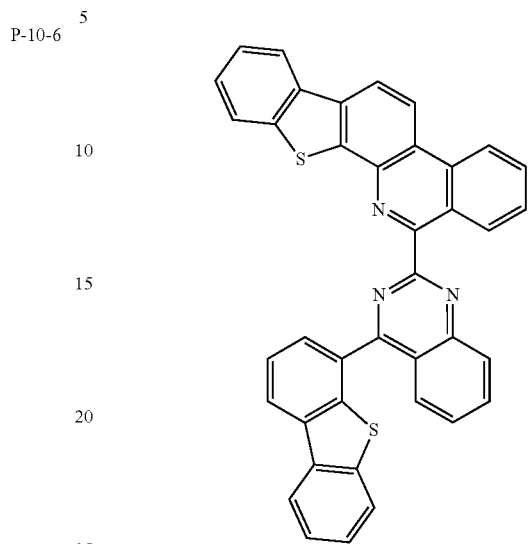
P-10-7
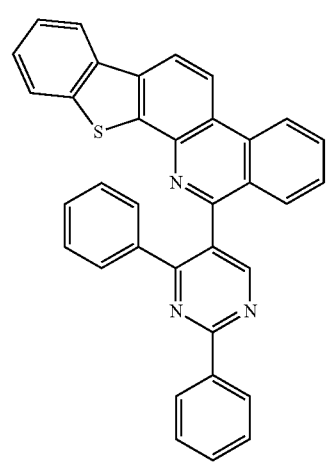
P-10-10
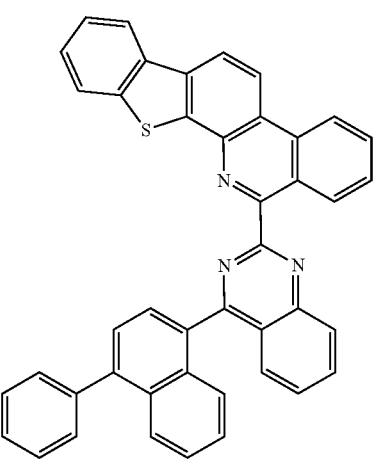
P-10-8
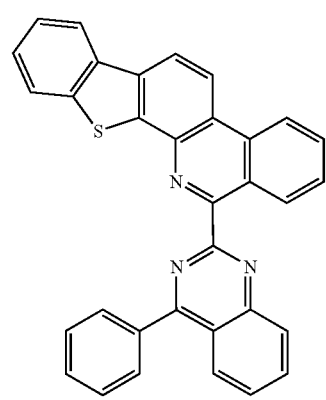
P-10-11
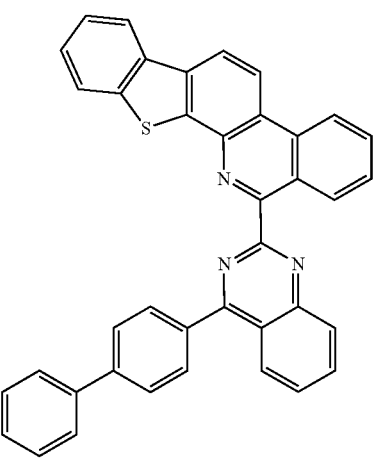

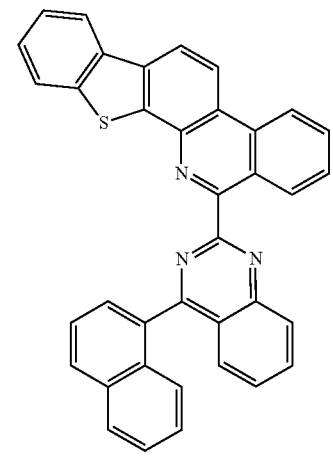
P-10-12
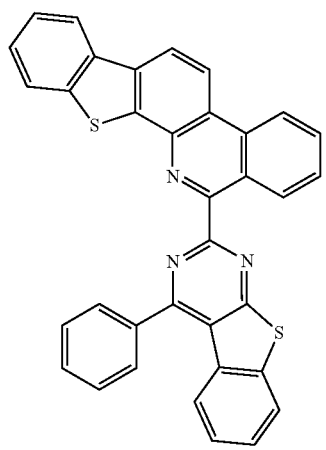
P-10-15
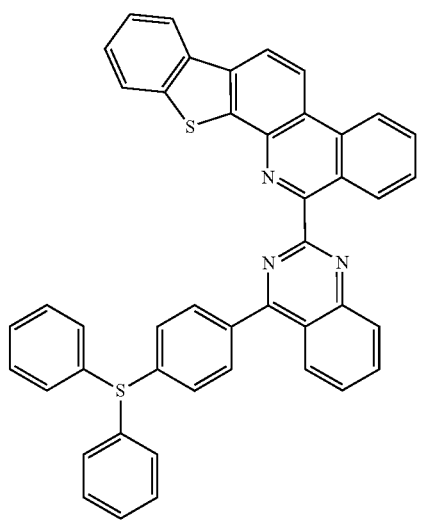
P-10-13
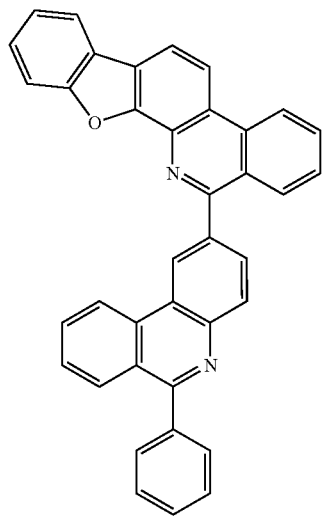
P-10-16
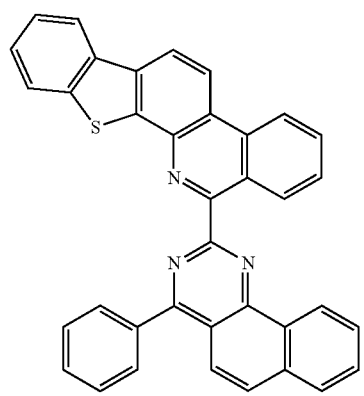
P-10-14
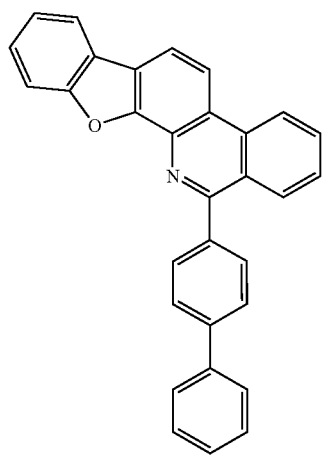
P-10-17

P-10-18

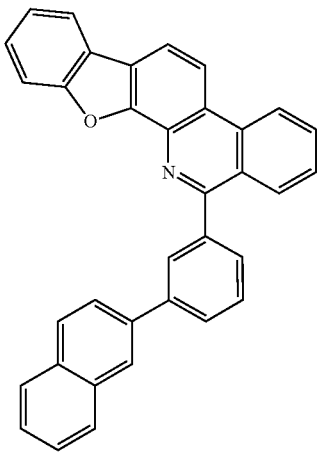

P-10-19

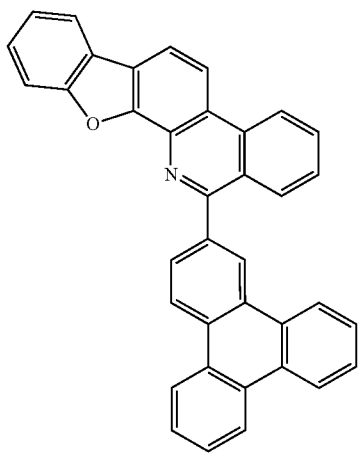

or

P-10-20

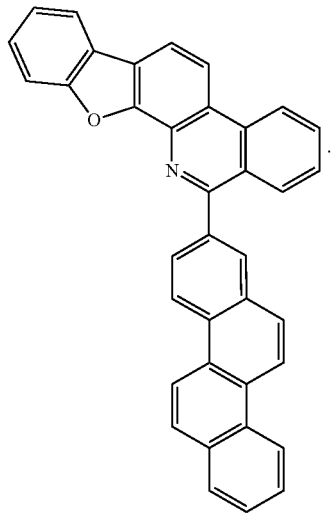

5. An organic electric element comprising a first electrode, a second electrode, and an organic material layer formed between the first electrode and the second electrode, wherein the organic material layer comprises the compound of claim 1.

6. The organic electric element of claim 5, wherein the compound is comprised in a light emitting layer of the organic material layer.

7. The organic electric element of claim 6, wherein the compound is used as a phosphorescent host material of the light emitting layer.

8. The organic electric element of claim 5, further comprising a layer for improving luminous efficiency formed on one side of the first electrode and/or one side of the second electrode, the side not facing the organic material layer.

9. The organic electric element of claim 5, wherein the organic material layer formed by any one of the processes of spin coating, nozzle printing, inkjet printing, slot coating, dip coating or roll-to-roll.

10. An electric device comprising a display device and a control unit for driving the display device, wherein the display device comprises the organic electric element of claim 5.

11. The electric device of claim 10, wherein the organic electric element is an organic light emitting diode, an organic solar cell, an organic photo conductor, an organic transistor, or an element for monochromatic or white illumination.

* * * * *

UNITED STATES PATENT AND TRADEMARK OFFICE
CERTIFICATE OF CORRECTION

PATENT NO. : 10,968,208 B2
APPLICATION NO. : 15/758827
DATED : April 6, 2021
INVENTOR(S) : Jang et al.

Page 1 of 1

It is certified that error appears in the above-identified patent and that said Letters Patent is hereby corrected as shown below:

In the Claims

Claim 1, Column 132, Line 42:
Please delete "Are"
And replace with -- $Ar^2$ --

Claim 1, Column 133, Line 2:
Please delete "06-020"
And replace with -- $C_6$-$C_{20}$ --

Signed and Sealed this
Fifteenth Day of June, 2021

Drew Hirshfeld
*Performing the Functions and Duties of the
Under Secretary of Commerce for Intellectual Property and
Director of the United States Patent and Trademark Office*